(12) United States Patent
Manash et al.

(10) Patent No.: US 12,245,756 B2
(45) Date of Patent: Mar. 11, 2025

(54) UNIDIRECTIONAL VALVULAR IMPLANT

(71) Applicant: Edwards Lifesciences Corporation, Irvine, CA (US)

(72) Inventors: Boaz Manash, Givat Ada (IL); Eitan Atias, Tel Aviv (IL); Liron Tayeb, Peduel (IL); Amir Blumenfeld, Tel Aviv (IL); David Maimon, Atlit (IL); Eyal Leiba, N. Misgav (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 614 days.

(21) Appl. No.: 17/334,479

(22) Filed: May 28, 2021

(65) Prior Publication Data

US 2021/0282757 A1 Sep. 16, 2021

Related U.S. Application Data

(63) Continuation of application No. PCT/US2019/064376, filed on Dec. 4, 2019.

(60) Provisional application No. 62/776,100, filed on Dec. 6, 2018.

(51) Int. Cl.
*A61B 17/00* (2006.01)
*A61F 2/24* (2006.01)

(52) U.S. Cl.
CPC ........ *A61B 17/0057* (2013.01); *A61F 2/2418* (2013.01); *A61B 2017/00632* (2013.01);
(Continued)

(58) Field of Classification Search
CPC ...... A61B 17/0057; A61B 2017/00575; A61B 2017/00592; A61B 2017/00597;
(Continued)

(56) References Cited

U.S. PATENT DOCUMENTS

2002/0026233 A1* 2/2002 Shaknovich .......... A61F 2/2412
623/2.11
2005/0273160 A1* 12/2005 Lashinski ............. A61F 2/2436
604/9
(Continued)

FOREIGN PATENT DOCUMENTS

JP 2002263112 A 9/2002
WO 0217819 A2 3/2002
(Continued)

*Primary Examiner* — Robert A Lynch
(74) *Attorney, Agent, or Firm* — Calfee, Halter & Griswold LLP; Linda Allyson Nassif

(57) ABSTRACT

Valvular implants and blood vessel closure devices herein are configured to be positioned in the heart and to block regurgitant blood flow from the heart into blood vessels supplying blood to the heart. The valvular implants can have a cover, a membrane, a valve, a resilient frame, and/or other features. Some valvular implants can have anchors to be positioned in the blood vessels, such as in pulmonary veins, and can anchor the implant to the heart wall. Various embodiments of covers and/or membranes act as valves contracting and expanding, to alternately permit and block blood flow. The valvular implants can cover one or more blood vessels, such as one, two, three, or four pulmonary veins, and can also be configured and implanted to block an appendage to the heart, such as the left atrial appendage.

20 Claims, 67 Drawing Sheets

(52) U.S. Cl.
CPC .............. *A61B 2017/00646* (2013.01); *A61F 2210/0014* (2013.01)

(58) Field of Classification Search
CPC ........... A61B 2017/00601; A61B 2017/00606; A61B 2017/0061; A61B 2017/00615; A61B 2017/00628; A61B 2017/00632; A61B 2017/00646; A61F 2/24; A61F 2/2403; A61F 2/2409; A61F 2/2412; A61F 2/2418; A61F 2210/0014
See application file for complete search history.

(56) References Cited

U.S. PATENT DOCUMENTS

| | | | | |
|---|---|---|---|---|
| 2009/0088648 | A1* | 4/2009 | Jaffe | A61B 5/0084 |
| | | | | 600/466 |
| 2011/0106244 | A1 | 5/2011 | Ferrari et al. | |
| 2014/0200663 | A1* | 7/2014 | Ferrari | A61F 2/2409 |
| | | | | 623/2.38 |
| 2016/0302920 | A1* | 10/2016 | Al-Jilaihawi | A61F 2/2433 |
| 2016/0324639 | A1* | 11/2016 | Nguyen | A61F 2/2409 |
| 2017/0056176 | A1* | 3/2017 | Rowe | A61F 2/2412 |
| 2017/0128205 | A1* | 5/2017 | Tamir | A61F 2/2439 |

FOREIGN PATENT DOCUMENTS

| | | |
|---|---|---|
| WO | 03028558 A2 | 4/2003 |
| WO | 2015135763 A1 | 9/2015 |
| WO | 2017062515 A1 | 4/2017 |
| WO | 2017217932 A1 | 12/2017 |

\* cited by examiner

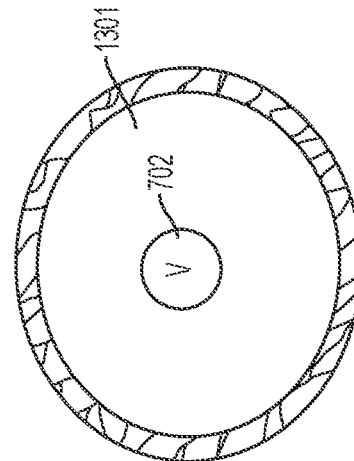
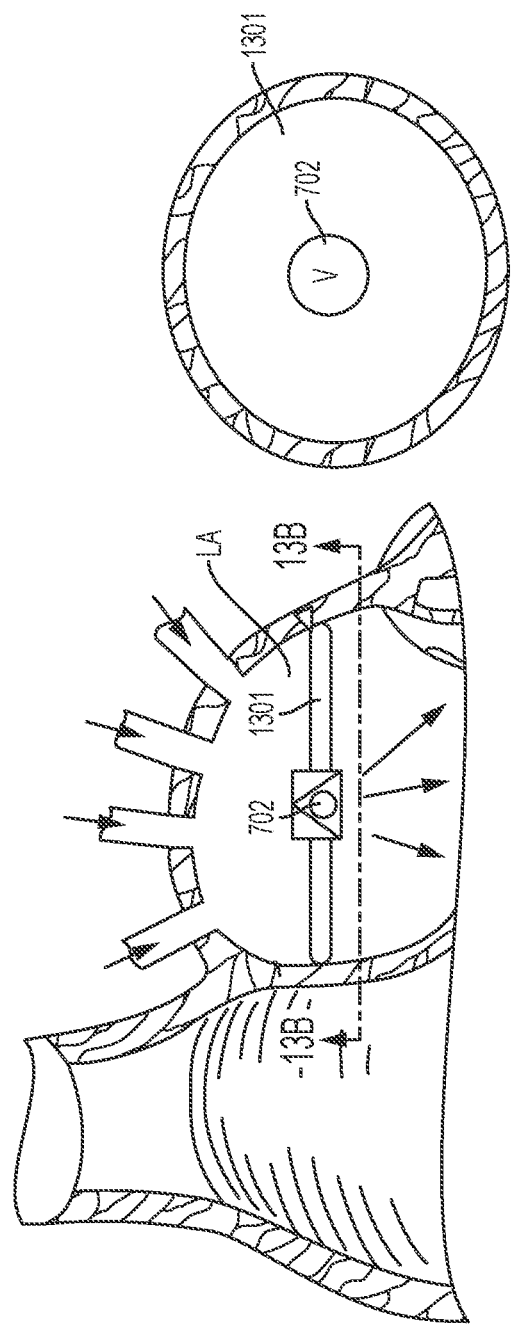
FIG. 13B
FIG. 13A

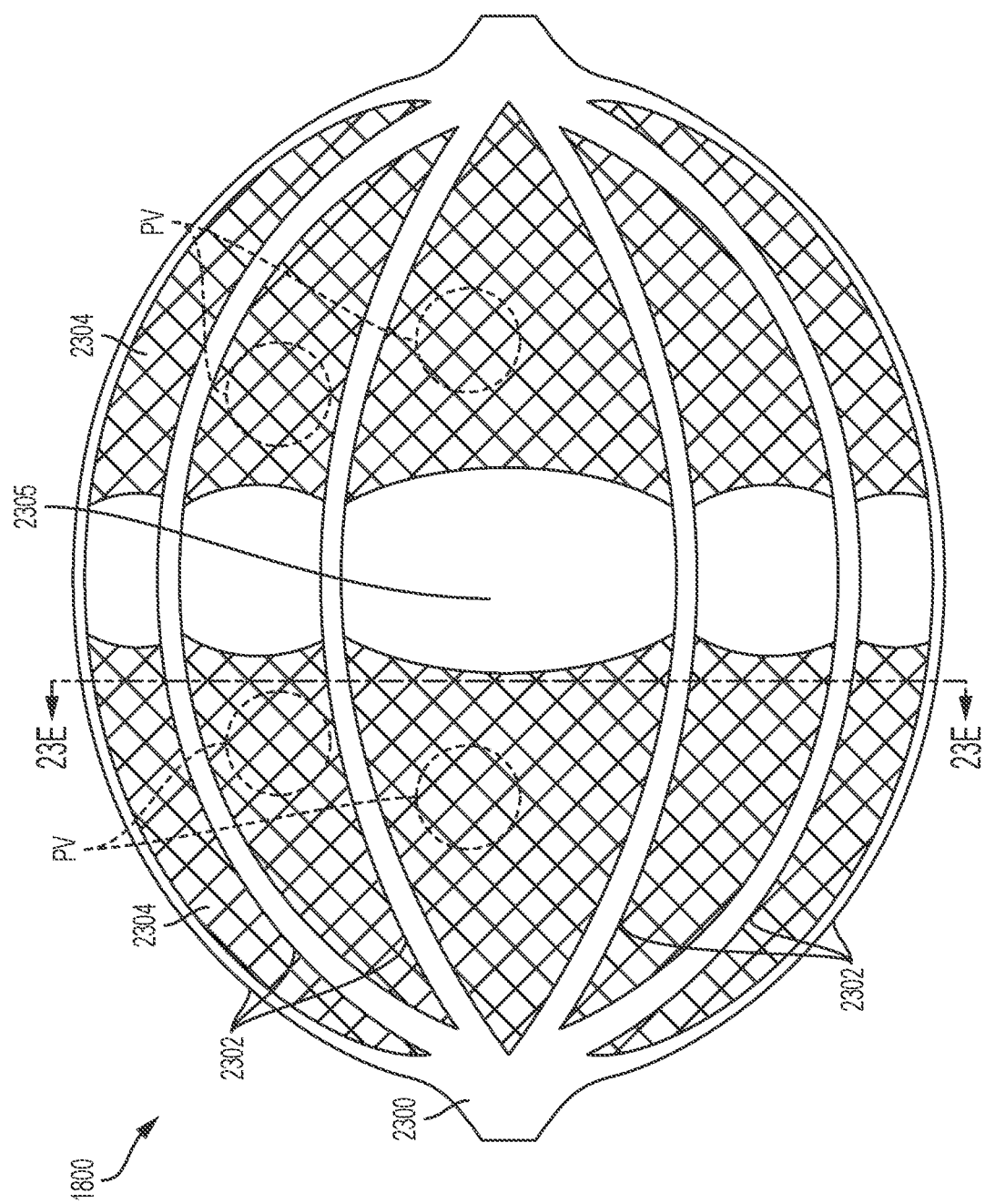

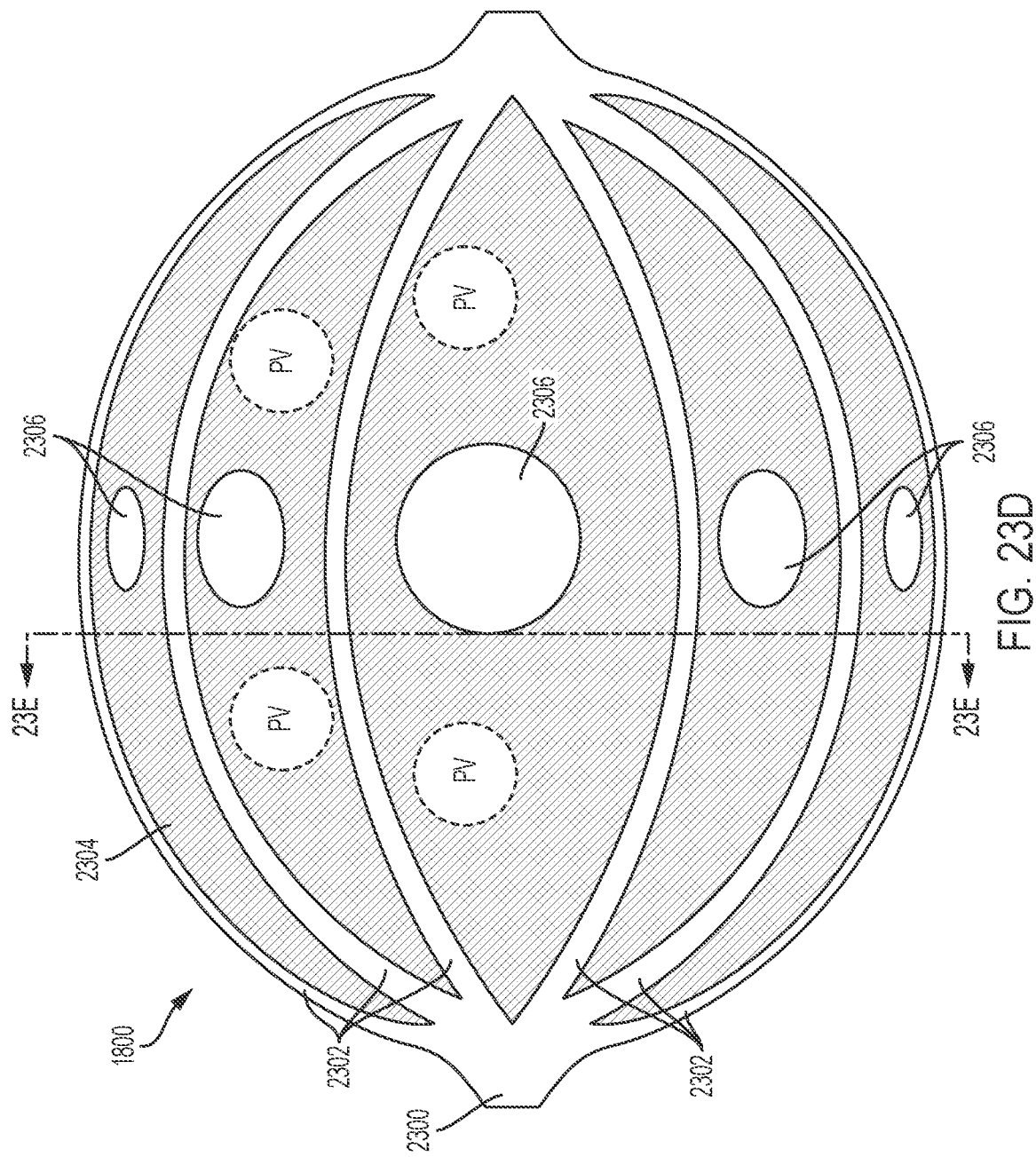

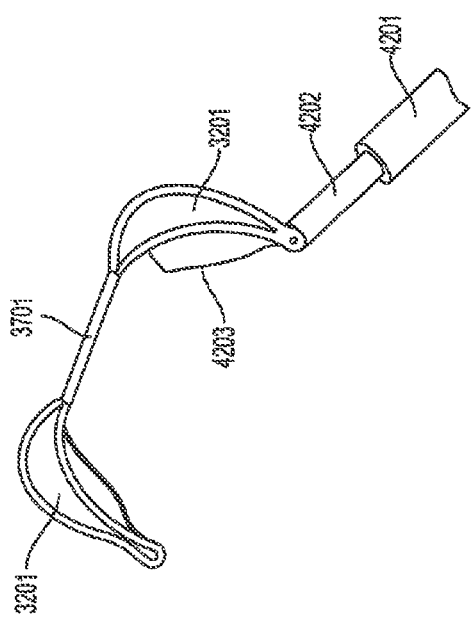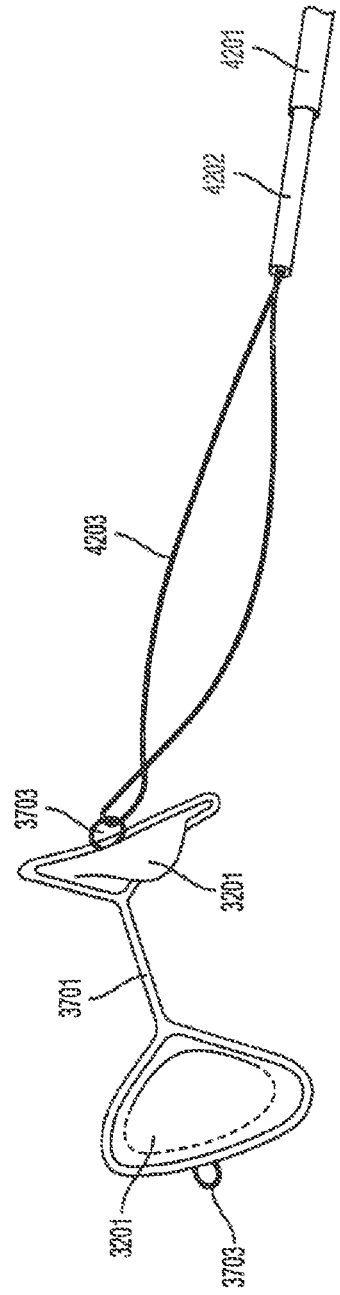

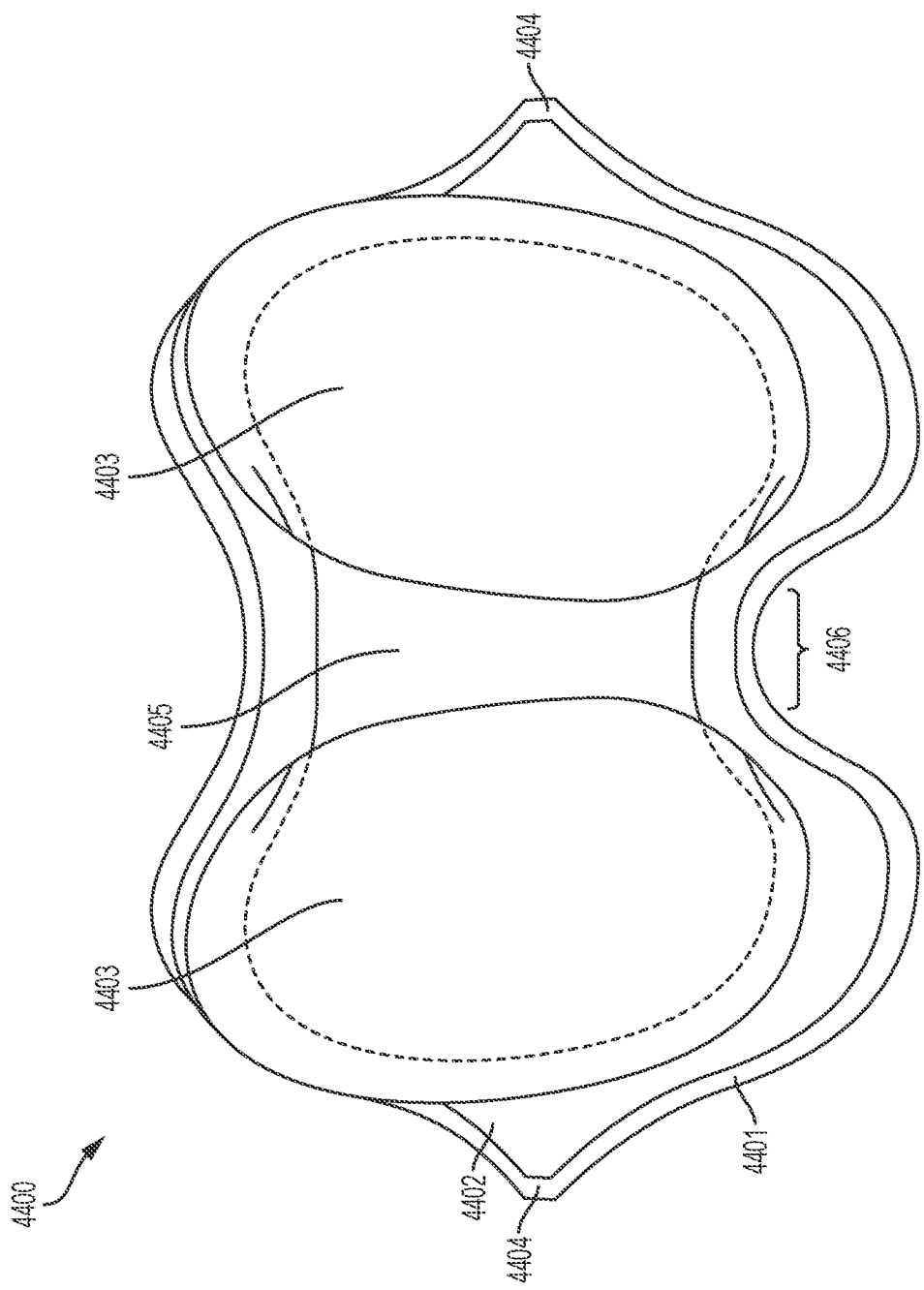

UNIDIRECTIONAL VALVULAR IMPLANT

RELATED APPLICATION

The present application is a continuation of PCT application PCT/US2019/064376, filed on Dec. 4, 2019, which claims the benefit of U.S. provisional patent application Ser. No. 62/776,100 filed on Dec. 6, 2018, titled "Unidirectional Valvular Implant", each of which being incorporated herein by reference in its entirety.

BACKGROUND

The function of the heart can be seriously impaired if any of the heart valves are not functioning properly. The heart valves may lose their ability to close properly due to e.g. dilation of an annulus around the valve, ventricular dilation, or a leaflet being flaccid causing a prolapsing leaflet, etc., The leaflets may also have shrunk due to disease, e.g. rheumatic disease, and thereby leave a gap in the valve between the leaflets. The inability of the heart valve to close properly can cause a leak backwards (i.e., from the outflow to the inflow side), commonly referred to as regurgitation, through the valve and/or blood vessels. Heart valve regurgitation may seriously impair the function of the heart since more blood will have to be pumped through the regurgitating valve to maintain adequate circulation. Heart valve regurgitation decreases the efficiency of the heart, reduces blood circulation, and adds stress to the heart. In early stages, heart valve regurgitation leaves a person fatigued or short of breath. If left unchecked, the problem can lead to congestive heart failure, arrhythmias or death.

Heart valve disease, which can include valve regurgitation, is typically treated by replacing or repairing the diseased valve. However, indirect methods of treatment could be considered advantageous when the anatomy of the mitral valve is malfunctioning but not diseased.

Functional mitral regurgitation (MR) is a common clinical entity which can occur when the mitral valve is structurally normal, and the regurgitation results from failure of coaptation of the mitral valve leaflets without coexisting structural changes of the valve itself. Functional MR is different than primary MR in that in primary MR the mitral valve structure and function are comprised, resulting in either compromised or structurally disrupted components of the mitral valve, which can be caused by a variety of diseases.

FIGS. 1 and 2 are cutaway views of the human heart H in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta AA, and the pulmonary valve PV separates the right ventricle from the pulmonary artery PA. Each of these valves has flexible leaflets (e.g., leaflets 502, 504 shown in FIGS. 5 and 6) extending inward across the respective orifices that come together or "coapt" in the flowstream to form the one-way, fluid-occluding surfaces.

FIGS. 3 and 4 are illustrations of the human heart H, including the pulmonary veins 301 and pulmonary vein orifices 302 located in the surface of the left atrium LA wall. FIG. 3 illustrates approximate anatomical locations of the pulmonary veins PV. The pulmonary veins can be grouped into two pairs of pulmonary veins, each pair providing blood flow from one lung to the left atrium. This pairing and the anatomical distance between each pulmonary vein, can be used to determine which exemplary embodiment is appropriate to implant. FIG. 4 illustrates a simplified schematic cutaway view of the heart having four pulmonary veins which empty into the left atrium LA.

For illustrative purposes, the native valve repair systems of the present application are described primarily with respect to the mitral valve MV. Therefore, anatomical structures of the left atrium LA and Left ventricle LV will be explained in greater detail. It should be understood, however, that the devices described herein can also be adapted for use in repairing other portions of the body, native valves, and/or blood vessels, e.g., the devices can be used in repairing the tricuspid valve TV, for example, by preventing backflow into one or more of an inferior vena cava IVC, the superior vena cava SVC, and/or coronary sinus CS.

The left atrium LA receives oxygenated blood from the lungs. During the diastolic phase, or diastole, seen in FIG. 1, the blood that collects in the left atrium LA enters the mitral valve MV by expansion of the left ventricle LV. In the systolic phase, or systole, seen in FIG. 2, the left ventricle LV contracts to force the blood through the aortic valve AV and ascending aorta AA into the body. During systole, the leaflets of the mitral valve MV close to prevent the blood from regurgitating back into the left atrium LA.

Referring to FIGS. 1-6, the mitral valve MV is shown having two leaflets, an anterior leaflet 502 and a posterior leaflet 504. The mitral valve MV also includes an annulus 506, which is a variably dense fibrous ring of tissues that encircles the leaflets 502, 504. The mitral valve MV opens and closes in response to pressure changes in the left atrium LA and the left ventricle LV. The papillary muscles do not open or close the mitral valve MV. Rather, the papillary muscles brace the mitral valve MV against the high pressure needed to circulate blood throughout the body. Together the papillary muscles and the chordae tendineae are known as the subvalvular apparatus, which functions to keep the mitral valve MV from prolapsing into the left atrium LA when the mitral valve closes.

Various disease processes can impair proper function of one or more of the native valves of the heart H. These disease processes include degenerative processes (e.g., Barlow's Disease, fibroelastic deficiency), inflammatory processes (e.g., Rheumatic Heart Disease), and infectious processes (e.g., endocarditis). In addition, damage to the left ventricle LV or the right ventricle RV from prior heart attacks (i.e., myocardial infarction secondary to coronary artery disease) or other heart diseases (e.g., cardiomyopathy) can distort a native valve's geometry, which can cause the native valve to dysfunction. However, the majority of patients undergoing valve surgery, such as surgery to the mitral valve MV, suffer from a degenerative disease that causes a malfunction in a leaflet (e.g., leaflets 502, 504) of a native valve (e.g., the mitral valve MV), which results in prolapse and regurgitation.

A native valve may malfunction in multiple different ways. One possible malfunction is valve stenosis, which occurs when a native valve does not open completely and thereby causes an obstruction of blood flow. Typically, valve stenosis results from buildup of calcified material on the leaflets of a valve, which causes the leaflets to thicken and impairs the ability of the valve to fully open to permit forward blood flow.

Another possible malfunction is valve regurgitation, which occurs when the leaflets of the valve do not close completely thereby causing blood to leak back into the prior chamber (e.g., causing blood to leak from the left ventricle to the left atrium). There are three mechanisms by which a native valve becomes regurgitant or incompetent, which include Carpentier's type I, type II, and type III malfunctions. A Carpentier's type I malfunction involves the dilation of the annulus such that normally functioning leaflets are distracted from each other and fail to form a tight seal (i.e., do not coapt properly). Included in a type I mechanism malfunction are perforations of the leaflets, as in endocarditis. A Carpentier's type II malfunction involves prolapse of one or more leaflets of a native valve above a plane of coaptation. A Carpentier's type III malfunction involves restriction of the motion of one or more leaflets of a native valve such that the leaflets are abnormally constrained below the plane of the annulus. Leaflet restriction can be caused by rheumatic disease (IIIa) or dilation of a ventricle (IIIb).

Referring to FIG. 5, when a healthy mitral valve MV is in a closed position, the anterior leaflet 502 and the posterior leaflet 504 coapt, which prevents blood from leaking from the left ventricle LV to the left atrium LA. Referring to FIG. 6, regurgitation can occur when the anterior leaflet 502 and/or the posterior leaflet 504 of the mitral valve MV is displaced into the left atrium LA and/or does not coapt with the other leaflet during systole. This failure to coapt causes a gap 608 between the anterior leaflet 502 and the posterior leaflet 504, which allows blood to flow back into the left atrium LA from the left ventricle LV during systole. As set forth above, there are several different ways that a leaflet (e.g. leaflets 502, 504 of mitral valve MV) may malfunction, which can thereby lead to regurgitation.

Regurgitation is a common problem that affects the mitral valve MV and the tricuspid valve TV. Both valve stenosis and valve regurgitation increase the workload of the heart H and may lead to very serious conditions if left un-treated, such as endocarditis, congestive heart failure, permanent heart damage, cardiac arrest, and ultimately death. Because the left side of the heart (i.e., the left atrium LA, the left ventricle LV, the mitral valve MV, and the aortic valve AV) is primarily responsible for circulating the flow of blood throughout the body, malfunction of the mitral valve MV or the aortic valve AV is particularly problematic and often life threatening. Accordingly, because of the substantially higher pressures on the left side of the heart, dysfunction of the mitral valve MV or the aortic valve AV can be more problematic.

Heart valve disease, such as valve regurgitation, is typically treated by replacing or repairing the diseased valve.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

In one exemplary embodiment, the implants, devices, and systems described by the present application are used to repair or improve the function of a defective mitral valve MV.

An exemplary apparatus, implant, or device for closing and/or covering a pulmonary vein opening in the left atrium of a heart has at least one pulmonary vein closure device or cover with a resilient frame and a valve. The pulmonary vein closure device has two configurations: an open configuration which permits blood to flow from a pulmonary vein into the left atrium, and a closed configuration which blocks blood flow from the left atrium into the pulmonary vein.

In some embodiments, the apparatus or device can also have a second resilient frame and a bridge connecting the frames, with one or more membranes attached to and spanning across each resilient frame. The one or more membranes can be part of an embodiment having an opening and a leaflet or flap attached to the membrane over the opening. The membranes can also be part of an embodiment where each membrane has an opening and the membrane bunches up to close the opening. The various embodiments can also have strain-reducing loops on each of the resilient frames.

In some embodiments, the resilient frame can have struts and a membrane covering the struts to define an interior volume. The membrane can be collapsed inward to define the open configuration and the membrane when expanded can define the closed configuration. In some embodiments, the open configuration provides flow channels between the membrane and the left atrial wall. In the closed configuration, the membrane can be configured to abut the pulmonary vein orifices to block fluid flow.

In various embodiments, the valve can be a check valve and the resilient frame can have one or more of friction enhancing elements and/or a covering on at least a portion of the frame.

In various embodiments, the frame can anchor the valve in the left atrium. In various embodiments, the apparatus can comprise at least one anchor (e.g., a first anchor) or one or more anchors. A cover or membrane can be connected to the resilient frame such that the cover or membrane creates a seal between an anchor and the frame. In some embodiments, there can be a second anchor. The second anchor can be integral with the frame and/or connected to the frame by a membrane, and can be connected to the first anchor by the membrane and/or a connecting portion of the frame. The anchors and valve can be integral with the frame and/or be connected to the frame by the same membrane. In some embodiments, the pulmonary vein cover also has a third and fourth anchor connected to the membrane. One, some, or all of the anchors can be configured as a stent, such as a cylindrical stent portion, etc.

Methods for implanting an apparatus, device, or system in the heart (for example, any of the devices, apparatuses, and/or systems described above or elsewhere herein) can have, and in some embodiments do have, one or more of the following steps: inserting a guide catheter into a left atrium of a heart; advancing a delivery tube having at least one compressed pulmonary vein cover or closure device, into the left atrium; and expanding the pulmonary vein cover or closure device in the left atrium. Additional method steps can include removing a pull wire or suture from the pulmonary vein cover or closure device. The method can include implanting the pulmonary vein cover or closure device with an integrated valve and anchor, and/or it can include implanting an anchor and a valve separately.

BRIEF DESCRIPTION OF THE DRAWINGS

Further features and advantages of the invention will become apparent from the description of embodiments using the accompanying drawings. In the drawings:

FIG. 13A illustrates a schematic of a portion of the human heart with an exemplary ring-shaped support with a valve, such as a check valve, in an open position.

FIG. 13B is a plan view of the exemplary embodiment of the support and valve illustrated in FIG. 13A.

FIG. 23C illustrates an exemplary embodiment of membranes attached to the frame of FIGS. 23A and 23B.

FIG. 23D illustrates an exemplary embodiment of a membrane with openings attached to the frame of FIGS. 23A and 23B.

FIGS. 42A-42I illustrate exemplary steps that can be used in deploying and implanting a valvular implant in accordance with the embodiments illustrated in FIGS. 34-41.

FIG. 44 illustrates an exemplary valvular implant or device having a wire frame and two valves or valve portions or sections.

DETAILED DESCRIPTION

Disclosed herein are various exemplary embodiments of implant devices, apparatuses, and systems that can be docked in a chamber of the heart or atrium and/or nearby blood vessels (e.g., the left atrium and/or pulmonary veins of the heart), methods of implanting the devices, and methods of covering an implant with a soft material. The devices, apparatuses, systems, etc. disclosed herein can provide an indirect treatment of valve regurgitation, such as mitral valve regurgitation. The devices, apparatuses, systems, etc. disclosed can be used to prevent blood from flowing back in an incorrect direction through blood vessels. The various devices, apparatuses, systems, etc. can be expandable from a compressed condition (e.g., sufficient for transvascular or transfemoral delivery to the heart with a delivery catheter) to an expanded or deployed condition.

For example, the devices, apparatuses, systems, etc. herein can be used to prevent blood in the left atrium from flowing back into the pulmonary veins when the heart has a regurgitant mitral valve. For example, the implants, devices, apparatuses, systems, etc. can be used to block blood from flowing into the pulmonary veins by blocking the pulmonary vein orifices when the heart is in systole, as this could occur in the case of mitral valve prolapse or other mitral valve or other heart deficiency. The implants, devices, apparatuses, systems, etc. herein can have a valve or valve portion and a resilient frame. The frame can provide a place or docking/landing zone for a valve to be inserted or have a valve or valve member integral to the frame. Implanting such a valve in the left atrium and/or pulmonary veins can prevent high pressures below or downstream of the valve location, reducing the consequences of regurgitation, for example, the flow of blood from the left atrium into the pulmonary veins, which can cause pulmonary edema.

Figure 1:
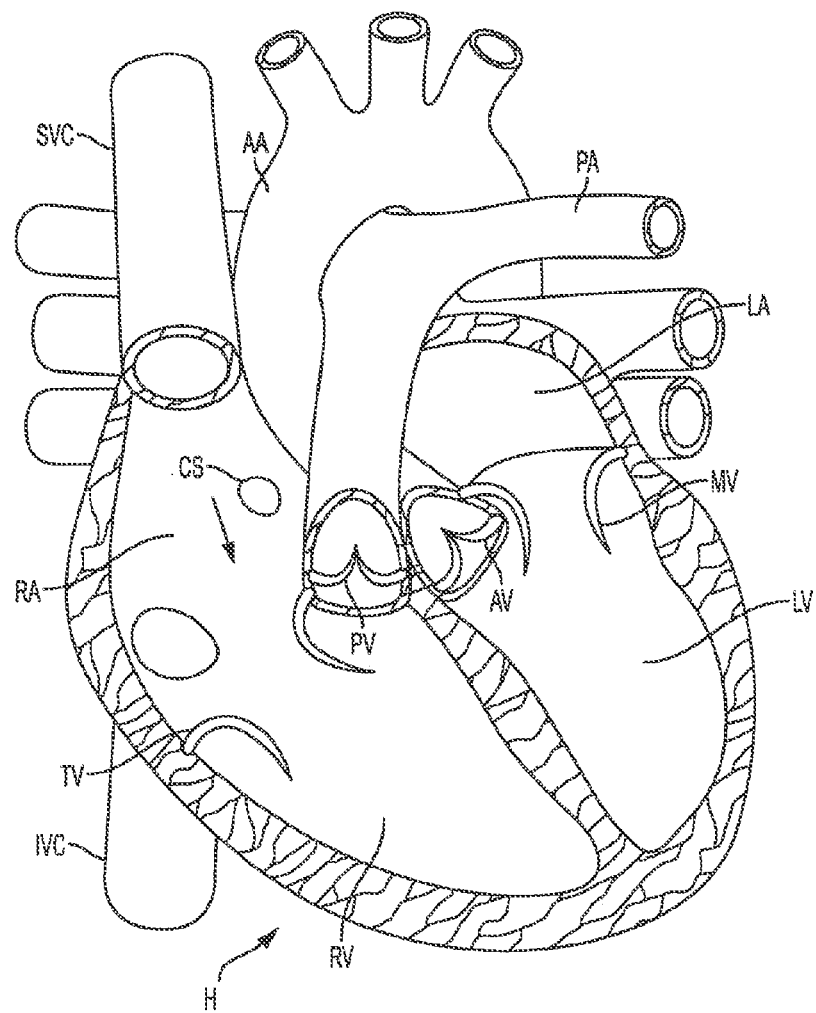
FIG. 1 illustrates a cutaway view of the human heart in a diastolic phase.
Figure 2:
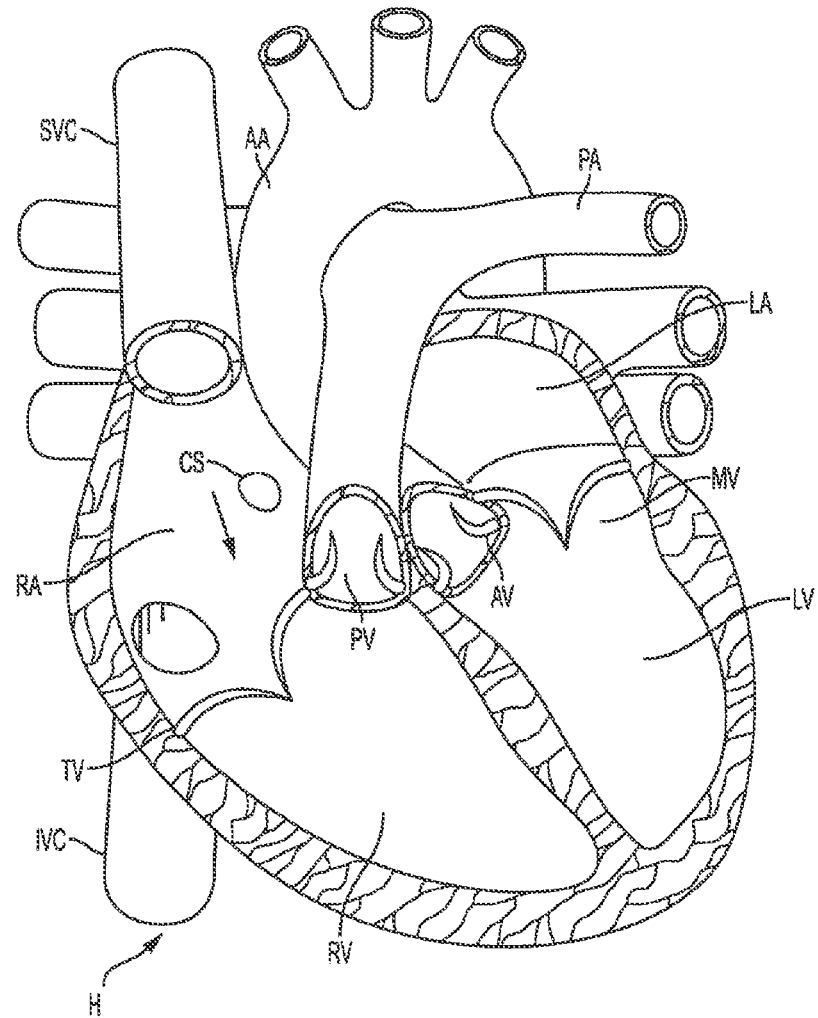
FIG. 2 illustrates a cutaway view of the human heart in a systolic phase.
Figure 3:
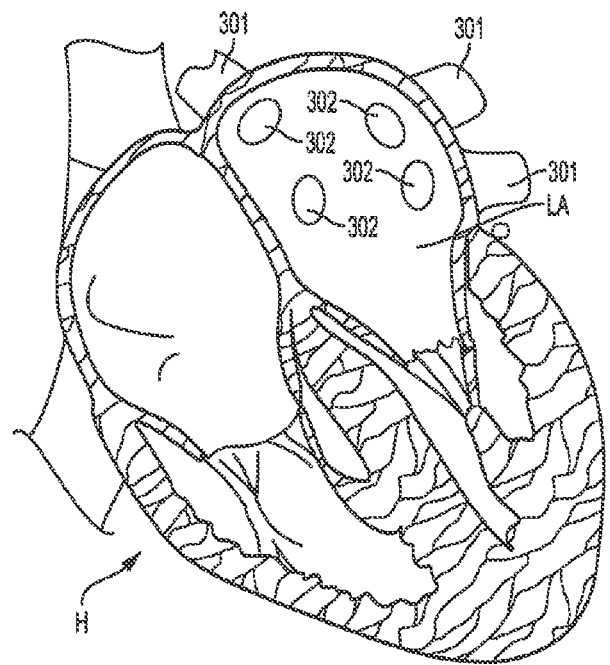
FIG. 3 illustrates a cutaway view of the human heart having four pulmonary vein orifices.
Figure 4:
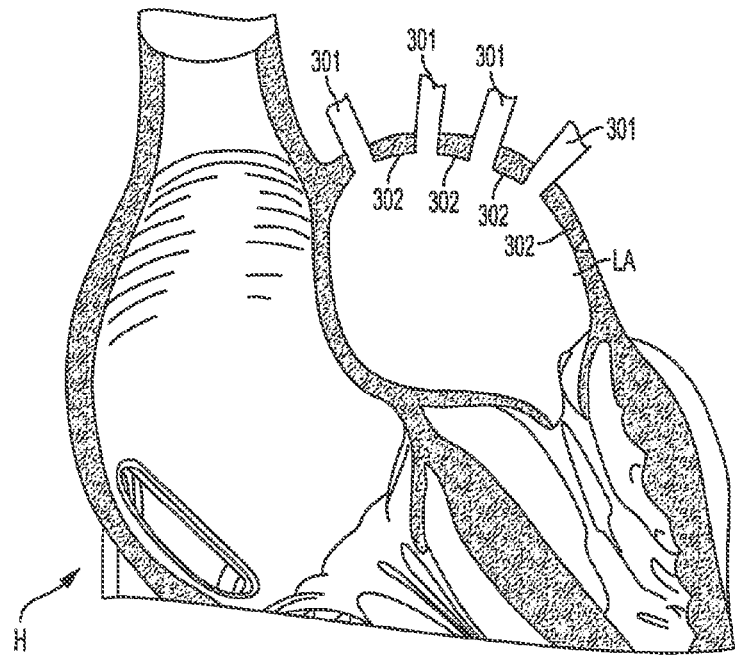
FIG. 4 illustrates another cutaway view of the human heart having four pulmonary vein orifices.
Figure 5:
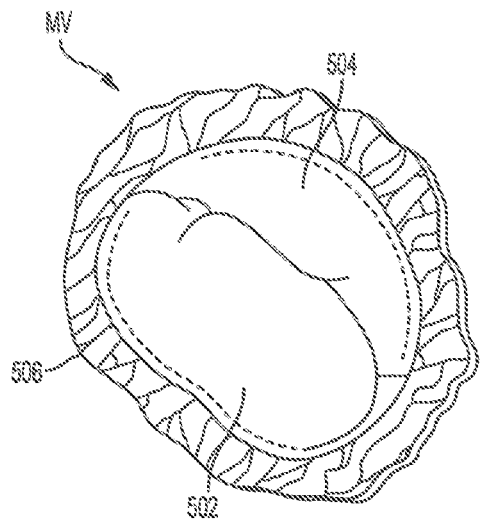
FIG. 5 illustrates a healthy mitral valve with the leaflets closed as viewed from an atrial side of the mitral valve.
Figure 6:
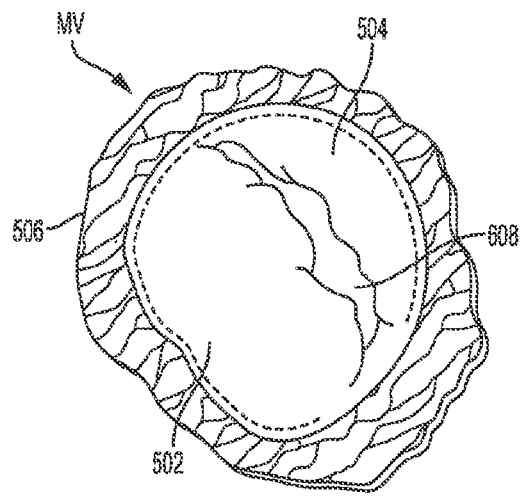
FIG. 6 illustrates a dysfunctional mitral valve with a visible gap between the leaflets as viewed from an atrial side of the mitral valve.
Figure 7:
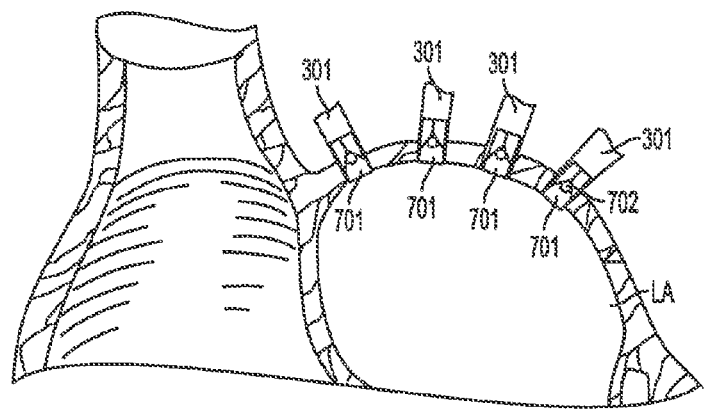
FIG. 7 illustrates a schematic view of a portion of the human heart with exemplary check valves located in the pulmonary vein orifices.
Figure 8:
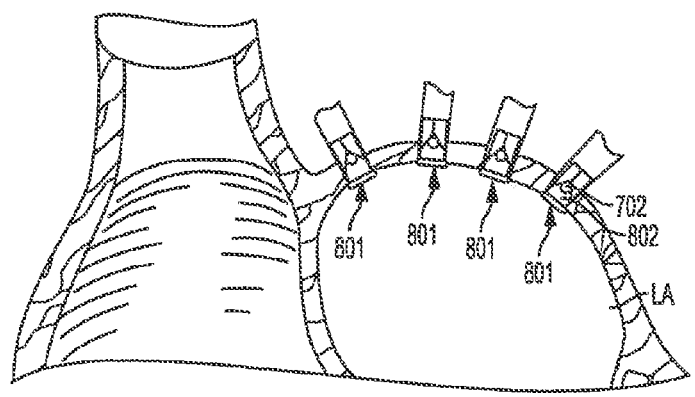
FIG. 8 illustrates a schematic view of a portion of the human heart with exemplary closed position check valves located in the pulmonary vein orifices.
Figure 9:
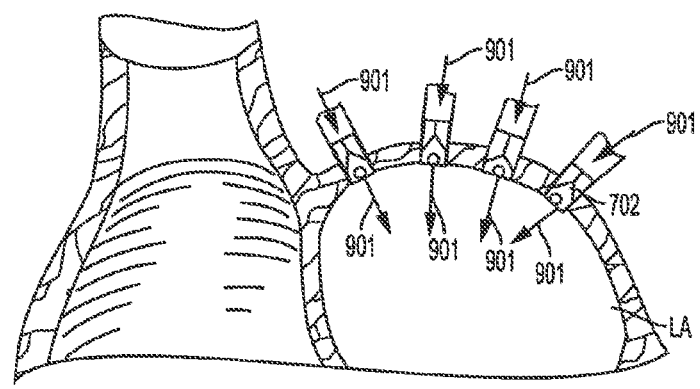
FIG. 9 illustrates a schematic view of a portion of the human heart with exemplary open position check valves in the pulmonary vein orifices.

Referring to FIGS. 7-9, a schematic of an exemplary valvular implant system or valve implant system is illustrated. FIG. 7 schematically illustrates four individual implants 701, one in each pulmonary vein 301, where each valve implant comprises a unidirectional valve or valve member 702. The valve can be a check valve having a wide variety of different forms. Any valve configured for use inside the heart can be used. FIG. 8 illustrates the valve implants 701 in a closed position. This position can occur when the heart is in systole to prevent regurgitation through the blood vessels or pulmonary veins. By positioning the unidirectional valve in a direction that the blood cannot flow from the left atrium back into the pulmonary veins, regurgitant blood flow in the left atrium caused by a deficient mitral valve is prevented. Arrows 801 indicate the direction of blood and lines 802 indicate that the valves are closed to blood flowing in the direction of the arrows. In FIG. 9, the valves 702 are in an open configuration, freely allowing the blood in the pulmonary veins to flow into the left atrium LA. Arrows 901 in FIG. 9 indicate the direction of this blood flow, through the valves and into the left atrium, which can occur, for example, when the heart is in diastole or when pressure is relatively low in the left atrium. The schematics presented in FIGS. 7-9 are representative of any of the exemplary embodiments of a single pulmonary vein check valve or valve system described herein. In this type of system, one or more valves can be used (e.g., one valve in one vein, two valves in two veins, three valves in three veins, four valves in four veins, etc.)

Valve regurgitation, such as that from a ventricle into an atrium and back into veins that feed the atrium, can be treated indirectly by placing a unidirectional valvular implant comprising a membrane in or over the veins that feed blood into the atrium, such as the four pulmonary veins in the left atrium, as illustrated in the schematic embodiments of FIGS. 10A-11B showing an "umbrella"-shaped, "umbrella"-like, or dome-like implant.

Figure 10A:
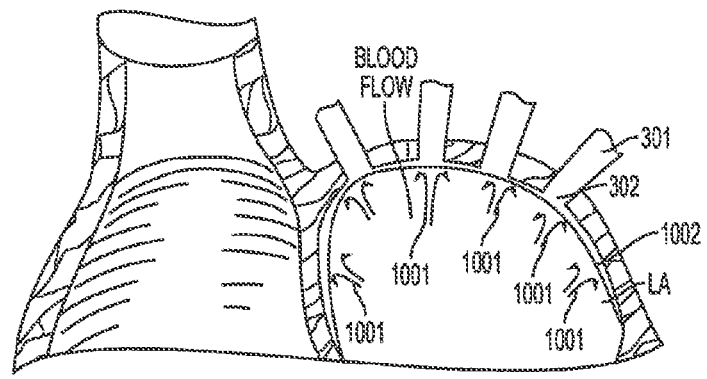
FIG. 10A illustrates a schematic view of a portion of a human heart with an exemplary membrane in a closed position.
Figure 10B:
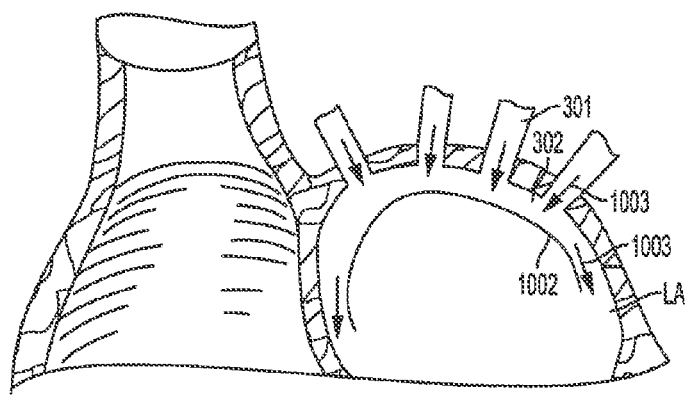
FIG. 10B illustrates a schematic view of portion of a human heart with an exemplary valvular implant or device in an open position.

Referring to FIGS. 10A and 10B, an exemplary closure device, valve, or valvular implant 1002 having a dome, umbrella, or semi-sphere shape is shown. The valvular implant 1002 is depicted as a unidirectional pulmonary vein valvular implant configured to function on all four pulmonary vein orifices 302 at once. FIG. 10A depicts the valvular implant when the heart is in systole and the pressure in the heart chamber or left atrium rises, where the valve 1002 is in a closed configuration (i.e., a configuration in which blood is prevented from flowing back into the blood vessels or pulmonary veins). In the closed position, a membrane of the valve 1002 seals over the openings to all the blood vessels (e.g., to all four depicted pulmonary veins), so that any blood in the atrium cannot flow back up into and through the blood vessels or pulmonary veins. Arrows 1001 indicate the direction in which the blood attempts to flow. The blood, in a heart with a normal mitral valve would flow from the left ventricle and out of the heart through the aortic valve and into the aortic arch. In the event of a damaged mitral valve however, some blood can flow back into the left atrium. The pulmonary vein valve or valvular implant 1002 blocks this blood in the left atrium from retrograde flow into the pulmonary veins.

FIG. 10B illustrates the valve or valvular implant 1002 in an open configuration. For example, when the heart is in diastole, the oxygenated blood arriving from the lungs can enter the left atrium through the pulmonary veins. The membrane of the valve 1002 is in a relaxed configuration where it is spaced apart from the pulmonary veins so that blood can flow around it, or between the membrane and the atrium wall into the atrium. In this configuration, the blood vessels or pulmonary vein orifices are not blocked. Arrows 1003 indicate the direction of blood flow from the veins into the atrium. This valve or valvular implant improves cardiac output by enhancing forward flow and blocking regurgitation or retrograde blood from flowing back into the veins and other organs, such as the lungs (which reduces risk of pulmonary edema).

The valve or implant can be of varying sizes and positioned at various locations or heights within the atrium. In some exemplary embodiments, the implant comprises a membrane which can be positioned up against the top of the left atrium to block blood flow into the blood vessels, such as the pulmonary veins. In some exemplary embodiments, the components of the implanted device can extend all the way down to a native mitral valve, without impeding the flow of blood. The size of the implant in an exemplary embodiment can be configured to fit the anatomy of an atrium and/or veins feeding blood to the atrium, e.g., the left atrium and/or the pulmonary veins. For example, the exemplary embodiment illustrated in FIG. 34, described below, can have membranes ranging in size from approximately 3 cm to approximately 5 cm.

Figure 11A:
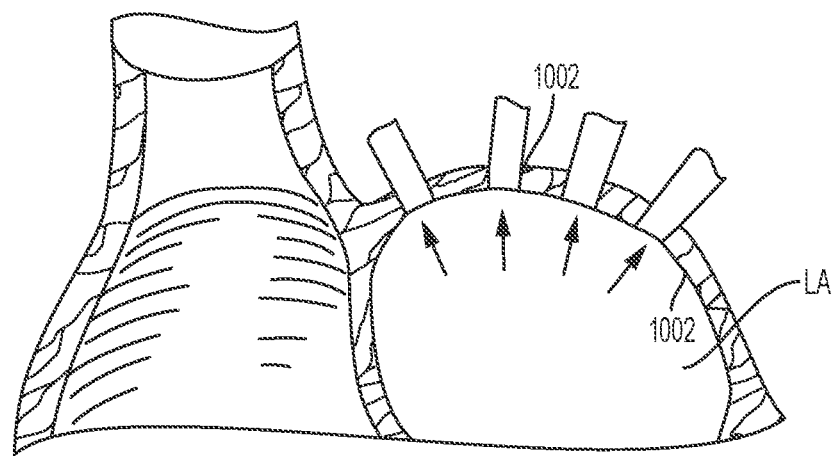
FIG. 11A illustrates a schematic view of a portion of a human heart with two exemplary valvular implants or devices each in a closed position.
Figure 11B:
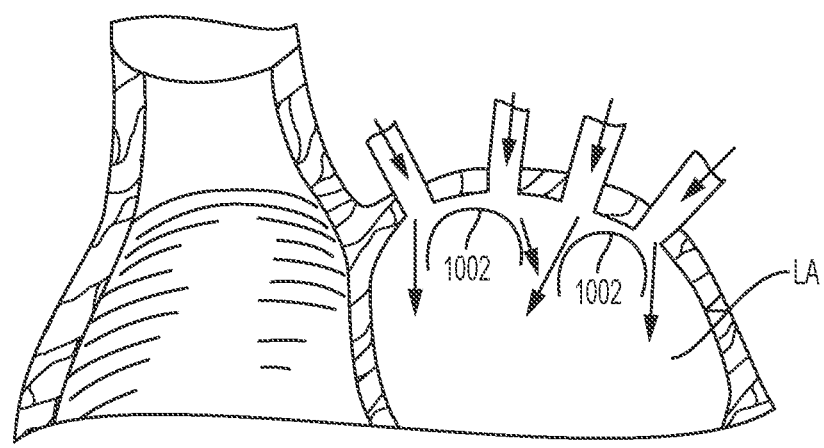
FIG. 11B illustrates a schematic view of a portion of a human heart with two exemplary valvular implants or devices each in an open position.

Referring to FIGS. 11A and 11B, an exemplary closure device/system or valvular implant/system 1002 is illustrated. In this embodiment, the system functions and can be constructed in a similar manner as in FIGS. 10A and 10B, but there are two valves or valvular implants 1002 (which can be entirely separate, unconnected implants or, in some embodiments, can be linked or attached in some way). A membrane of each valvular implant blocks different blood vessels, for example, each can block a set of two pulmonary vein orifices when in the closed configuration. In some embodiments, one membrane covers or is configured to cover the orifices of the pulmonary veins that come from the left lung, and the other membrane covers or is configured to cover the orifices of the pulmonary veins that come from the right lung. FIG. 11A is a schematic of when the membrane of each of the two valves or valvular implants 1002 are in a closed configuration. FIG. 11B illustrates the two membranes in an open configuration. The open configuration of FIG. 11B provides flow paths from the blood vessels or pulmonary veins to the heart or left atrium.

The embodiments described herein can also be implanted in a position to cover an opening to an appendage or aneurism, such as the left atrial appendage opening. The exemplary embodiments described herein can be deployed through a transapical method or through a transvascular method, such as a trans-septal method, e.g., through the venous side fossa and into a final position in the left atrium.

Figure 12A:
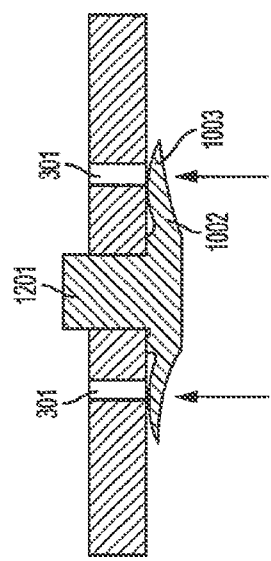
FIG. 12A illustrates an exemplary valvular implant or device in an open position.
Figure 12B:
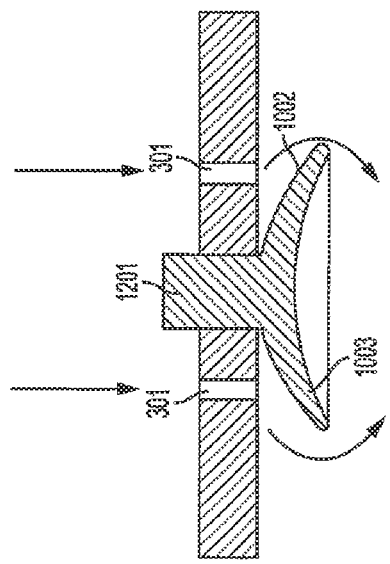
FIG. 12B illustrates an exemplary valvular implant or device in a closed position.

Referring to FIGS. 12A and 12B, a schematic of an exemplary embodiment of a valvular implant (which can be similar to a valvular implant as shown in FIGS. 10A-11B), such as a dome or an "umbrella" type unidirectional valve or valvular implant, is illustrated. FIG. 12A illustrates an open position and FIG. 12B illustrates a closed position. In FIG. 12A, an exemplary embodiment of a valve portion or sealing member 1003 (e.g., a membrane, etc.) of a valvular implant 1002 has a curved and/or dome shape so that it curves away from blood vessels 301. Stem 1201 is optional and the valvular implant can be secured into the heart or an atrium of the heart through other ways, such as a friction fit, or having anchors or barbs to attach to the heart or atrium wall. FIG. 12B illustrates a closed configuration of the valvular implant 1002 where the blood vessels 301, e.g., pulmonary veins, are blocked. In the closed configuration, blood cannot flow through the blood vessel orifices into the heart or from the heart back into the orifices or blood vessels.

Figure 13C:
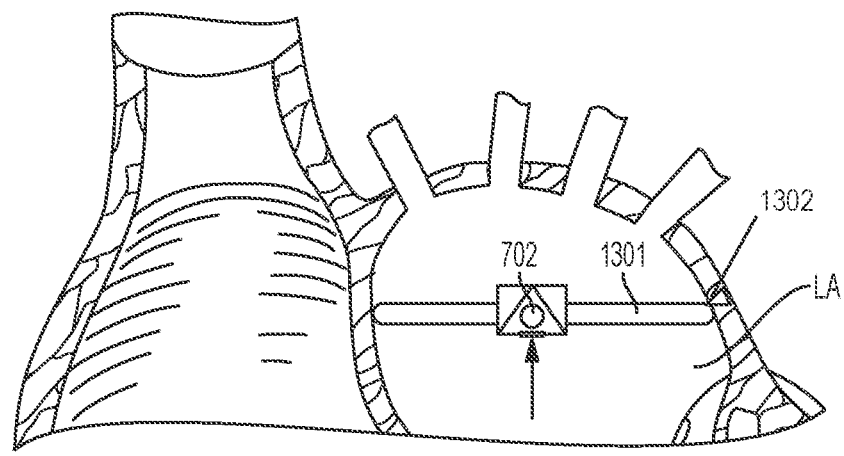
FIG. 13C illustrates a schematic of a portion of the human heart with the exemplary support and valve of FIG. 13A in a closed position.

Referring to FIGS. 13A through 13C, an embodiment of a valvular implant or device is illustrated. In the example illustrated by FIG. 13A, the device has an anchor or support 1301 with a valve or check valve 702 positioned in it. The anchor or support portion is positioned in the left atrium. In FIG. 13A, the valve 702 is in an open position so that blood can flow through the valve 702, such as from the venous blood vessels (e.g., pulmonary veins, IVC, SVC, etc.) into the heart or an atrium (e.g., a portion of the atrium) of the heart, and from there through a native valve (e.g., mitral valve, etc.) into a ventricle (e.g., left ventricle, etc.) of the heart. FIG. 13B is a sectional view of the anchor or support portion 1301, and the valve 702 positioned in the atrium taken along lines 13B-13B in FIG. 13A.

In FIG. 13C, the valve or check valve 702 is in a closed position. The pressure applied by the regurgitated blood, such as from the left ventricle through the mitral valve, closes the valve 702, and prevents blood from flowing in a retrograde manner into the blood vessels, e.g., pulmonary veins. The valve 702 and anchor or support 1301 are exemplary and can take the form of embodiments described with more particularity elsewhere herein.

The various blood vessel closure devices and valvular implants herein can be attached to a desired location in the heart by friction fit and/or with friction enhancing elements 1302, such as frame hooks, barbs, clips, adhesive, bonding, etc. These can also include anchors, anchoring portions, and/or include portions or regions that facilitate or promote tissue ingrowth to better secure them in a desired position/ location over time.

Figure 14:
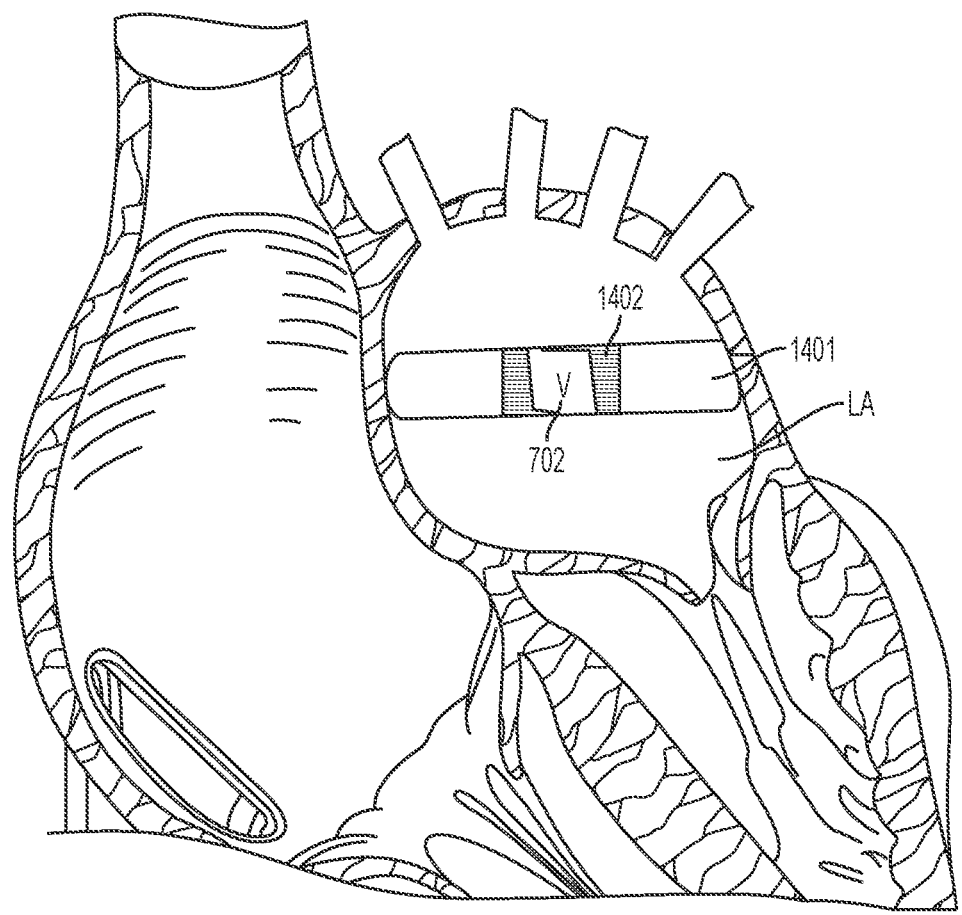
FIG. 14 illustrates a schematic of a portion of the human heart with a valve integrated with an exemplary docking device positioned in a left atrium of a human heart.
Figure 15:
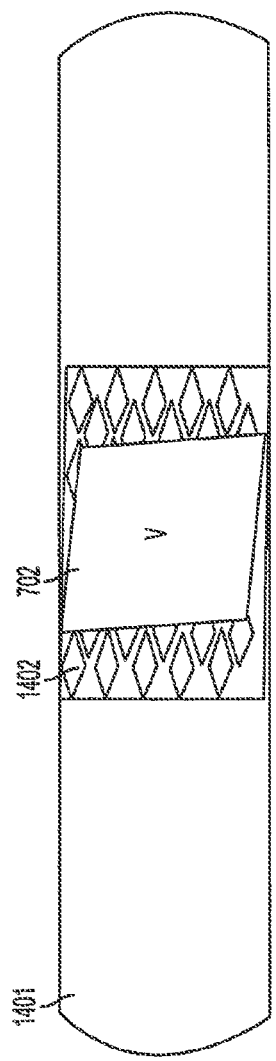
FIG. 15 illustrates a valve and exemplary docking device.

FIGS. 14 and 15 schematically illustrate an exemplary valvular implant, assembly or system. In this example, a separate anchor, support, or docking station 1401 has a docking portion or landing zone 1402 for a separate valve 702. In this example, the docking station 1401 is first deployed in the atrium and then a valve 702 is deployed in the docking portion, dock, or landing zone of the docking station 1401. In one embodiment of a similar assembly/ system, the valve 702 can be already assembled with and attached to the anchor or support 1401. The docking station valve is illustrated, for example, in FIG. 14 as being positioned in the left atrium at a level below the pulmonary vein orifices and above the mitral valve. An assembly or system having docking station 1401 and a valve 702 controls the bloodflow through the valve without needing to directly block the orifices of the blood vessel, e.g., pulmonary veins, etc. An enlarged schematic illustration of the docking station and valve is illustrated in FIG. 15. The docking station 1401 can be configured to maintain its position in the left atrium in a variety of ways, including, for example, by friction fit and/or with friction enhancing elements 1302, such as frame hooks, barbs, clips, adhesive, bonding, etc.

The valves 702 or any valves described as being docked in another anchor, support, dock, or docking station herein can be a variety of types of valves (e.g., a transcatheter prosthetic heart valve that is collapsible and expandable, such as Edwards Lifesciences SAPIEN 3 or CENTERA valves, etc.).

Figure 16B:
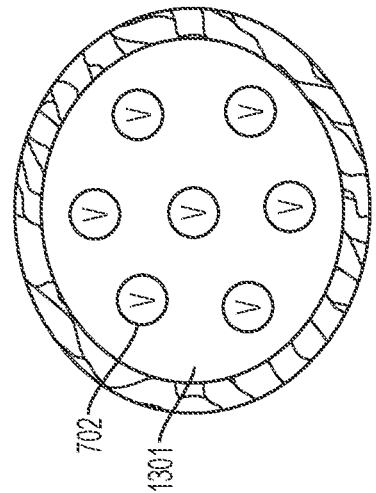
FIG. 16B is a plan view of the exemplary support and valves of FIG. 16A.
Figure 16A:
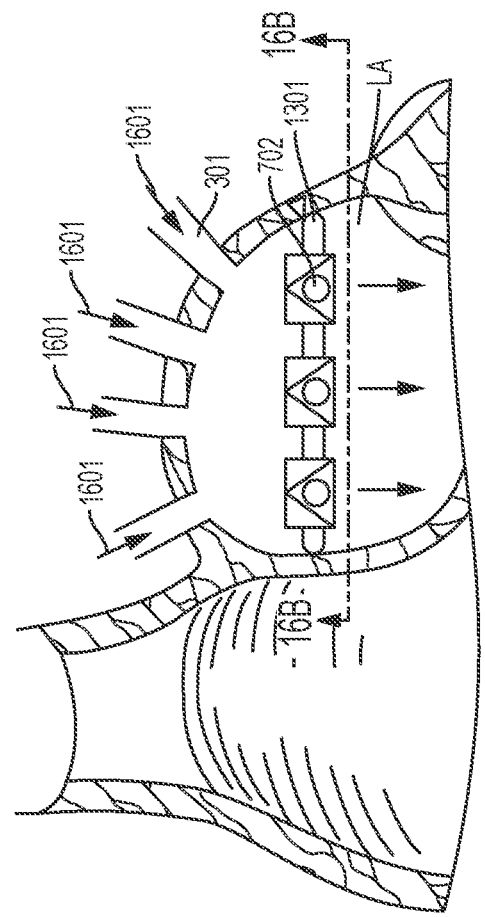
FIG. 16A illustrates a schematic of a portion of the human heart with an exemplary support (e.g., which can be ring-shaped and/or disc shaped) with a plurality of valves, such as check valves, in an open configuration.
Figure 16C:
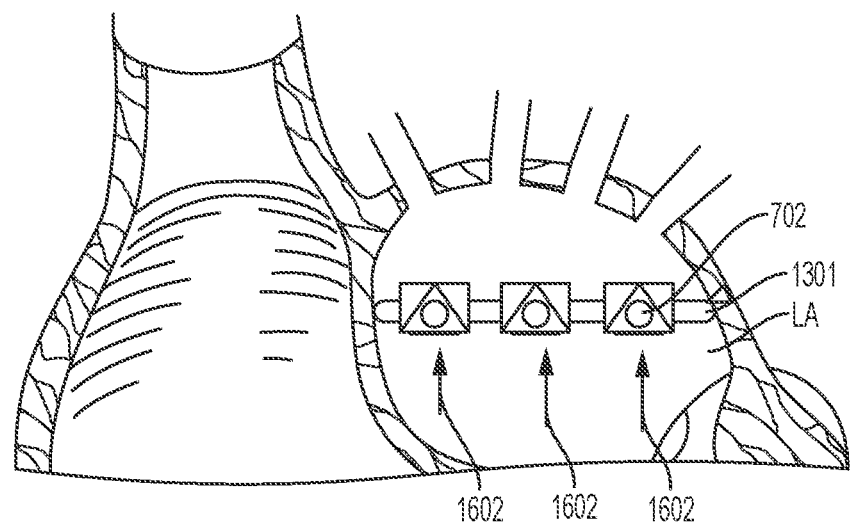
FIG. 16C illustrates a schematic of a portion of the human heart with the exemplary support with a plurality of valves of FIG. 16A in a closed configuration.

Regarding FIGS. 16A-16C, a schematic of an exemplary valvular implant or system having an anchor, docking station, or support with a plurality of valves is illustrated. As with the embodiment illustrated in FIGS. 13A-13C, blood flowing from the blood vessels, such as pulmonary veins, into the upper portion of the heart (e.g., left or right atrium) can flow through the open valves or check valves 702 and into the lower portion of the heart or atrium, and from there into another chamber of the heart, such as the left or right ventricle, when the check valves 702 are in an open position. The valves 702 can be in the open position when the heart is in diastole, such that the open check valves permit blood flowing (indicated by arrows 1601) from the blood vessels 301 through the atrium to reach and pass the mitral valve or tricuspid valve. FIG. 16B is a sectional view taken along lines 16B-16B showing the anchor or support 1301 and valves 702 positioned in the atrium.

FIG. 16C illustrates the anchor schematic of FIGS. 16A and 16B when the valves 702 are in the closed position. The closed position occurs when the heart is in systole. For example, when the left ventricle contracts in a heart with a deficient mitral valve, the blood flow that re-enters to the left atrium (indicated by arrows 1602) pushes against the valves 702 such that they are in a closed position and blood cannot flow back into the upper portion of the left atrium.

Figure 16E:
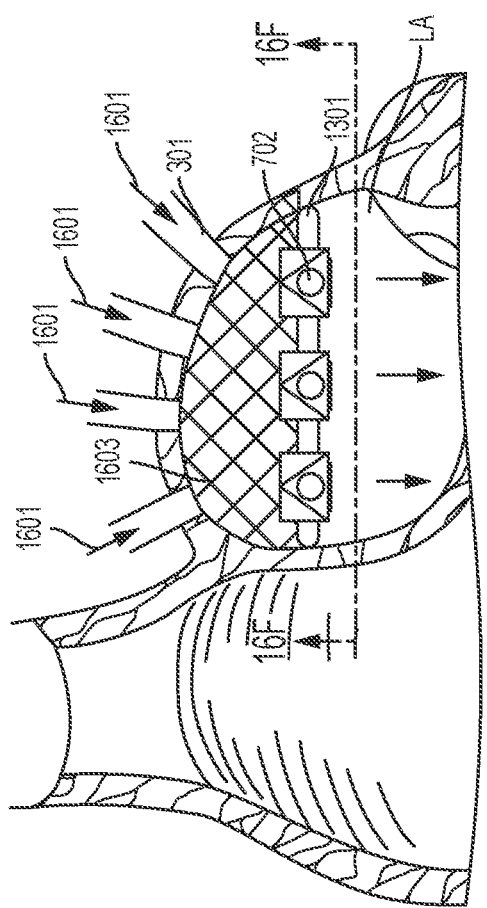
FIG. 16E illustrates a schematic of a portion of the exemplary hemispherical support of FIG. 16D with a plurality of valves or check valves.
Figure 16F:
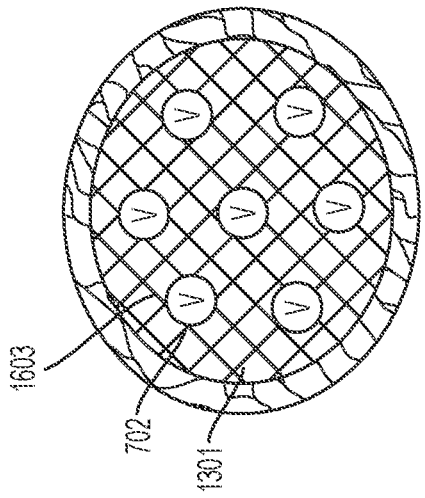
FIG. 16F is a view taken along lines 16F-16F in FIG. 16E.
Figure 16D:
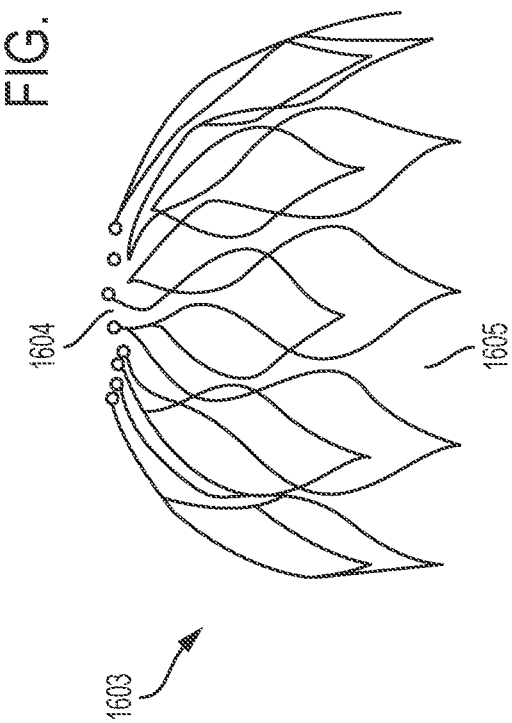
FIG. 16D illustrates an exemplary embodiment of an exemplary hemispherical support component of a valvular implant or system.

FIG. 16D illustrates an exemplary hemispherical dome-shaped or umbrella-shaped support portion 1603, which can be an integral part of the docking station/anchor 1301 or a separate component coupled or otherwise attached to the docking station/anchor 1301. The dome or support portion 1603 can have a stent-like structure and can have struts similar to those commonly used in stents. The dome/support 1603 can optionally have an opening at the top 1604 and can be open at the bottom 1605. In the illustrated embodiment, the dome/support 1603 is uncovered, such that blood can flow through the openings of all of the cells of the stent-like structure. In another embodiment, portions of the dome 1603 (e.g., such as those that do not cover the pulmonary veins) can be covered with a material or membrane, such as a fabric, cover, or tissue, such as pericardial tissue.

FIGS. 16E and 16F illustrate a schematic of an exemplary dome or dome-shaped support 1603 with the plurality of valves of FIGS. 16A-C deployed in an atrium. In this embodiment, the dome/support 1603 occupies the upper portion of the atrium to hold the valves 702 in position in the atrium. FIG. 16F is a sectional view taken along line 16-F-16F in FIG. 16E, (viewed from below the anchor 1301 looking upward, the dome shaped support 1603 and valves 702. The embodiment illustrated by FIGS. 16E and 16F can include the support portion 1301 or another structure to block the flow of blood around the valves 702. As such, the device illustrated by FIGS. 16E and 16F operates in substantially the same manner as the device illustrated by FIGS. 16A-16C.

Figure 17B:
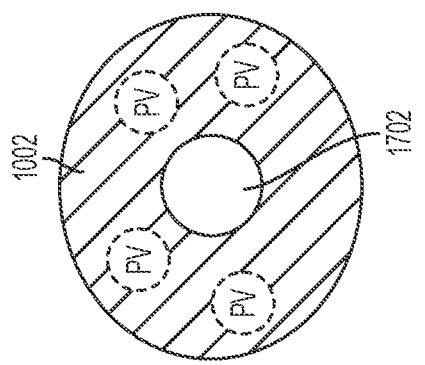
FIG. 17B is a view taken along lines 17B-17B in Figure A.
Figure 17A:
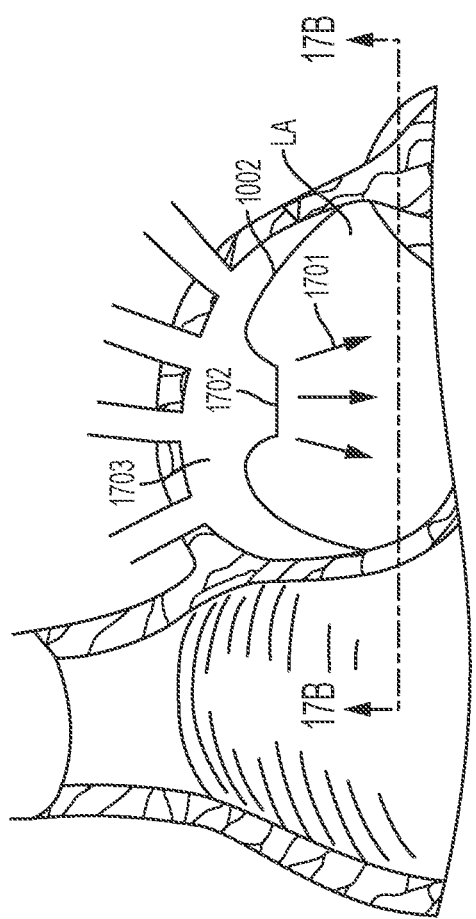
FIG. 17A illustrates a schematic of a portion of the human heart with an exemplary valvular implant or device with a central opening in an open configuration.

FIGS. 17A-D illustrate a schematic of an exemplary closure device/system or valvular implant/system providing unidirectional flow. In FIG. 17A, the implant is in an open configuration. In the open configuration, the implant allows blood to flow through the implant as indicated by the unidirectional arrows 1701. In this embodiment, the implant can have a dome, umbrella, or semi-sphere shape, or a shape that resembles a dome, umbrella, or semi-sphere. The implant can be tented against the left atrium wall. Also in this embodiment, the implant has a valve portion, which is depicted in these figures as membrane 1002. The implant can have one or multiple valve portions or membranes covering some or all of the implant and can have an outflow opening 1702 in the center of the implant membrane(s). FIG. 17B is a view taken along lines 17B-17B in FIG. 17A of FIG. 17A, and shows the relative positions of pulmonary veins PV in relation to the outflow opening 1702 of the membrane. The valve portion or membrane 1002 of the implant moves up and down in the atrium, based on whether the heart is in systole or diastole. In diastole, the membrane can be in the open configuration of FIG. 17A, and blood can flow through the centrally located outflow opening 1702.

Figure 17D:
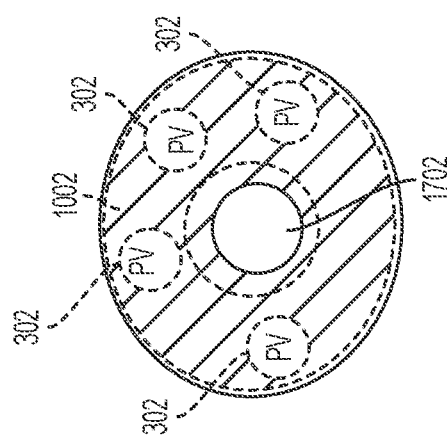
FIG. 17D is a view taken along lines 17D-17D in FIG. 17C.
Figure 17C:
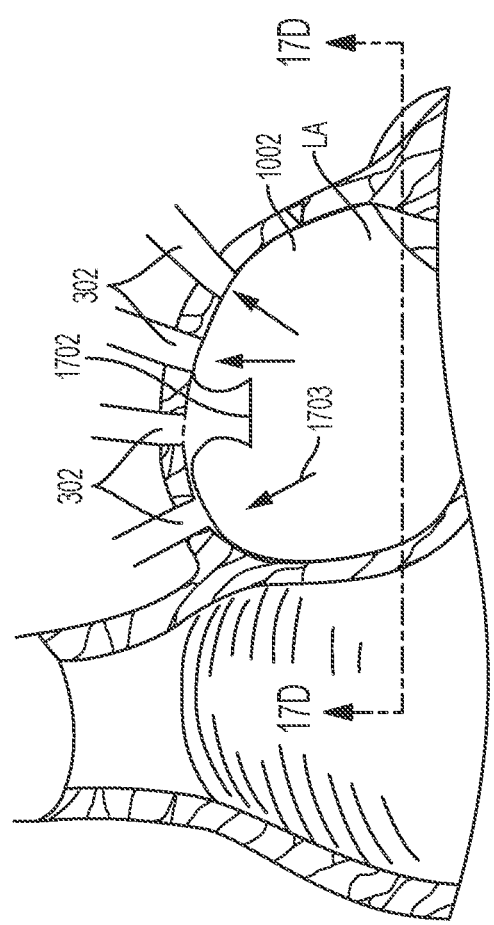
FIG. 17C illustrates a schematic of a portion of the human heart with the valvular implant or device of FIG. 17A in a closed configuration.

In systole, the valve portion or membrane can be in the closed configuration shown in FIGS. 17C and 17D to prevent or inhibit retrograde flow of blood. In FIG. 17C, the membrane is shown, for example, in contact with the upper surface of the left atrium, such that the pulmonary vein orifices 302 are all blocked by the membrane 1002. In this configuration, blood cannot flow from the left atrium back into the pulmonary veins by the pressure of any regurgitant blood. The arrows 1703 indicate the membrane 1002 is pushed against the left atrium wall. FIG. 17D is a view taken along lines 17D-17D of FIG. 17C, and in particular illustrates the closing off of the pulmonary vein orifices. In the closed configuration, no blood can flow into the pulmonary veins through the opening 1702 of the membrane.

Figure 17E:
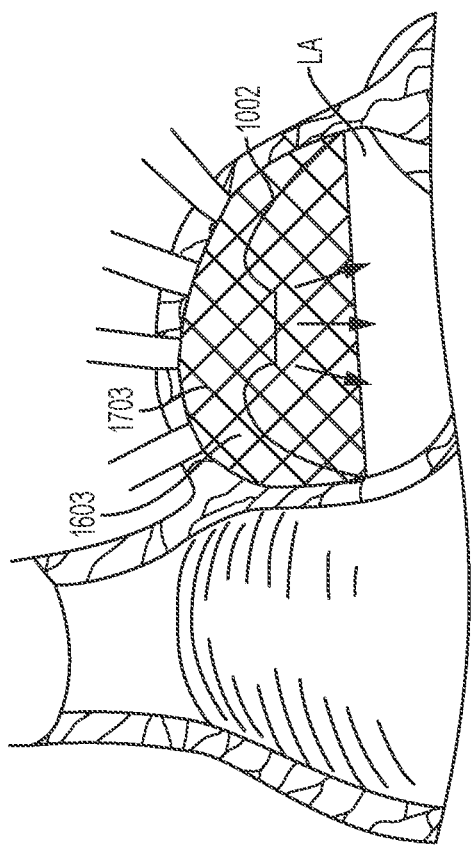
FIG. 17E illustrates a schematic of a portion of the human heart with the exemplary valvular implant or device of FIG. 17A combined with the exemplary hemispherical support of FIG. 16D.

FIG. 17E illustrates a schematic of an implant that is similar to the embodiment illustrated by FIG. 17C with the addition of a hemispherical dome/support 1603 that can have a stent like configuration. The dome/support can be the same as or similar to that illustrated in FIG. 16D or another similar configuration. The dome/support 1603 properly positions the membrane 1002 in the left atrium. As such, the device illustrated by FIG. 17E operates in substantially the same manner as the device illustrated by FIGS. 17A-17D.

Figure 18A:
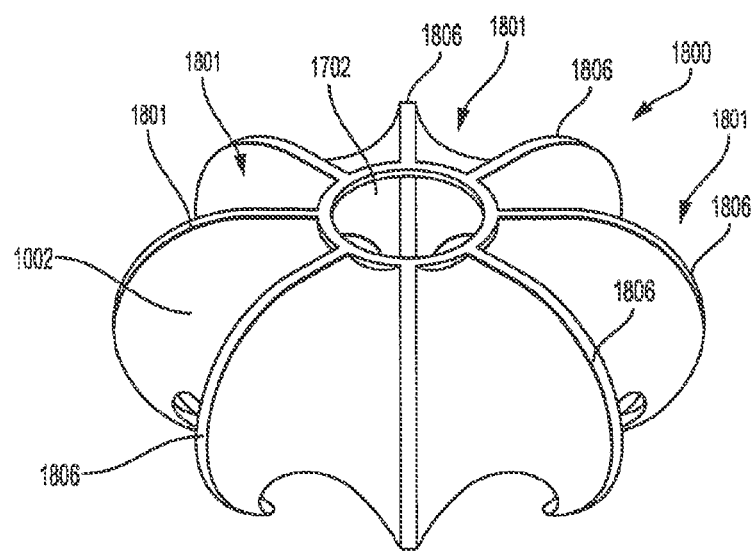
FIG. 18A illustrates an exemplary valvular implant or device in an open configuration.
Figure 18B:
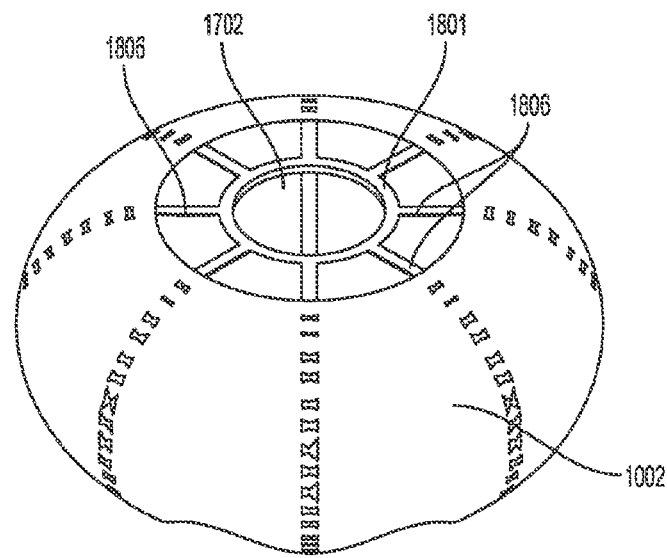
FIG. 18B illustrates an exemplary valvular implant or device in a closed configuration (i.e., a configuration that closes blood vessel openings).

FIGS. 18A and 18B illustrate an exemplary closure device/system or valvular implant/system that has a frame 1801 and one or more valve portions configured as a membrane 1002 (or multiple membranes) attached to the frame. The frame 1801 (and other frames described elsewhere herein) can comprise Nitinol, steel, plastic, resilient material, and/or other flexible material that can expand from a compressed condition (e.g., sufficient for transvascular or transfemoral delivery to the heart with a delivery catheter) to an expanded or deployed condition. The frame has a membrane 1002 attached to it. The membrane can be made of pericardium, ePTFE, PET, and/or another biocompatible material. The membrane can be treated and/or coated with chemicals, drugs, etc. to prevent or inhibit calcification and/or tissue ingrowth into the membrane. The membrane can be secured to the frame 1801 by suturing, electrospinning, or other lamination processes. In FIG. 18A the implant 1800 is in an open configuration, and the blood can flow through the gaps created between the outside of the membrane 1002 and the heart wall or atrial wall, where each opening for bloodflow is defined by gaps between struts 1806 of the frame 1801. Blood can also flow through the center opening 1702. Though, the center opening is optional.

In FIG. 18B, the closed configuration is illustrated. In the closed configuration, the membrane is expanded outward to create a convex surface to abut against the atrial wall, and block blood vessel orifices, e.g., the pulmonary vein orifices, etc.

Figure 19A:
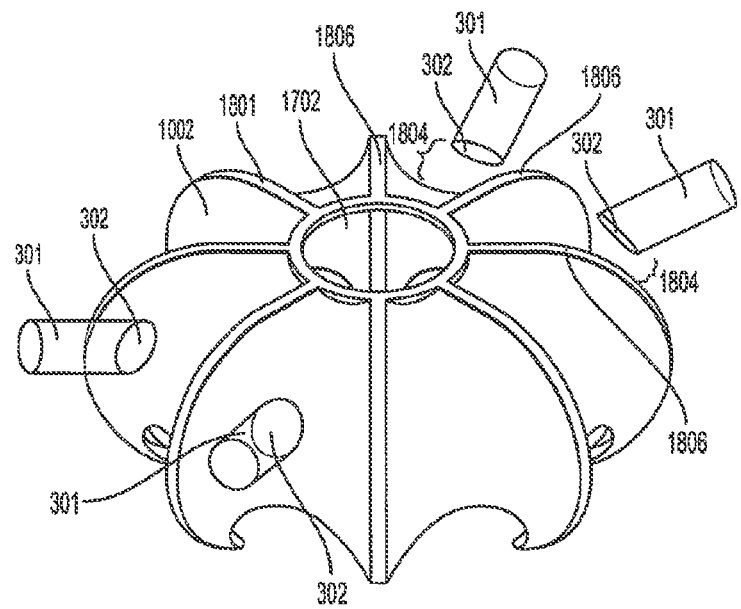
FIG. 19A illustrates an exemplary valvular implant or device configured as a pulmonary vein valve implant or device, shown in an open configuration in relation to pulmonary vein orifices.
Figure 19B:
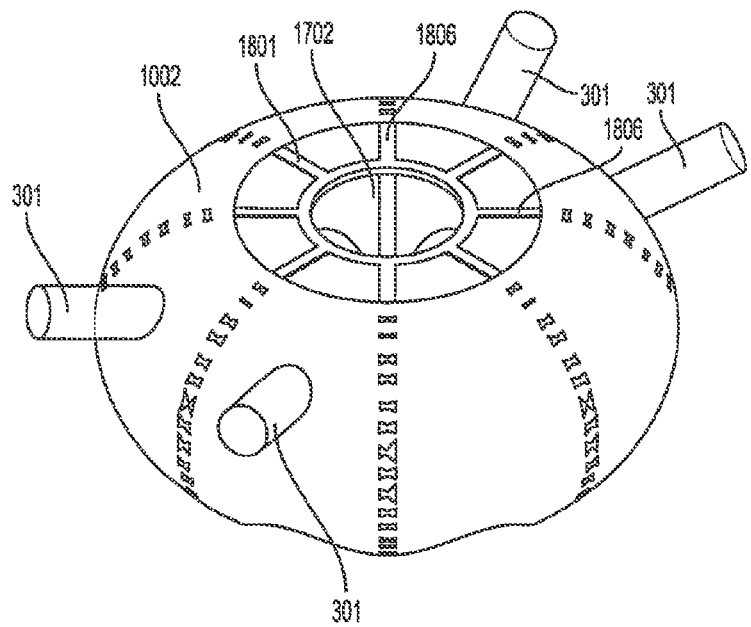
FIG. 19B illustrates the exemplary valvular implant or device of FIG. 19A in a closed configuration in relation to pulmonary vein orifices (i.e., a configuration that closes the pulmonary vein orifices or openings).
Figure 20A:
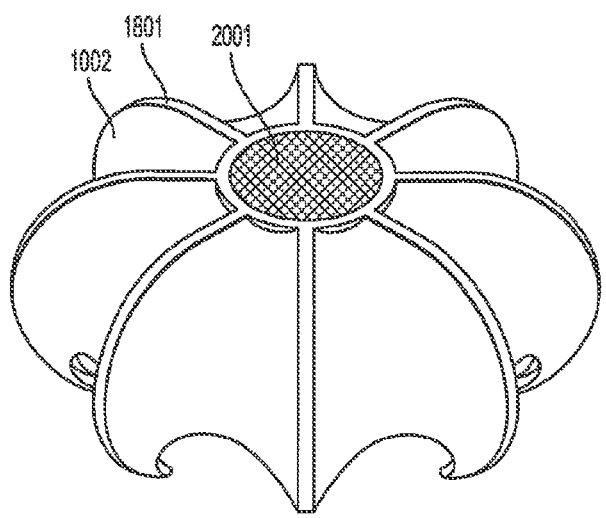
FIG. 20A illustrates an exemplary valvular implant or device in an open configuration.
Figure 20B:
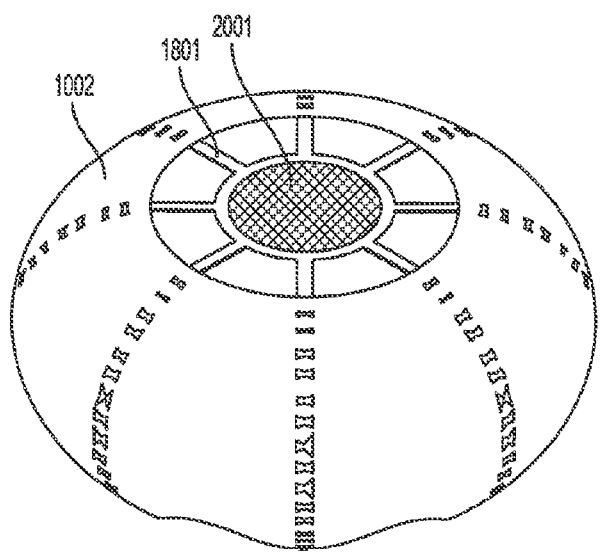
FIG. 20B illustrates the exemplary valvular implant or device of FIG. 20A in a closed configuration (i.e., a configuration that closes blood vessel openings).

FIGS. 19A and 19B illustrate the exemplary closure device/system or valvular implant/system as shown in FIGS. 18A-18B, with the addition of pulmonary veins 301 to the illustration. In the open configuration, each section of the membrane 1002 is in a concave position, so that the orifices of the pulmonary veins are not blocked by the membrane. There is a gap 1804 in between each pulmonary vein orifice 302 and the membrane 1002. In the blocked flow configuration of FIG. 19B, however, the membrane blocks the orifices of the pulmonary veins and there is no gap between the orifices and the membrane. The membrane blocking the pulmonary veins prevents blood from flowing into the pulmonary veins.

Figure 21A:
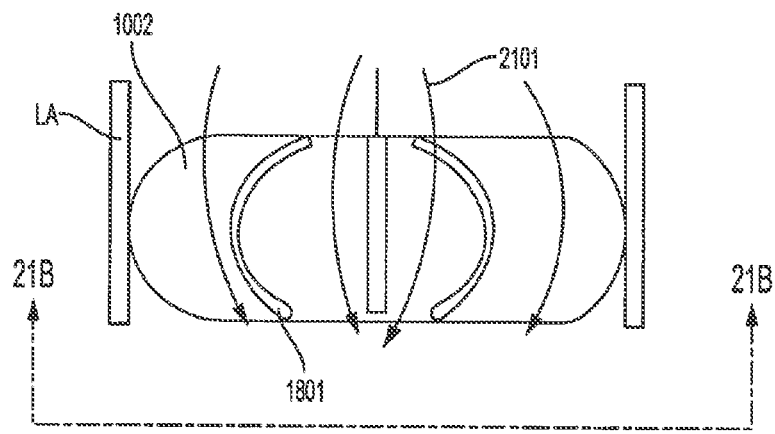
FIG. 21A illustrates a cross-sectional view of an exemplary valvular implant or device in an open configuration positioned between heart chamber walls.
Figure 21B:
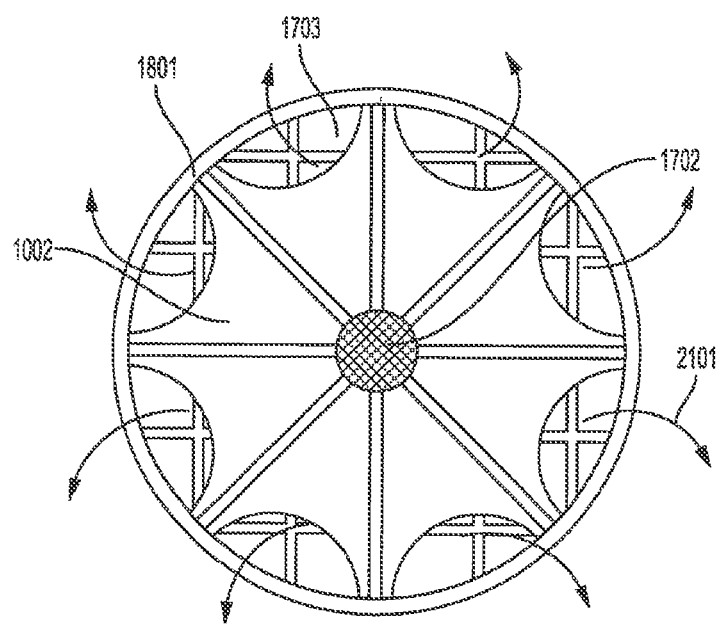
FIG. 21B is a view taken along lines 21B-21B in FIG. 21A.
Figure 21C:
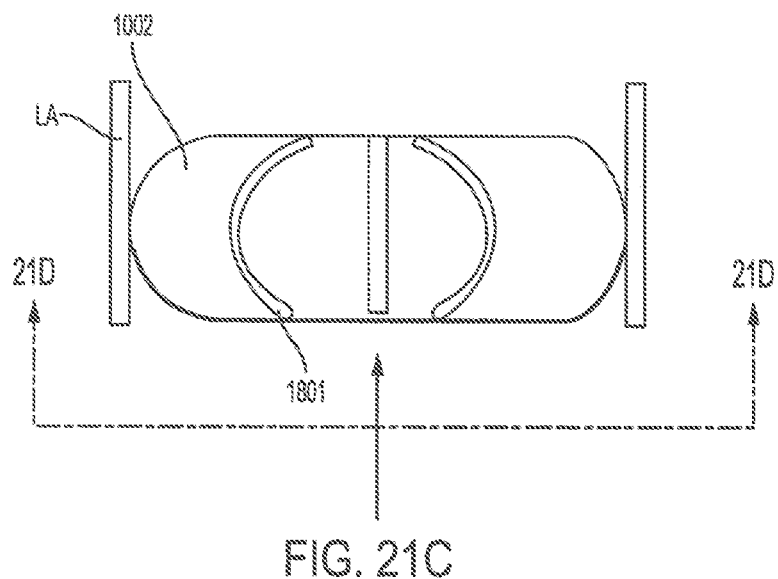
FIG. 21C is a sectional view of an exemplary valvular implant or device in a closed position positioned between heart chamber walls.

FIGS. 20A, 20B and 21A, and 21B illustrate an exemplary closure or valvular implant or system similar to those shown in FIGS. 18A and 18B, but there is no central opening. Instead, the center 2001 is covered. FIGS. 21A and B illustrate an open configuration of the unidirectional valvular implant. FIGS. 21C and D illustrate a closed configuration of the same embodiment. A valve portion or membrane 1002 and frame 1801 permit only unidirectional blood flow when implanted in an atrium, such as the left atrium. In FIG. 21B, the blood flowing in (represented by arrows 2101) from the blood vessels or pulmonary veins can pass through the implant gaps, exposing flow paths between the membrane and the atrium for the blood to flow past. FIG. 21B is a view taken from lines A-A in FIG. 21A, and illustrates the gaps between the membrane and the atrial walls when the valve device is open, such as when the heart is in diastole.

Figure 21D:
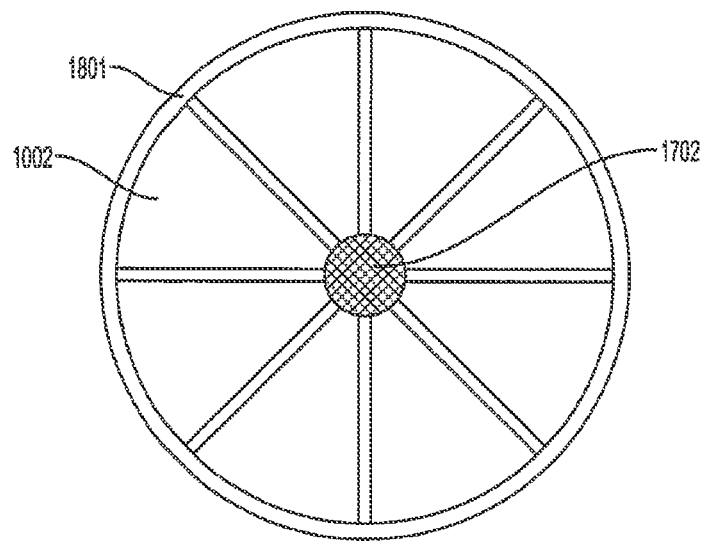
FIG. 21D is a view taken along lines 21D-21D in FIG. 21C.

In FIG. 21D, the implant is in a closed configuration when the heart is in systole, and there is no blood flow, even if there is valve regurgitation. The closed configuration occurs when the membrane is approximated to the atrium wall to block the flow of blood back into the blood vessels, for example, when approximated to the left atrium wall to block the flow of blood to the pulmonary veins. FIG. 21D illustrates the implant as viewed along lines C-C in FIG. 21C.

Figure 22:
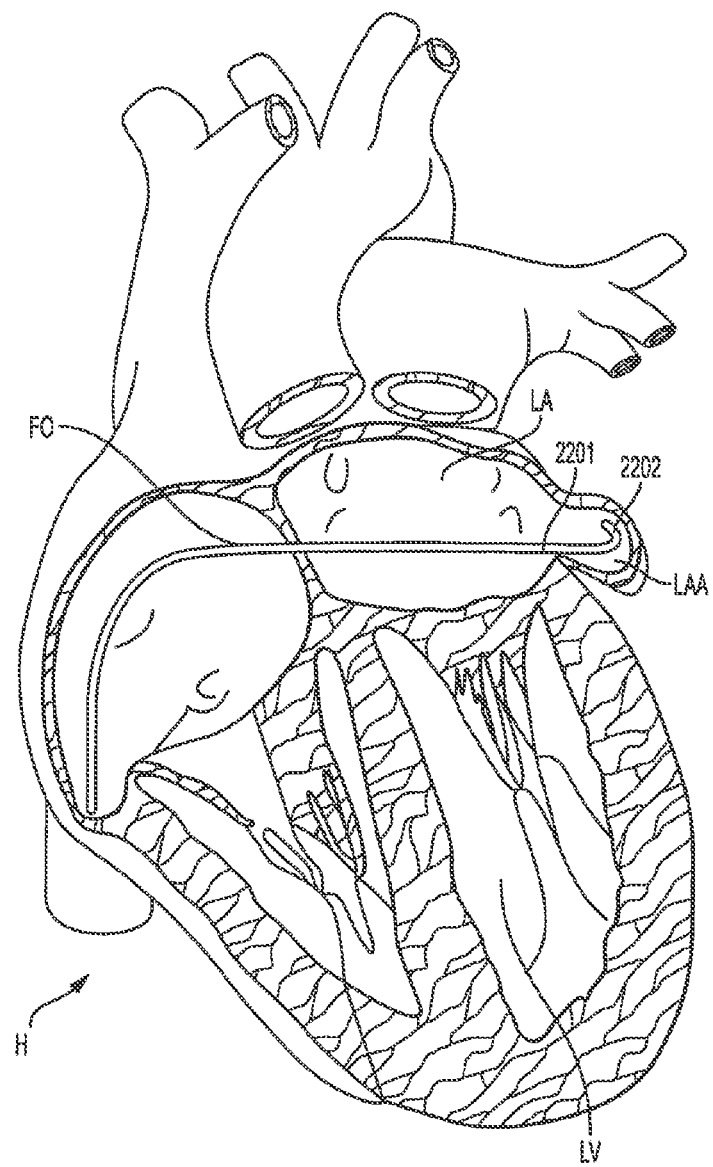
FIG. 22 illustrates a schematic of an exemplary delivery device or system useable to deliver a valvular implant or device, positioned in at least partially in the left atrium.
Figure 23:
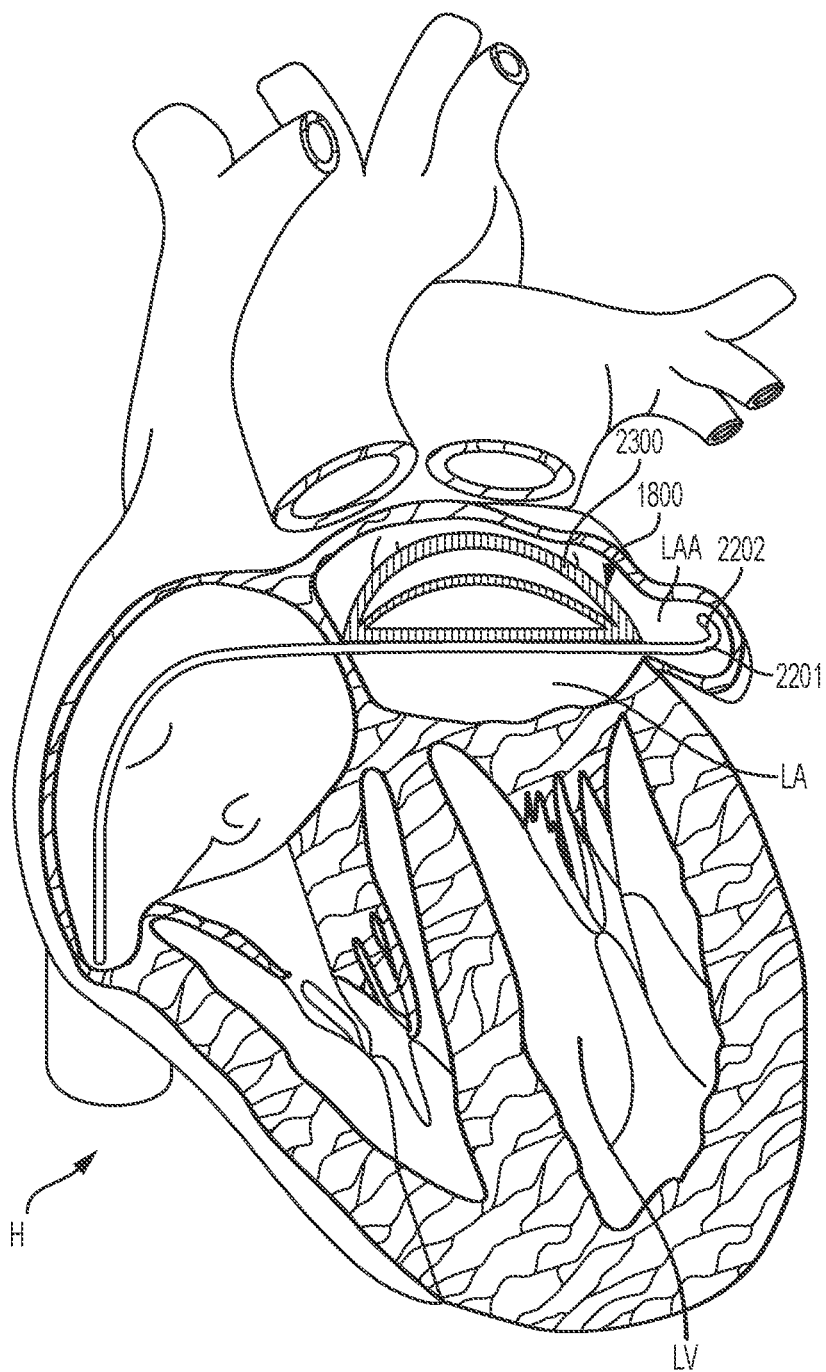
FIG. 23 illustrates a schematic of any of an exemplary valvular implant or device being deployed in the left atrium.

The various systems and implants disclosed herein can be delivered with a transvascular and/or trans-septal approach through the fossa ovalis (FO). The right atrium is approached transvascularly or transfemorally. If being deployed in the right atrium, the system or implant can be deployed when the right atrium is reached. If being deployed in the left atrium, a trans-septal puncture, such as through the FO is made. In one embodiment, a guidewire 2201 is inserted into the heart H, and positioned in the LAA as illustrated in FIG. 22, or in one of the pulmonary veins. An implantable system or implant can be advanced over the guidewire into the left atrium. FIG. 22 illustrates a guidewire 2201 in the heart H, which is positioned to cross the left atrium from the fossa ovalis to the left atrial appendage (LAA), where a distal end 2202 of the guidewire is in the LAA. FIG. 23 illustrates a schematic of the closure device or valvular implant 1800, having a resilient structural frame 2300, being deployed. The implantable system has been advanced over the guidewire and into the left atrium. The positioning of the guide wire helps to stabilize and locate the position of the system, because the FO and LAA are identifiable landmarks in the heart anatomy. The implant is then deployed into position. The deployment can be done using a balloon to expand the implant until it attaches to the left atrium wall and/or the implant can be self-expanding and/or mechanically expandable.

Figure 23A:
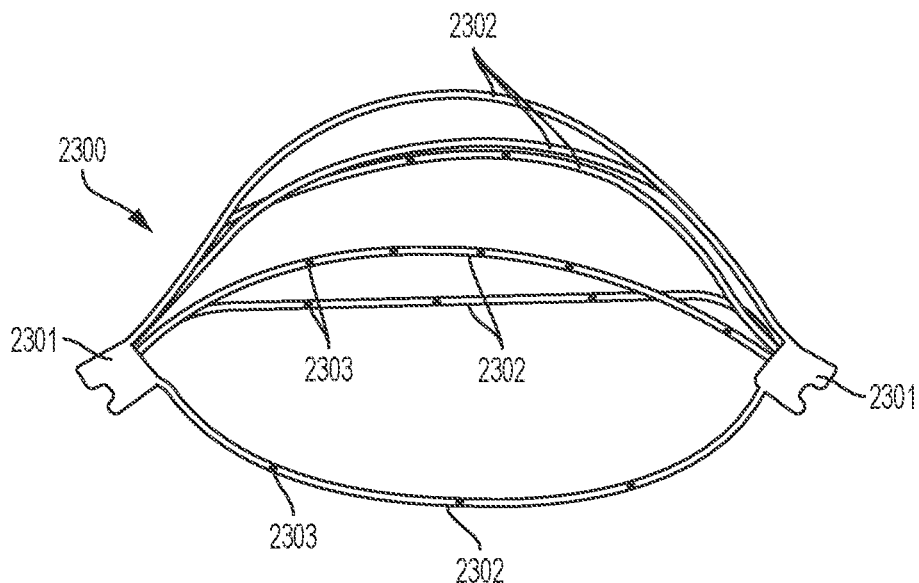
FIG. 23A illustrates a side view of an exemplary support frame.
Figure 23B:
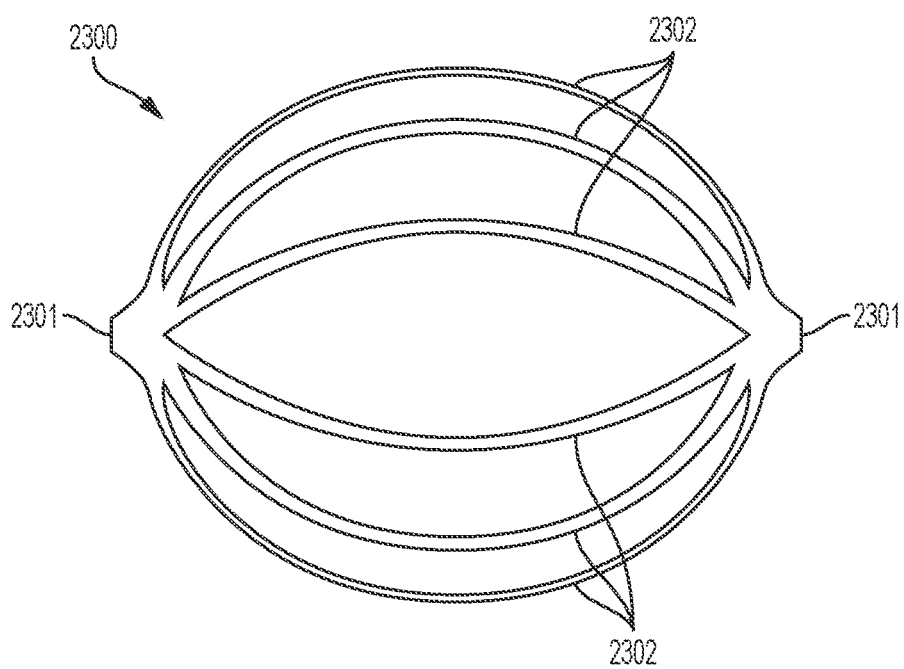
FIG. 23B illustrates a top plan view of the support frame of FIG. 23B.

FIGS. 23A and 23B illustrate alternative views of a resilient structural frame 2300 of FIG. 23. FIG. 23A illustrates a side perspective view of the frame 2300, and FIG. 23B illustrates a top plane view of the frame 2300. The frame 2300 can have two ends 2301, where the 2302 of the frame are gathered and/or connected together. Ends 2301 can be circular or cylindrical or any other shape that permits attachment of the frame 2300 to a deployment tool. Openings 2303 can be provided to allow one or more valve portions and/or membranes to be attached to the struts. The valve portions or membrane(s) can span the openings as will be described in more detail below or cover select portions of the frame and/or openings.

FIGS. 23C and 23D illustrate exemplary embodiments of membrane 2304 attached to the frame 2300. In FIG. 23D, two membranes 2304 are attached to the frame 2300 and can be attached to the struts 2302. Each membrane can cover a portion of the exterior of the dome-shaped frame such that there is a gap 2305 in between the membranes. The gap 2305 allows blood to flow from the upper portion of the atrium to the lower portion of the atrium when the implant 1800 is in the open configuration. The membranes can be configured to cover one, some, or all of the blood vessels (e.g., pulmonary veins PV) when in the closed configuration to prevent bloodflow.

In FIG. 23D, membrane 2304 is attached to the struts 2302 of the frame 2300. The membrane can be a single membrane attached to the frame as illustrated (or can be multiple membranes), and can have at least one opening 2306 to permit blood to flow through from one side of the membrane to the other side of the membrane, when the device 1800 is positioned in the heart, e.g., in the left atrium, and is in the open position. When implanted, the membrane is aligned so that the solid portions of the membrane cover one or more of the blood vessels or pulmonary veins PV. As such, the membrane prevents bloodflow in the closed position.

Figure 23E:
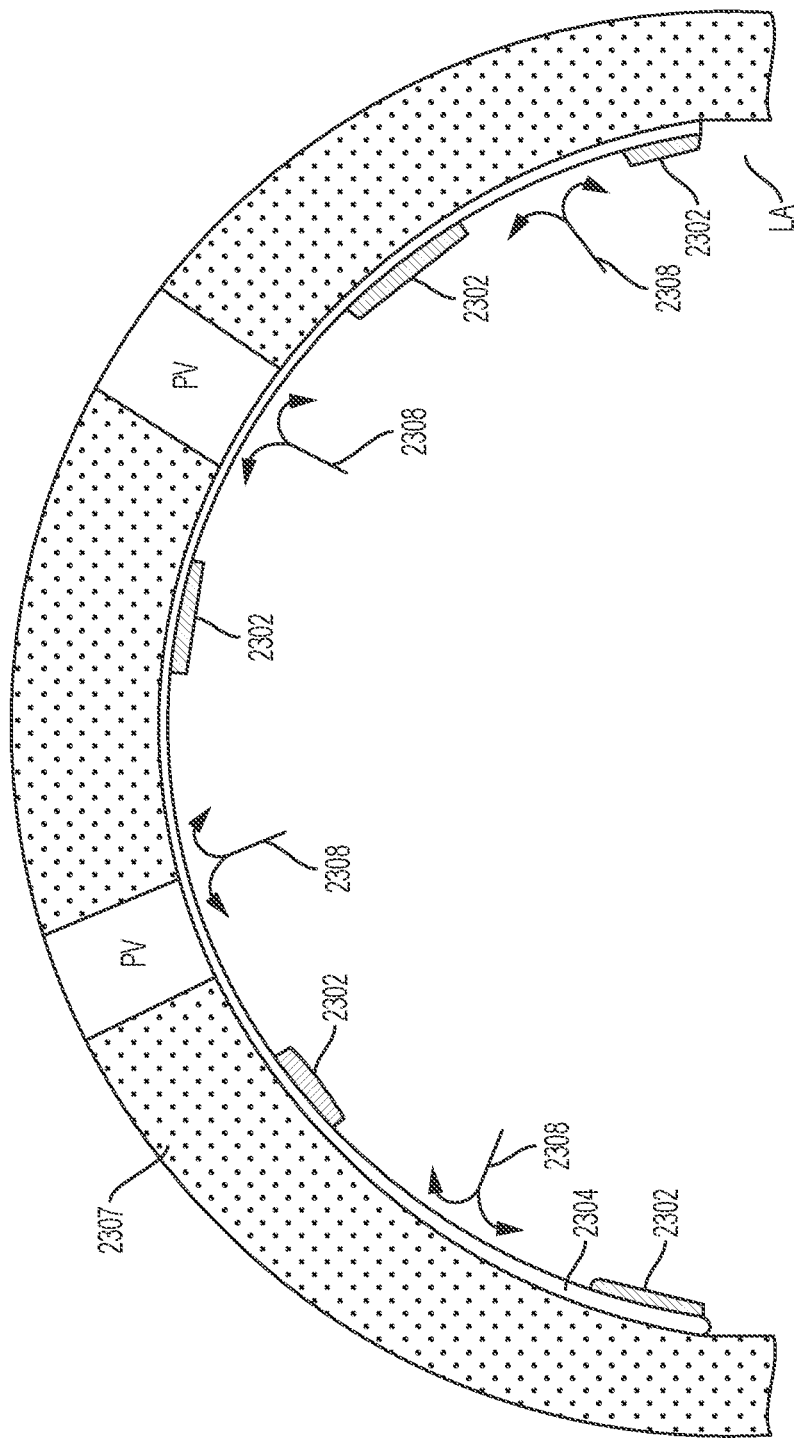
FIG. 23E illustrates a schematic of the device of FIG. 23D taken from cross-section line 23E-23E, in a closed configuration in a left atrium of a human heart.
Figure 23F:
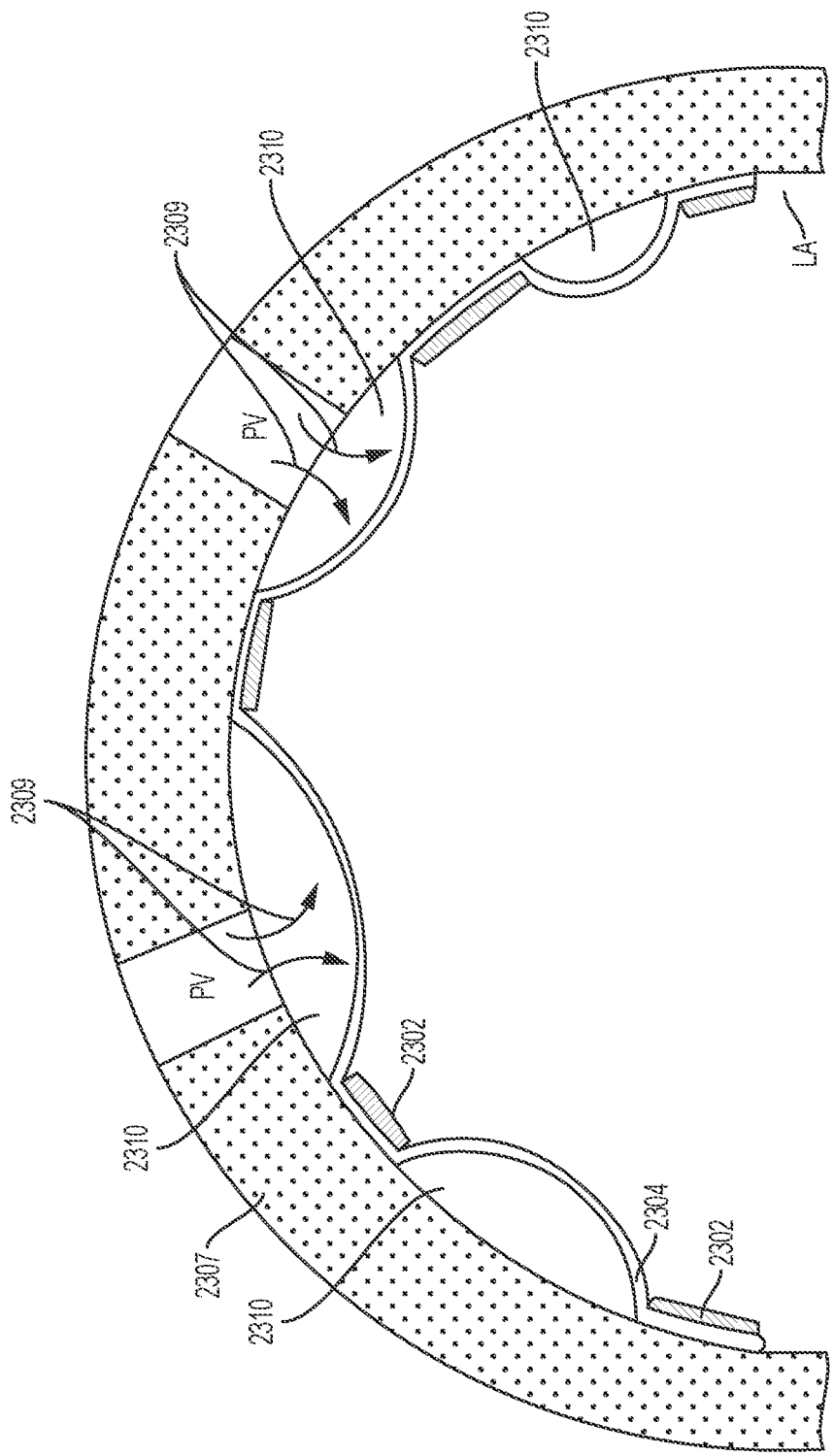
FIG. 23F illustrates a schematic of the device of FIG. 23D taken from cross-section line 23E-23E, in an open configuration on the left atrium of the heart.
Figure 24:
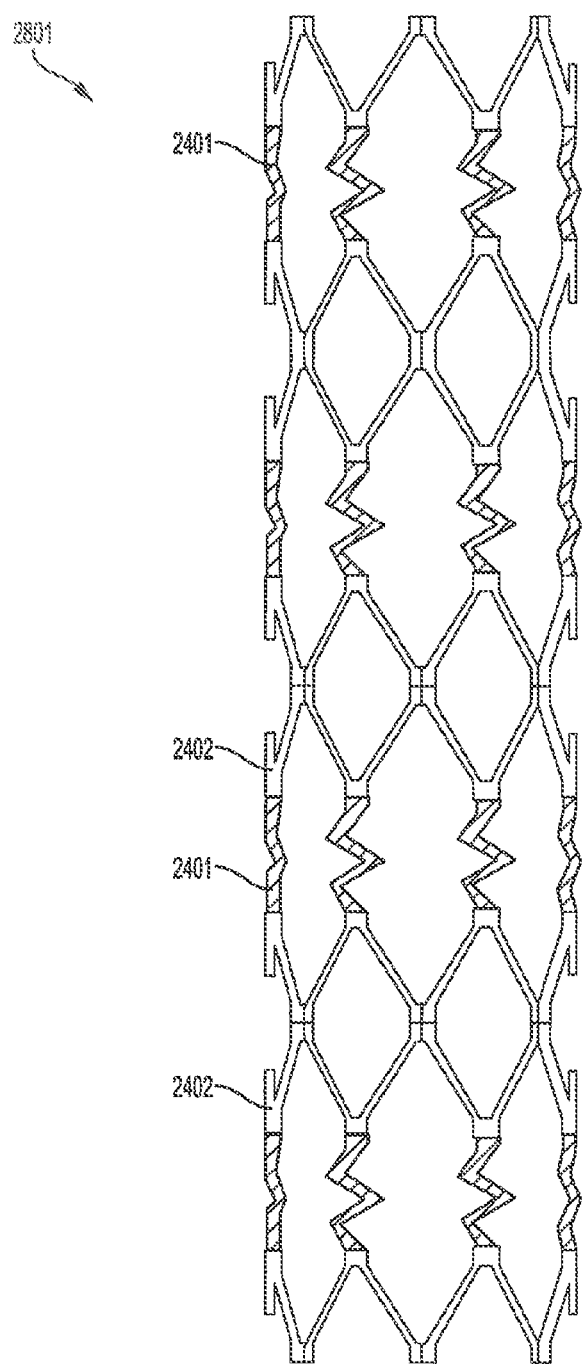
FIG. 24 illustrates a side view of an exemplary anchor or anchoring frame.

FIGS. 23E and 23F are sectional views taken along lines 23E-23E in FIGS. 23C and 23D. These cross-sectional views illustrate operation of each of the devices of FIGS. 23C and 23D. In FIG. 23E, the implant 1800 is in a closed configuration. Arrows 2308 indicate that regurgitant blood flow that would otherwise regurgitate into the blood vessels or pulmonary veins, is blocked by the membrane 2304. The bloodflow is blocked, because in the closed configuration, the pressure of the regurgitant blood flow pushes the membrane against the heart wall or left atrium wall 2307. In FIG. 23F, the implant 1800 is in an open configuration, and the blood flow is entering the left atrium from the blood vessels or pulmonary veins as indicated by arrows 2309. In the open configuration, struts 2302 position the membrane against the heart wall or left atrial wall 2307. Pressure from the incoming bloodflow causes portions of the membrane 2304 to be pushed inward, which creates a space 2310 for blood to enter above the membrane, prior to flowing through a gap (Reference Character 2305 in FIG. 23C) or opening (Reference Character 2306 in FIG. 23D) in the membrane into the lower portion of the chamber of the heart, e.g., of the left atrium or right atrium.

The system or implant 1800 can have a configuration of any of the embodiments described herein; the implant 1800 is intended as a generic depiction of any of the embodiments disclosed herein. The implant can be delivered transeptally, transapically, transatrially, through a trans-aortic technique, or other delivery methods.

The system or implant 1800 can also be designed to close an aneurism or appendage in a heart such as, for example, a left atrial appendage LAA. For example, in an embodiment where the LAA is to be closed from the left atrium, the portion of the membrane of the implant that is around the LAA can be designed to remain closed and function as a LAA closure. For example, struts can be placed around the LAA, or the membrane can be of a stiffer material in this region than elsewhere in the implant, so that the device permanently seals off the LAA.

Various features of the exemplary embodiments described herein include various frame shapes, such as a sphere, semi-sphere, dome, toroid, disc or other shape that conforms to the LAA. The devices are illustrated as circular; however, in actual practice, the devices can be contoured to match the shape of the atrial walls. The frame can be made of Nitinol, stainless steel, MP35, and/or other metals.

Referring to FIGS. 24-27, in one exemplary embodiment the anchors or anchoring frames 2801 of the embodiments illustrated in FIGS. 28-33, include springs or spring/flexible segments 2401 to allow anchors 2801 to bend. The frames 2801 are resilient. The spring/flexible segments 2401 allow the stent segments to anchor on the walls of the blood vessel while enabling the docking station to curve if needed. In the example illustrated by FIG. 24, frame or stent segments 2402 are attached to each other by multiple springs or spring/flexible segments 2401. Any of the anchors or anchoring frames shown and described herein can optionally have any combination of spring/flexible segments 2402 and frame or stent segments 2401. The spring/flexible segments 2402 can take a wide variety of different forms. Examples of spring/flexible segments 2402 include, but are not limited to, spring wires, springs constructed by selective removal of material compression springs, torsion springs, and/or tension springs.

Figure 25:
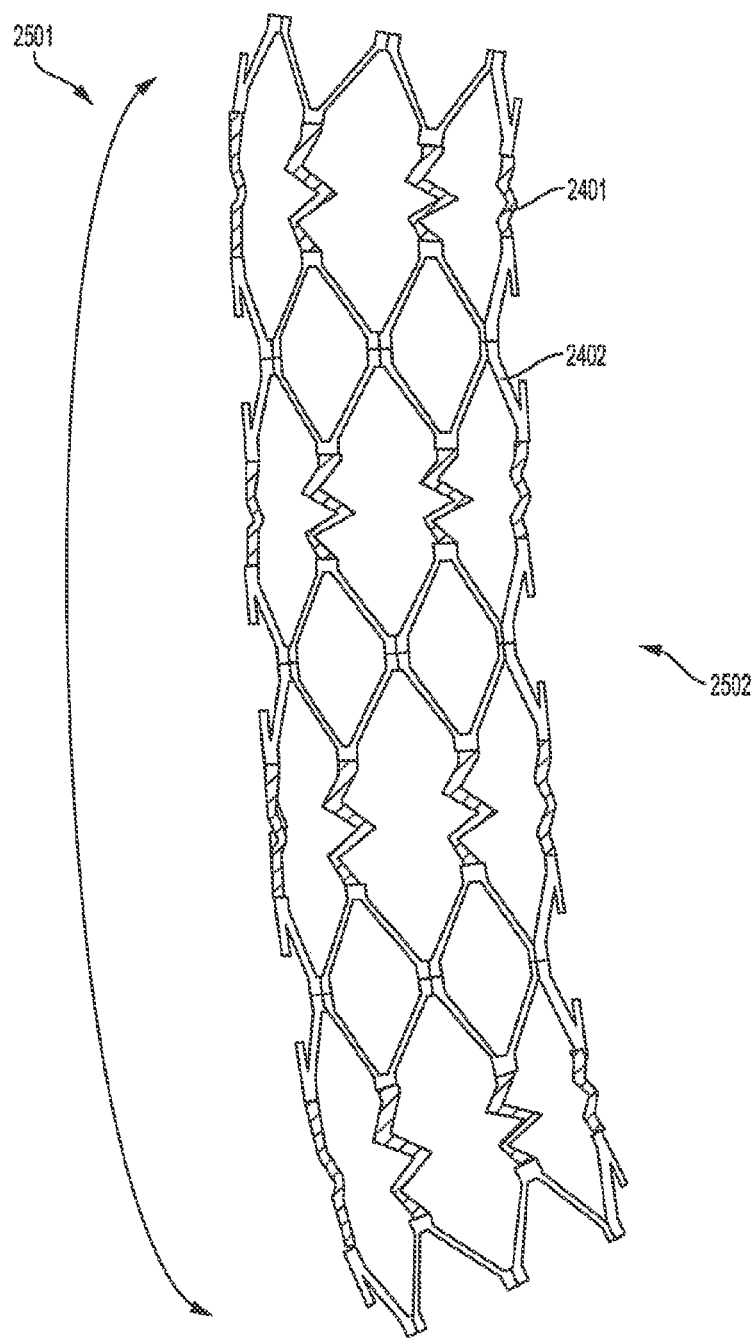
FIG. 25 illustrates bending of the anchor or anchoring frame illustrated in FIG. 24.

Referring to FIG. 25, the spring/flexible segments 2402 allow the anchor or anchoring frame 2801 to more easily bend. The frame 2801 can bend in a wide variety of different ways. In the example illustrated by FIG. 25, springs on one side 2501 stretch and springs on another side 2502 compress to bend in the indicated direction. Since multiple spring/flexible segments 2401 are provided in the frame 2801, the frame can easily bend in different directions along the length of the frame 2801.

Figure 26:
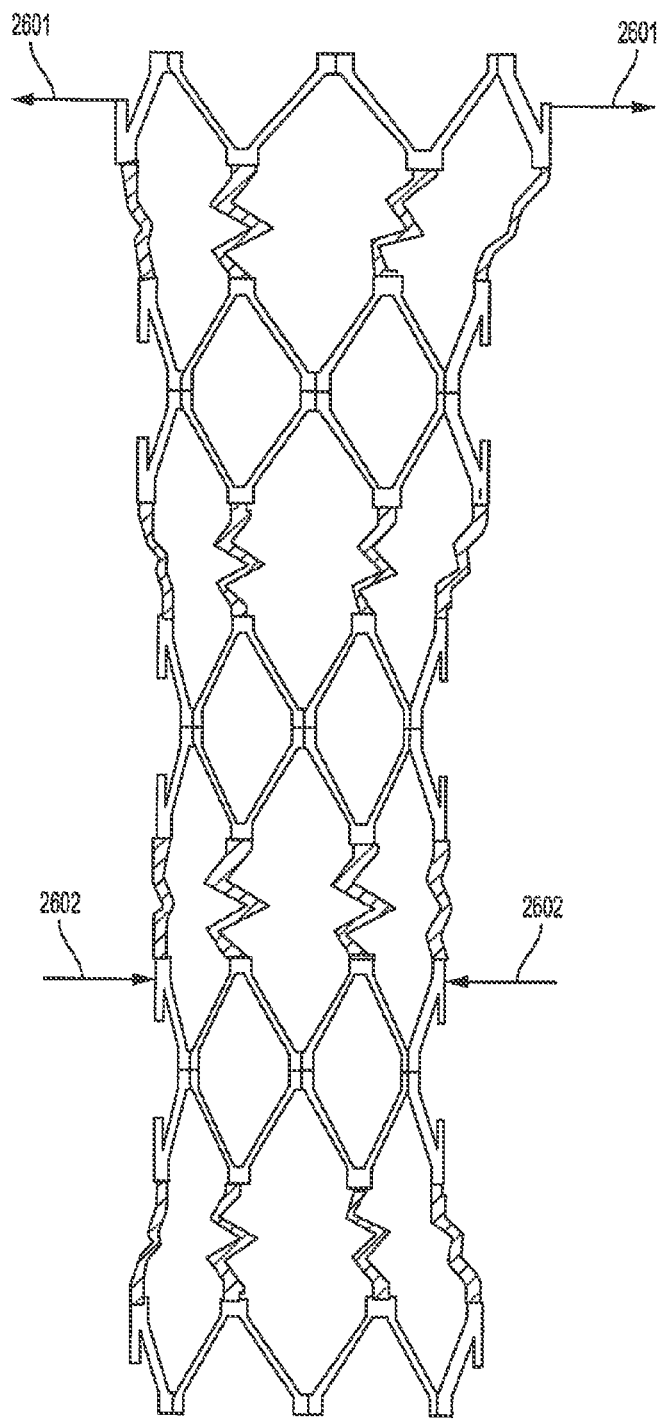
FIG. 26 illustrates expansion and contraction of anchoring frame portions and flexible portions of the anchor or anchoring frame of FIG. 24.

FIG. 26 illustrates that the frame or stent segments 2402 are expandable (indicated by arrows 2601) and compressible (indicated by arrows 2602). By having separate stent segments 2402 connected by spring/flexible segments 2401, the frame can more easily conform to blood vessels or pulmonary veins that have varying sizes. The combination of the stent segments 2402 and spring segments 2401 allows the anchoring frame to conform to blood vessels that vary in cross-sectional size of the vessel, cross-sectional shape of the vessel, and the flow shape or path of the vessel.

Figure 27:
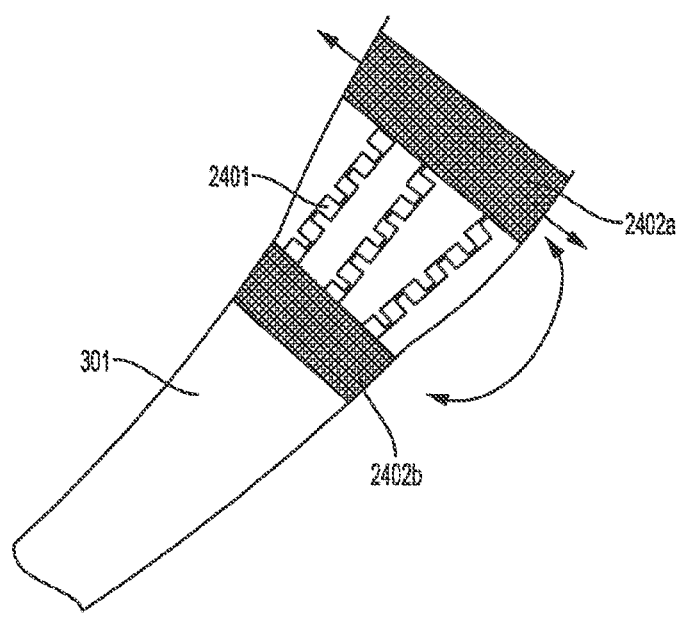
FIG. 27 illustrates an exemplary anchor or anchoring frame deployed in a blood vessel.

FIG. 27 illustrates an exemplary embodiment of an anchor or anchoring stent 2801 that includes two frame or stent segments 2402 connected by spring segments 2401. In the example illustrated by FIG. 27, the anchoring stent 2801 is deployed in a blood vessel, referred to for illustration as pulmonary vein 301, that is curved and has a varying cross-sectional size. A first frame or stent segment 2402a expands to a first size to conform to the size of the pulmonary vein at the location where the first frame or stent segment is deployed. A second frame or stent segment 2402b expands to a second, larger size to conform to the size of the pulmonary vein at the location where the second frame or stent segment is deployed. The anchoring stent 2801, without valves, can be positioned in the pulmonary veins. The pulmonary vein is curved from the location of the first stent or frame segment 2402*a* to the location of the second stent or frame segment 2402*b*. The spring elements 2401 allow the frame to bend and conform to the curvature of the pulmonary vein.

Figure 28:
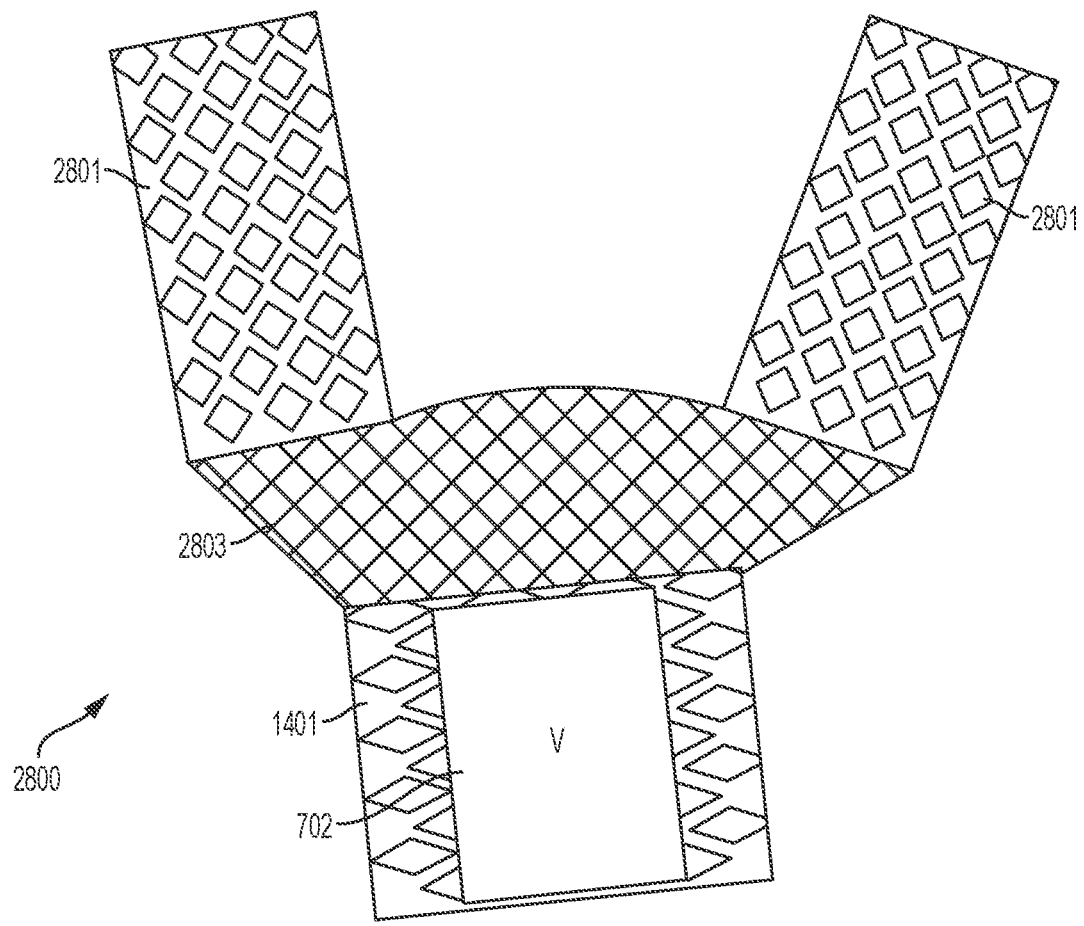
FIG. 28 illustrates an exemplary valvular implant, device, or system with anchors or anchoring frames to fit in the blood vessels and a dock or docking frame to fit in the left atrium.

FIG. 28 illustrates another embodiment of closure device or valvular implant/system having a dock 1401 with a valve 702. As with other exemplary embodiments described herein, the valve can be integral with the dock or can be a separate component that is inserted in a separate step after the dock is inserted. The dock 1401 in FIG. 28 can have anchors or anchoring portions 2801, which are only a portion of the overall device, can have the properties described in regards to FIGS. 24-27. This implant 2800 has two anchors or anchor portions 2801 (which can be pulmonary vein anchors) and one dock 1401 (which can be an atrial dock) for holding a unidirectional valve. The anchors 2801 can be stents and can be made of a superelastic laser cut tube or a braided nitinol tube and can have alternating struts. The anchors 2801 can be covered with a suture cloth or polymer-dipped, or a polymer coating applied by electrospinning. This covering applies a sealing property to the device. The diameter of each anchor/anchoring portion applies a low outward force so that it can match to a large diameter range while applying constant force. The material properties are such that the material can adjust to different anatomies so that there can be a seal between the two anchors 2801 after they are implanted, for example, in the blood vessels or pulmonary veins, regardless of the exact anatomical spacing between the two blood vessels or pulmonary veins. The dock or atrial dock 1401 can be made of a superelastic laser cut tube such as that of FIGS. 24-27, or can be made of braided Nitinol. In an embodiment where the valve is implanted separately, this dock 1401 can have higher forces than the anchors or anchor portions to allow for docking of the valve 702.

FIG. 28 also illustrates the connecting piece 2803 between the dock 1401 and the anchors/anchoring frames 2801. The connecting piece can be made in a variety of ways, for example, it can be made of a variety of one or more materials, such as a cloth or a dense nitinol braid or the connecting piece can be any biocompatible material that is soft and inhibits blood flow, and/or can create a seal between the anchors. In an exemplary embodiment, the stiff component can hold the Nitinol frame, and a covering or soft material can be used to seal the stiff component. In an exemplary embodiment, the material 2803, stents 2801, and anchor 1401 are all sealed together so that the blood flow from the blood vessels or pulmonary veins is directed down and out through the valve 702. The connecting piece 2803 holds the anchors in place relative to the dock and maintain proper positioning of the components of the implant relative to each other. The complete implant unit 2800 can be covered in a soft material to seal the device and prevent improper bloodflow.

Figure 29:
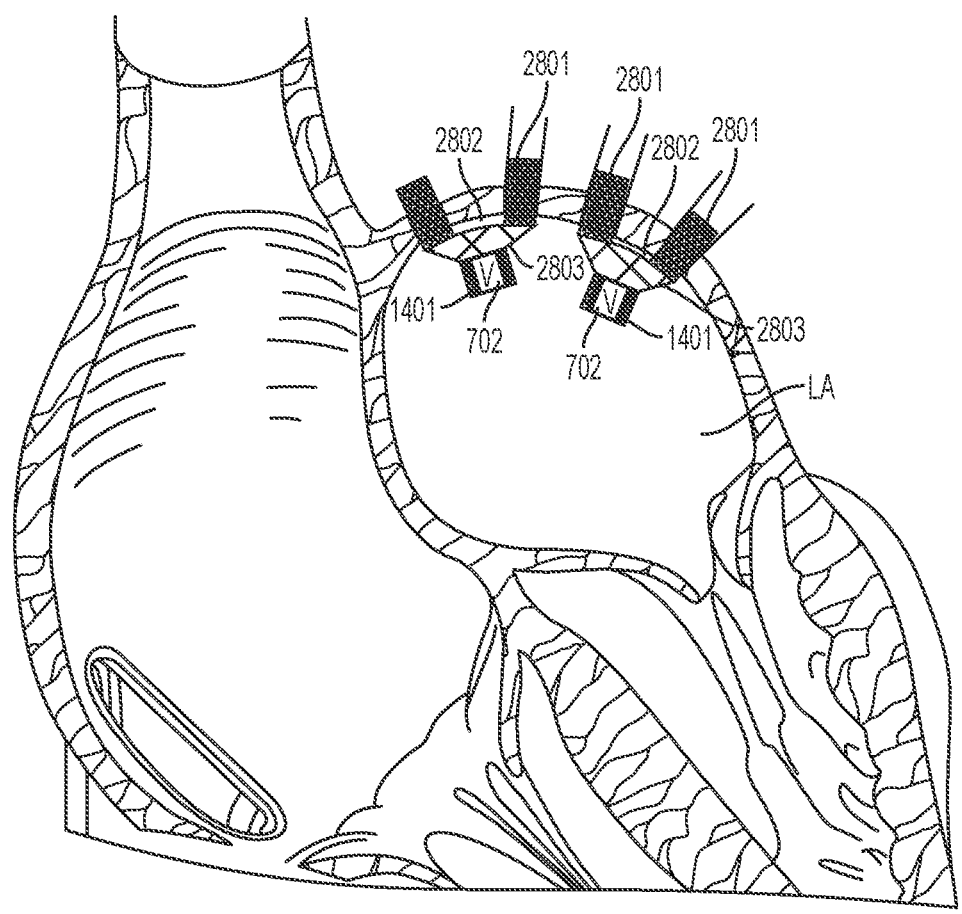
FIG. 29 illustrates a schematic of deployment of two valvular implants or devices of the exemplary embodiment illustrated in FIG. 28.

FIG. 29 illustrates the implant of FIG. 28 in an exemplary position in the heart. By using two implants, each having two pulmonary vein anchors, it is possible to choose either one or both pairs of pulmonary veins to protect. One pair of pulmonary veins enters the left atrium from the left lung, and the other pair of pulmonary veins enters the left atrium from the right lung. By using one implant device 2800, one pair of pulmonary veins can be protected from improper blood flow. The pulmonary veins protected from improper blood flow can be those connecting either the right lung or the left lung to the left atrium. By using two implant devices 2800, all four pulmonary veins can be protected from improper blood flow.

During a first phase of implantation, one or two anchoring units can be implanted. Then in a second phase of implantation, a valve 702 can be implanted in each of the atrial docks or docking anchors. The implants 2800 can be implanted transeptally or transapically. The covering materials (e.g., cloth, cloth-like materials, polymers, etc.) in combination with the stent-like frames of the anchors are configured to allow the elements of the device to be compacted and positioned in a delivery catheter for transcatheter delivery through vasculature and into the right or left atrium of the heart.

Figure 30:
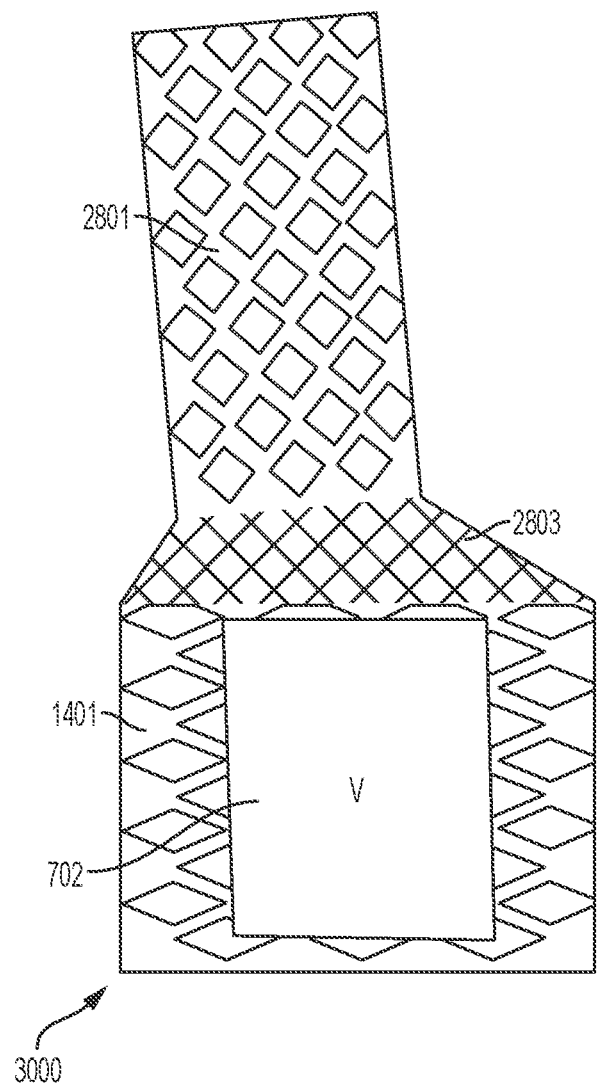
FIG. 30 illustrates an exemplary valvular implant or device with a dock or docking portion and an anchor or anchoring component for anchoring within a blood vessel orifice.
Figure 31:
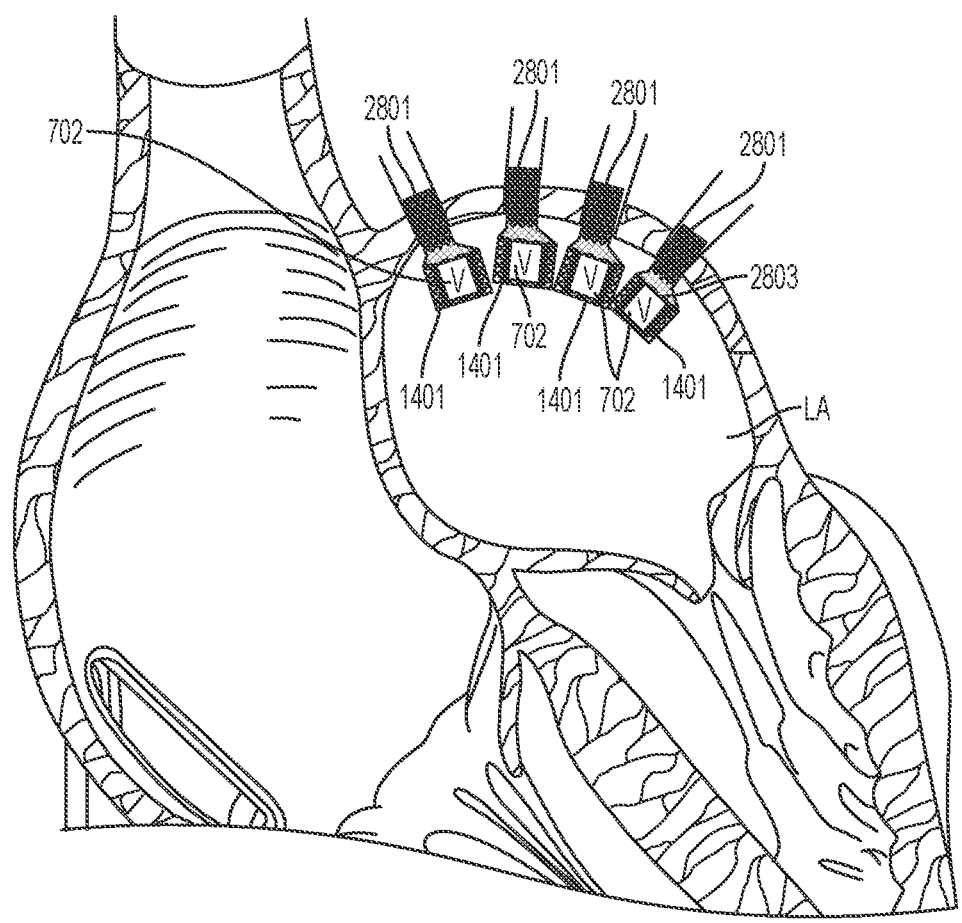
FIG. 31 illustrates a schematic of deployment of four valvular implants or devices of the exemplary embodiment illustrated in FIG. 30.

FIGS. 30 and 31 illustrate a schematic of an exemplary closure device or valvular implant dock similar to that of FIGS. 28 and 29. There is one anchor or anchoring stent 2801 attached to the dock 1401. In one embodiment, the anchor/anchoring stent 2801 can be configured for implantation in a pulmonary vein while the dock 1401 stays in the left atrium. One or multiple implants 3000 can be implanted, such as one, two, three, four, etc. identical units, separated from each other; for example, one unit 3000 can be implanted in each pulmonary vein. By using implant 3000, any combination of one to four blood vessels or pulmonary veins can be protected from improper blood flow. The materials and structure of the components can be the same as with the two-pulmonary vein anchor embodiment. However, there does not need to be a piece of material or anything connecting any of the pulmonary vein anchors 2801 together. In various embodiments, material 2803 connects anchors 2801 to docks 1401, providing a fluid seal around the valve.

Figure 32:
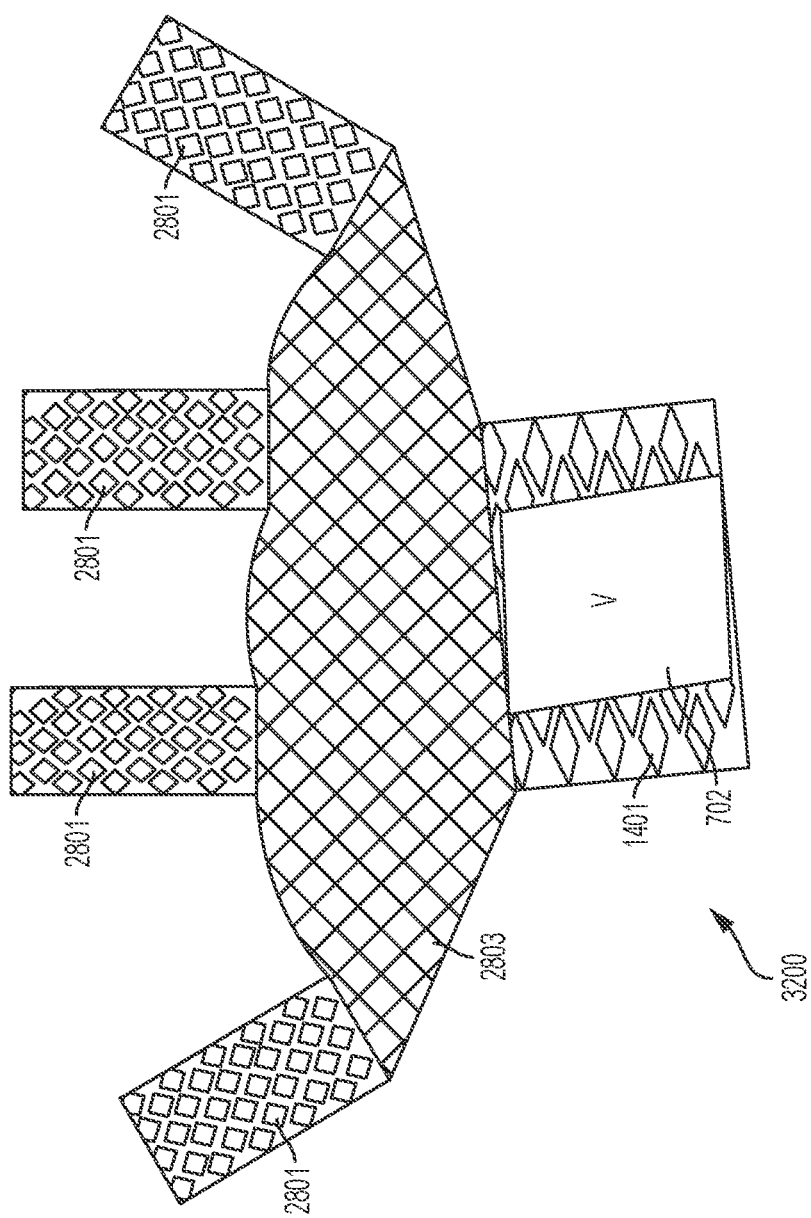
FIG. 32 illustrates a valvular implant or device with four anchors or anchoring frames to fit in four blood vessels, such as four pulmonary veins, and one exemplary dock/docking portion (or, optionally, integral valve/valve portion).
Figure 33:
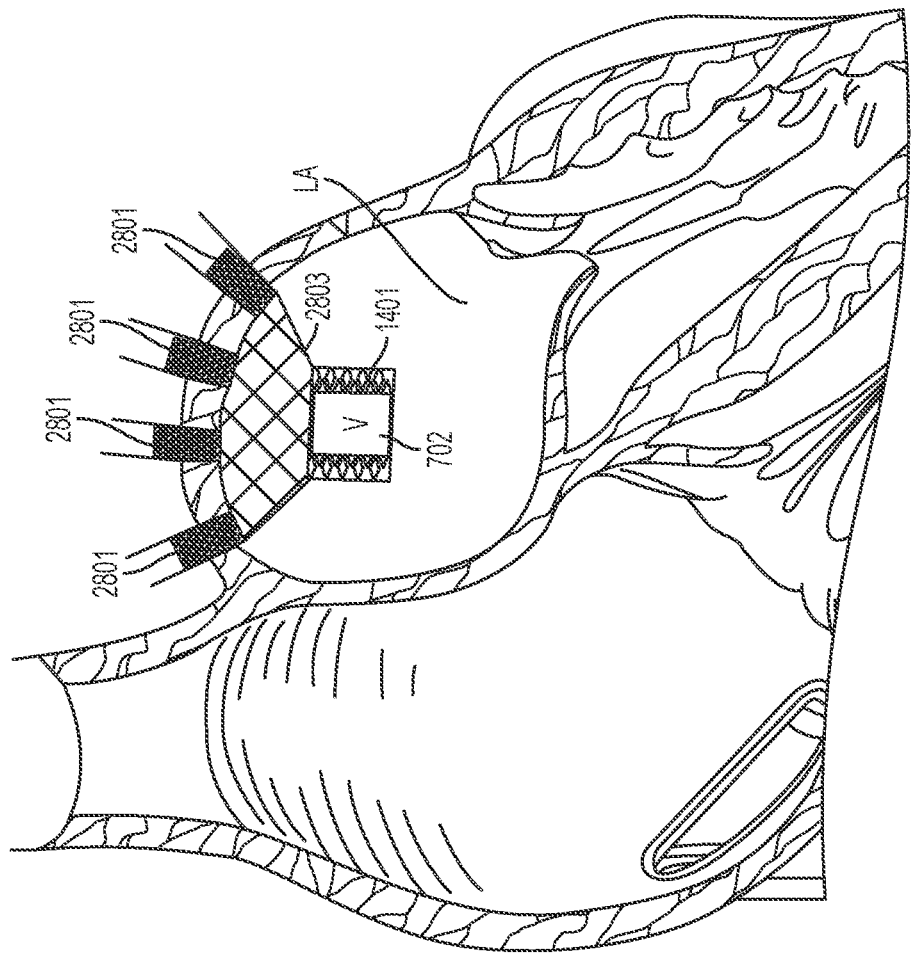
FIG. 33 illustrates a schematic of deployment of the pulmonary vein implant device of the exemplary embodiment illustrated in FIG. 32.

FIGS. 32 and 33 illustrate a schematic of an exemplary closure device or valvular implant/system 3200. Implant 3200 has four blood vessel anchors or anchoring portions 2801 and one dock 1401 for a unidirectional valve. All four blood vessel anchors 2801 are shown connected to the same valvular implant/system. The connecting piece or sack 2803 can be nitinol or other biocompatible material and can be covered with a cloth to provide a seal, blocking unwanted bloodflow. The connecting piece or sack 2803 in this embodiment can have an opening at the top, near the blood vessel or pulmonary vein orifices, to direct bloodflow through the connecting piece or sack and through the valve. As with the embodiments described in FIGS. 28-31, the valve 702 in the dock 1401 is a unidirectional valve. The anchors and stents of this embodiment are similar to that of the embodiments illustrated in FIGS. 28-31. The valve can be integrated with the dock or implanted in part of a two-phase procedure, where the first phase includes implanting the anchoring components, and the second phase includes implanting the valve. In all of the embodiments where the valve is already connected to the anchor, the valve can be connected to the anchor by suturing.

Figure 34:
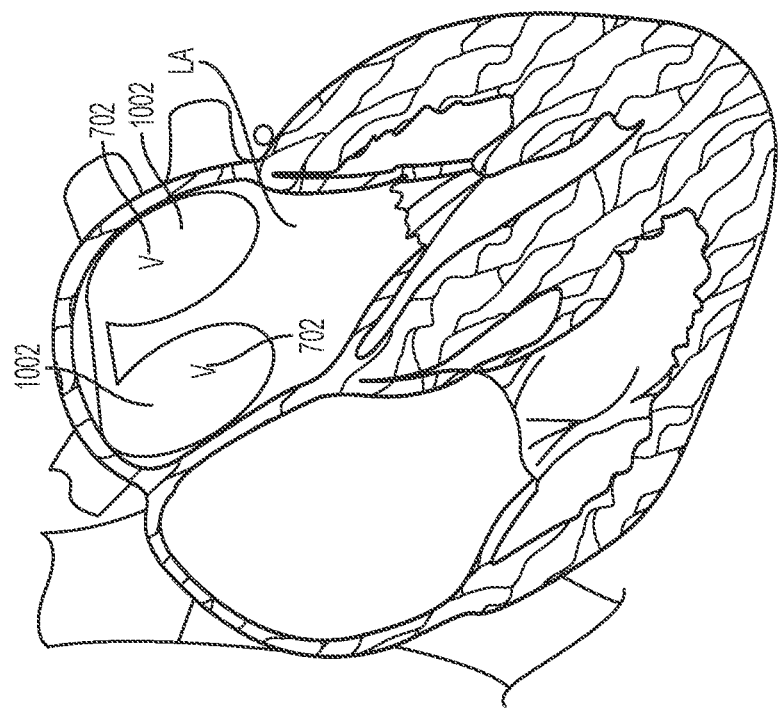
FIG. 34 illustrates an exemplary pulmonary vein implant device having two valve sections.

Referring to FIGS. 34-41, an exemplary closure device or valvular implant/system is disclosed. In this embodiment, two unidirectional portions 1002, each comprise a unidirectional valve portion 702 and each is configured to cover multiple blood vessels, such as two pulmonary vein orifices each. FIG. 34 illustrates a schematic of this embodiment and how it can be positioned, for example, in the left atrium LA of the heart.

Figure 37A:
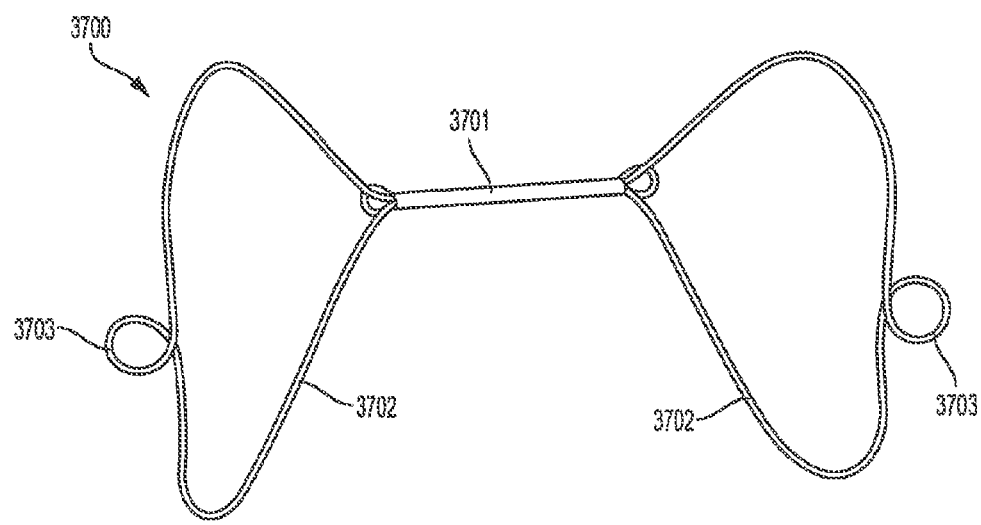
FIGS. 37A-37C are bottom, side, and perspective views of an exemplary frame for the implant in accordance with the schematic illustrated in FIG. 34 in three different orientations.
Figure 37B:
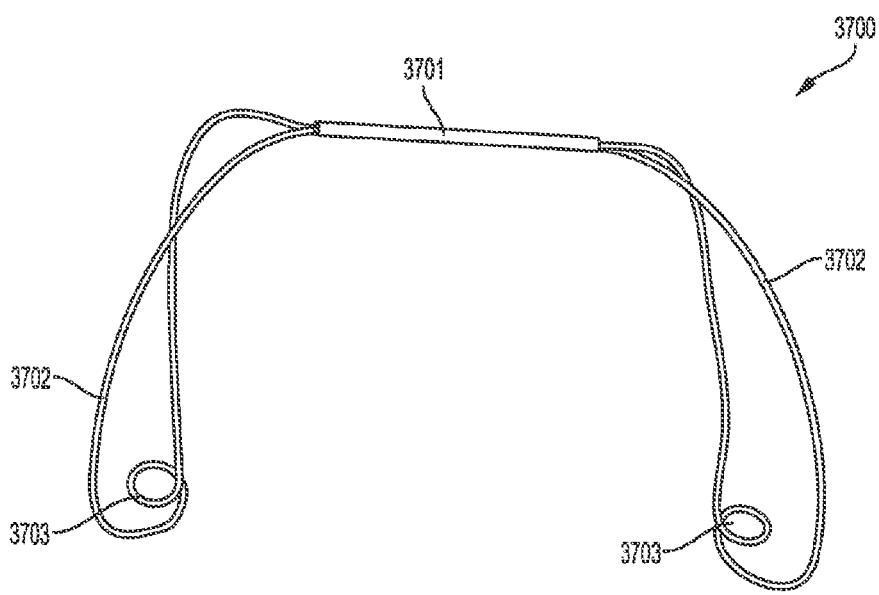
Figure 37C:
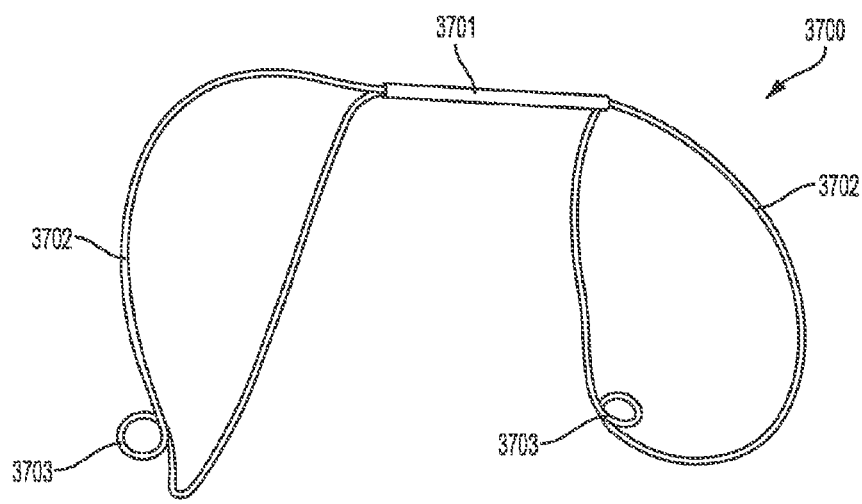

FIGS. 37A-37C illustrate varying structures of a resilient wire-form frame 3700. The frame can be made of Nitinol. The frame 3700 has a connecting bridge 3701 between two frame bases 3702. The frame bases can be large curved portions, looped portions, expanded portions, etc. The frame bases can have a variety of shapes two-dimensionally and three-dimensionally, including circular, ovoid, oval, other shapes, generally or approximately one of these or another geometric shape, etc. can also have strain reduction elements 3703. Strain reduction elements can be ring-shaped and can face inward (not illustrated) or they can face outward, as in FIG. 37A. The connecting bridge 3701 can be a tube, spring, wire and/or other structure.

Figure 35:
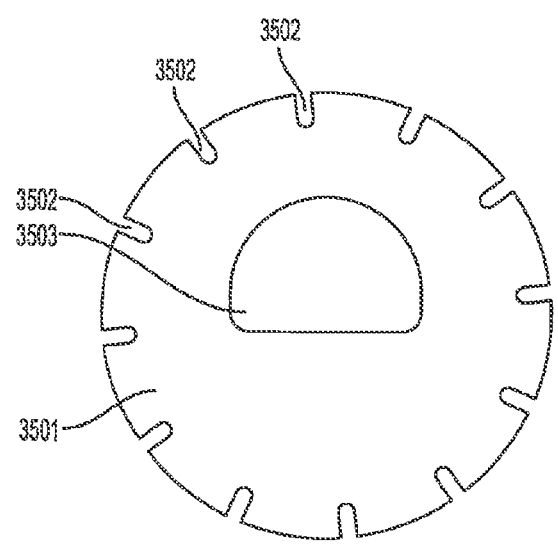
FIG. 35 illustrates an exemplary valve panel or membrane usable in the embodiment illustrated in FIG. 34.
Figure 36:
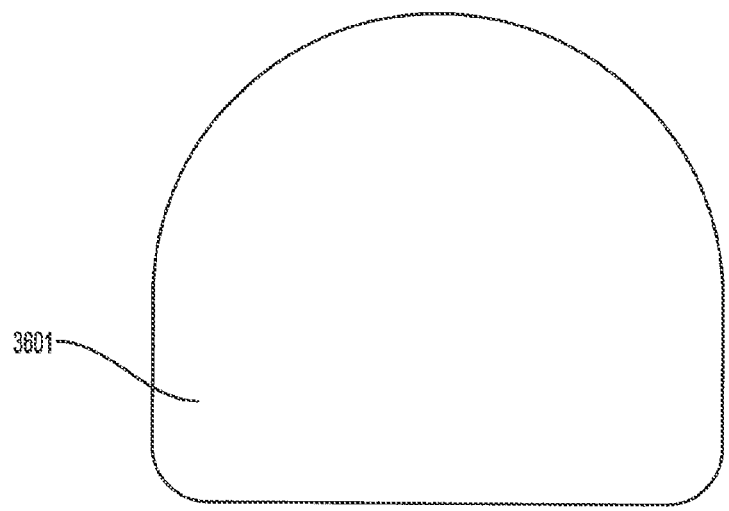
FIG. 36 illustrates an exemplary valve leaflet, membrane, or flap of the embodiment illustrated in FIG. 34.

FIGS. 35 and 36 illustrate the components of an exemplary unidirectional valve portion or two-layer membrane valve. FIG. 35 illustrates a first membrane or valve panel 3501 that is attached to a frame base 3702. The first layer has an outer perimeter with optional notches 3502 to assist with properly fitting and connecting the membrane to the base. The first layer also has an opening 3503. FIG. 36 illustrates a second membrane, leaflet, or flap 3601 which covers the opening 3503 of the first layer 3501. These two membranes create the unidirectional valve or valve portion of the wire-form frame implant.

Figure 38:
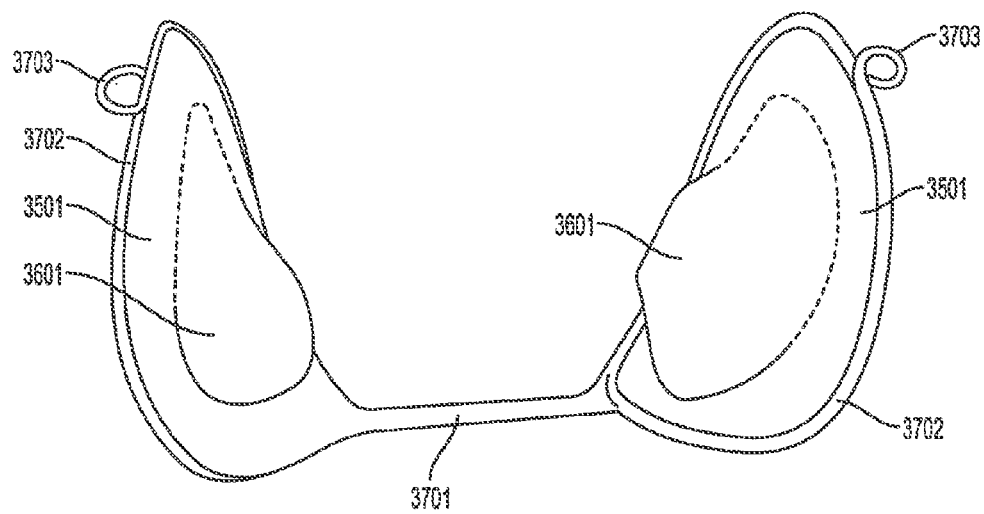
FIG. 38 illustrates an exemplary valvular implant or device having a wire frame and two valves or valve portions or sections, which implant or device can incorporate features the same as or similar to those shown in FIGS. 34-37C.

In FIG. 38, all the elements of FIGS. 35, 36, and 37A-37C are assembled together to form a closure device or valvular implant/system. In one embodiment, the valvular implant or system is configured to be a pulmonary vein valve implant for use with all four pulmonary veins. Each of the membranes can cover a portion of the left atrial wall that has two pulmonary vein orifices. In one embodiment, the valve implant or system is configured to cover portions of the right atrial wall to cover the inferior vena cava IVC and superior vena cava SVC orifices. On each side of the implant, the blood entering the heart (e.g., entering the left atrium, etc.) from the blood vessels (e.g., from the pulmonary veins, etc.) can flow in freely through the opening 3503 into the heart or left atrium. However, the membrane, leaflet, or flap 3601 is positioned such that blood cannot flow back from the heart (e.g., left atrium, right atrium, etc.) into the blood vessels (e.g., pulmonary veins, IVC, SVC, etc.). Any blood in the left atrium due to a deficient mitral valve, or in the right atrium due to a deficient tricuspid valve, would cause the flap 3601 to be pushed back against the atrial wall and block the openings of the blood vessels. The flaps 3601 can be attached to the first layer 3501 of the membrane by sutures, adhesive, or other known techniques.

Figure 39:
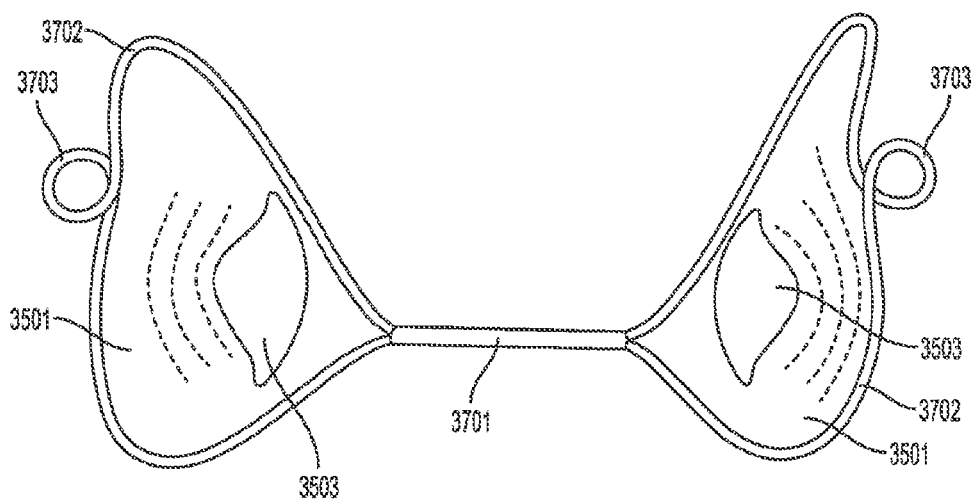
FIG. 39 illustrates an exemplary valvular implant or device having a wire frame and single-piece membrane valves or valve portions.
Figure 40:
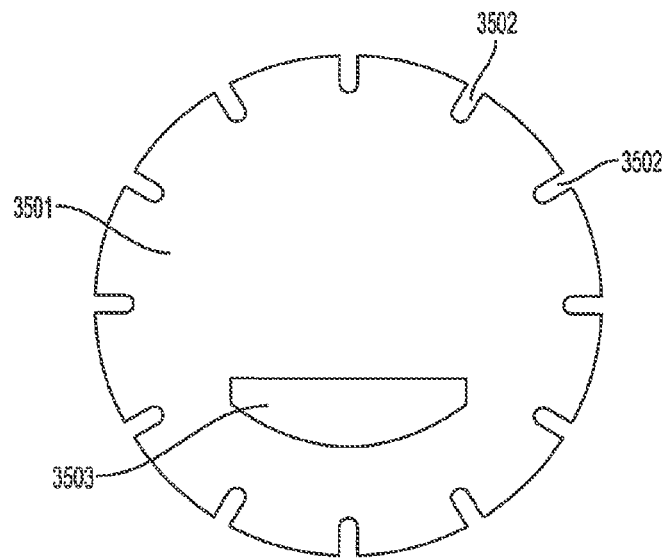
FIG. 40 illustrates an exemplary membrane useable in a valvular implant or device such as the exemplary implant/device illustrated in FIG. 39.
Figure 41:
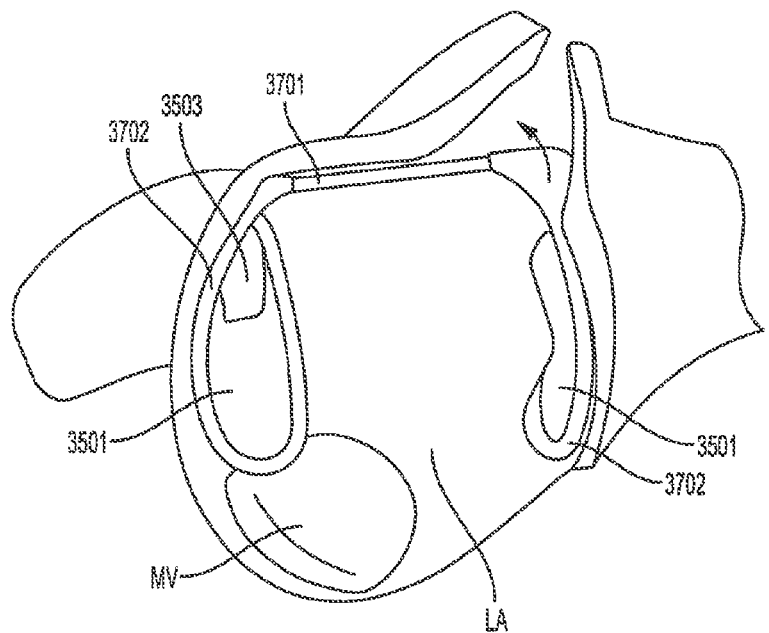
FIG. 41 illustrates a schematic of an exemplary valvular implant or device implanted in a left atrium.

FIG. 39 illustrates an exemplary embodiment of a wire-form valvular implant or system formed using a membrane. Each membrane or valve panel 3501 can be made of a single piece of material that is attached to one or both of the frame bases 3702 to create a unidirectional valve or valve portion activated by flow. FIG. 40 illustrates the membrane 3501 of FIG. 39, which also has an opening 3503 and can have a notched outer perimeter with optional notches 3502. The membrane can be attached to the frame such that the material of the membrane bunches up to open the opening 3503. Blood entering the heart (e.g., left atrium, right atrium, etc.) from the blood vessels (e.g., pulmonary veins, etc.) can flow through the opening 3503 into the heart (e.g., left atrium, right atrium, etc.). However, the bunched material is pushed and flattened thereby spreading out and closing the opening 3503 by any regurgitant blood, to prevent or inhibit blood from flowing back into the blood vessels. FIG. 41 illustrates the embodiment of FIG. 39 implanted in position, for example, in the left atrium of the heart. The frame bases 3702, bridge tube 3701, single layer membranes 3501, and openings in the membranes 3503 are visible. The two membranes 3503 can cover all four pulmonary veins.

Figure 42A:
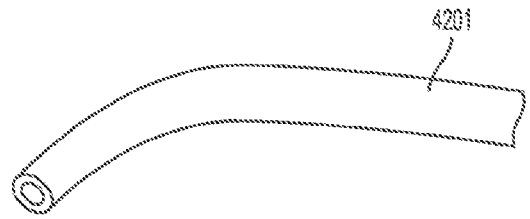
Figure 42B:
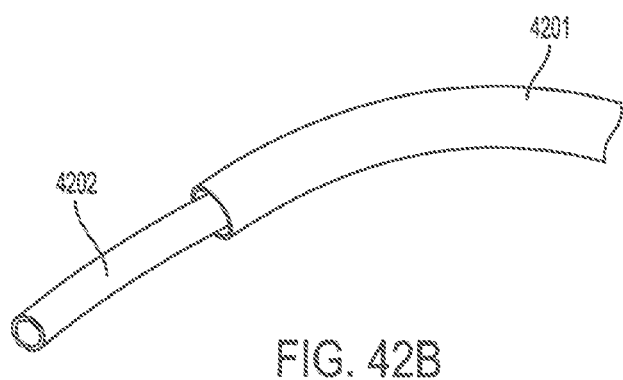
Figure 42C:
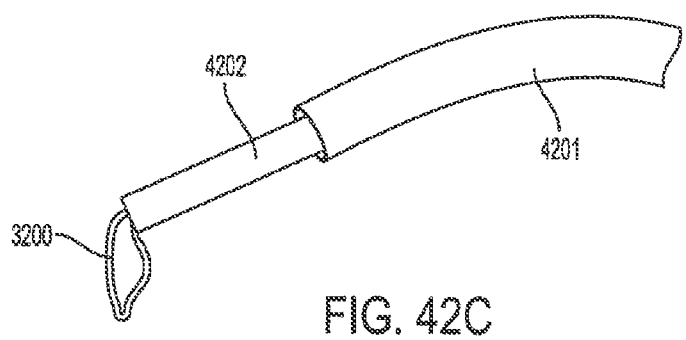
Figure 42D:
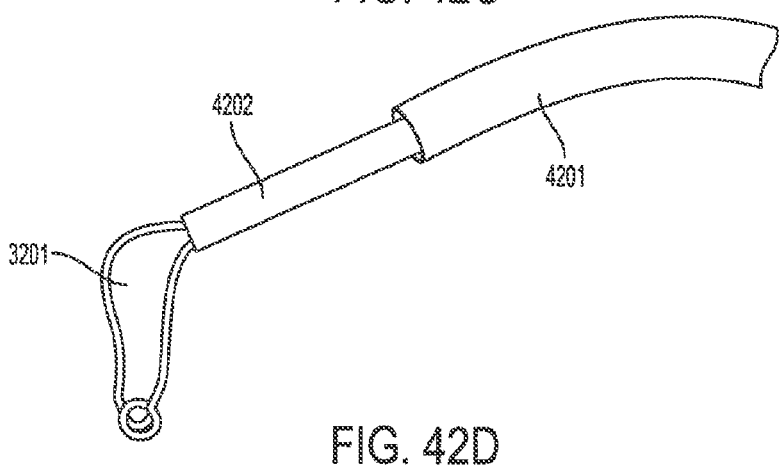

An exemplary deployment of a wire form, membrane valvular implant or closure device is illustrated in FIGS. 42A-42I. Deployment can be done transvascularly, and can be done transeptally, including through an active flexible guide sheath that passes through the fossa ovalis, from the right atrium to the left atrium. Deployment can be done on a living animal or on a non-living cadaver, cadaver heart, simulator, anthropomorphic ghost, etc. Referring to FIGS. 42A and 42B, a tube is advanced, for example, toward the left atrial appendage. Referring to FIGS. 42C and 42D, the implant is deployed by pulling back the tube and advancing an internal pusher. Referring to FIGS. 42E-42H, once the distal membrane valve is deployed the catheter is retracted to deploy the rest of the implant. Referring to FIG. 42I, the final stage of deployment is the release of an internal pull wire or suture 4203. The device is fully retrievable throughout the deployment by pulling the pull wire and/or suture 4203 back in a proximal direction.

Figure 42E:
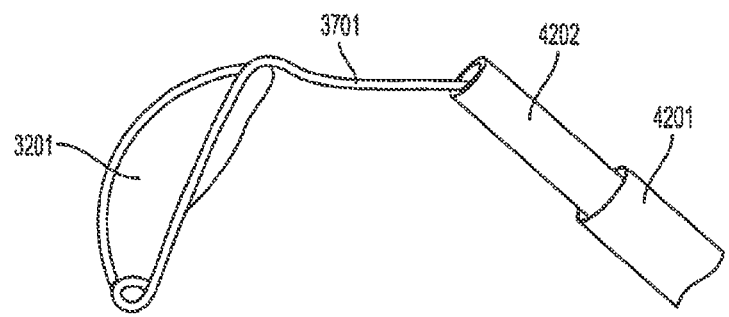
Figure 42F:
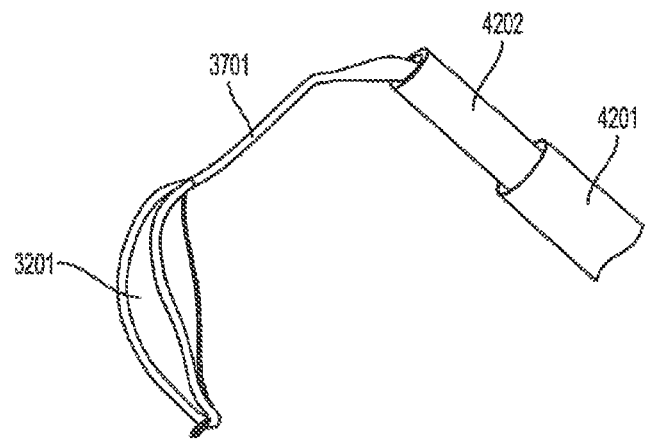
Figure 42G:
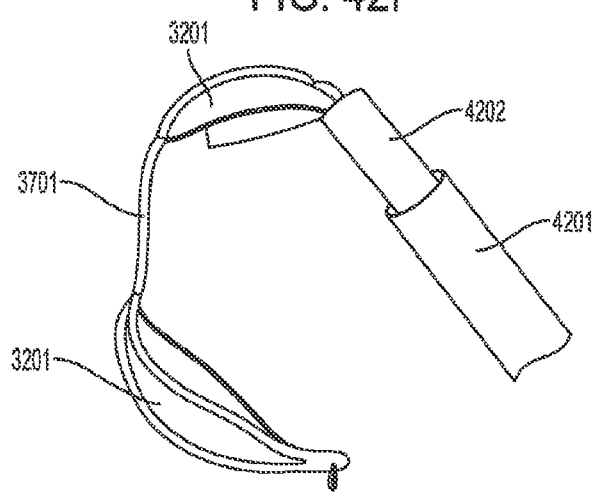

FIG. 42A illustrates a guide sheath 4201 in a flexed position. FIG. 42B illustrates the delivery catheter or tube 4202 emerging from the guide sheath 4201. When being deployed in the heart, the guide sheath and the delivery catheter can point in the direction of the left atrial appendage. In FIG. 42C, the implant 3200 is advanced out of the delivery catheter/tube. In FIG. 42D, the implant is advanced enough so that the first membrane 3201 is deployed. This first membrane part of the implant is positionable over the blood vessel orifice(s), (e.g., pulmonary vein orifices, etc.) on one side of the atrium. FIG. 42E illustrates the deployed first membrane 3201 and the bridge 3701, which are now both external to the delivery catheter/tube 4202. FIG. 42F illustrates the advancement of the second membrane 3201 from the delivery catheter/tube 4202. In FIG. 42G, the second membrane is almost fully deployed from the delivery catheter/tube, and in FIG. 42H, the second membrane is deployed. At this point in the deployment process, it is desirable to have the second membrane of the implant over another blood vessel orifice(s), such as over the second two pulmonary veins. FIG. 42I illustrates the deployment of the implant from the catheter/tube 4202, and an internal pull wire or suture 4203 extending from the tube. The internal pull wire or suture 4203 can be threaded through a strain reducing loop 3703. Once the implant is positioned properly, the pull wire is removed from the implant, as the final step in deployment. The pull wire can be removed by cutting it at the proximal end and pulling it out. The membranes of the implant can be the two-piece membranes or the one-piece membrane embodiment shown in FIGS. 38 and 39.

Figure 43A:
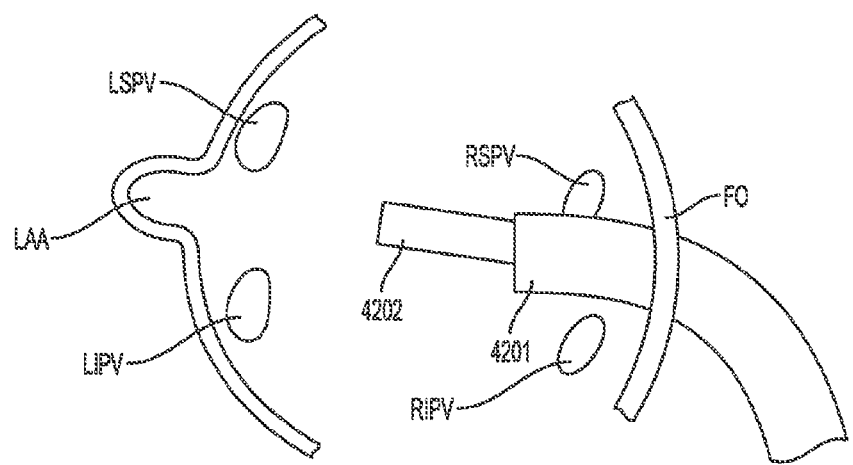
FIGS. 43A-43D illustrate exemplary steps usable in deploying and implanting a valvular implant in accordance with the embodiments illustrated in FIGS. 34-41.
Figure 43B:
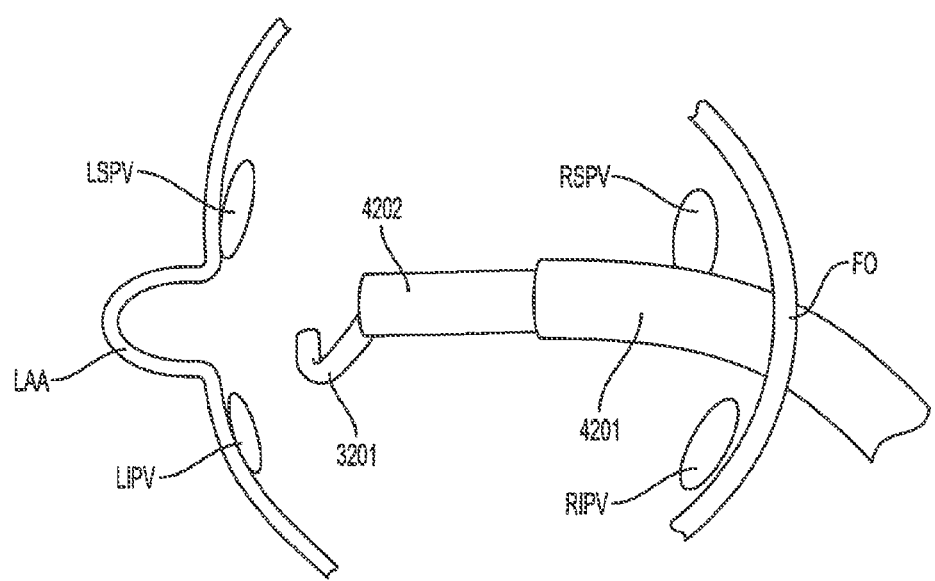
Figure 43C:
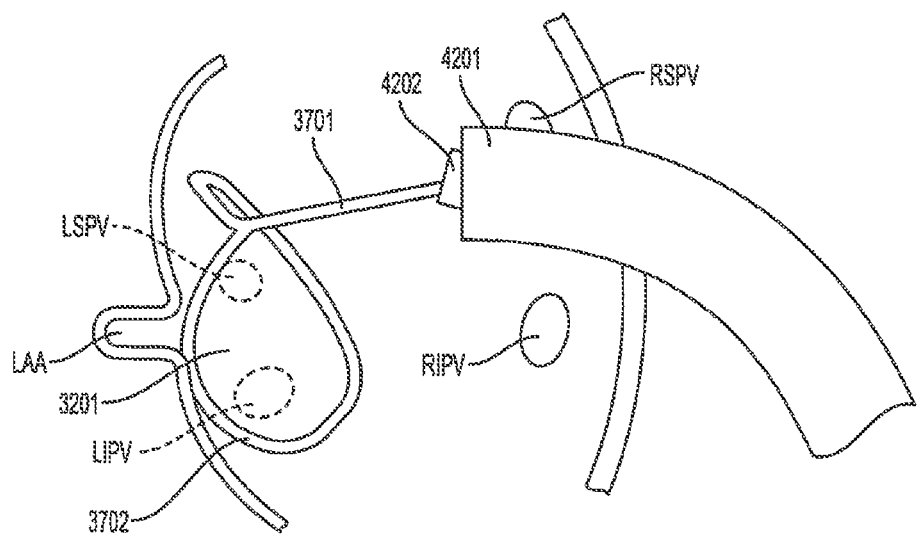
Figure 43D:
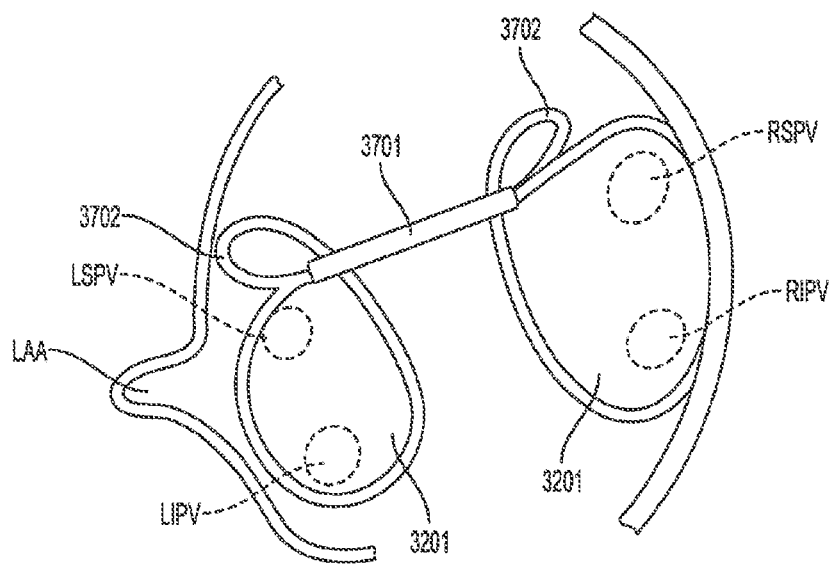

FIGS. 43A-43D illustrate the deployment of the exemplary implant or system of FIG. 38 or the exemplary implant or system of FIG. 39 in the left atrium (though deployment can be adapted for other locations such as the right atrium). When the implant is deployed into a final position, all the desired blood vessel or pulmonary vein orifices are covered, and the left atrial appendage is optionally blocked. FIG. 43A illustrates the guide catheter 4201 and the delivery catheter/tube 4202 in the left atrium LA after having passed through the fossa ovalis FO. The capsule tube and guide catheter are pointed in the direction of the left atrial appendage LAA. In FIG. 43B, the deployment of one membrane 3201 in the implant has begun, as it is pushed out of the delivery catheter/tube. Optionally, the delivery catheter or a sheath can be retracted while holding the implant in place. FIG. 43C shows the deployment of the first membrane and the bridge tube 3701, in a position that covers two blood vessel or pulmonary vein orifices 302 and the LAA. In an exemplary embodiment, the LAA is curved by a portion of the membrane. FIG. 43D illustrates the fully deployed implant, where the second membrane 3201 is also deployed and covers the remaining two blood vessel or pulmonary vein orifices 302. The components used and method of implanting the implant allow the implant to be retracted and repositioned. In the installed position, the implant or device allows blood flow out of all blood vessels (e.g., out of all four pulmonary veins), but prevents blood flow back into the blood vessels or pulmonary veins.

FIG. 44 illustrates another exemplary embodiment of a wire-form valve valvular implant or system 4400 formed using a wire frame 4401, connecting material 4402, and valve portions comprising flaps 4403. The connecting material 4402 is connected around the periphery of the wire frame 4401. In the illustrated example, two flaps are connected to the connecting material. In one exemplary embodiment, the flaps 4403 are omitted and the connecting material 4402 covers the entire area that the connecting material and flaps cover in FIG. 44. In one exemplary embodiment, the flaps 4403 can be attached to an entirety of the overlapping area between the connecting material 4402 and the flaps 4403 (See FIG. 47 where the flaps flex out due to the connection around the overlapping area). In another exemplary embodiment, only end portion of the flaps 4403 are attached to the connecting material 4402 (See FIG. 49 where the flaps flap out due to the connection only at the end portion of the flaps).

Figure 45:
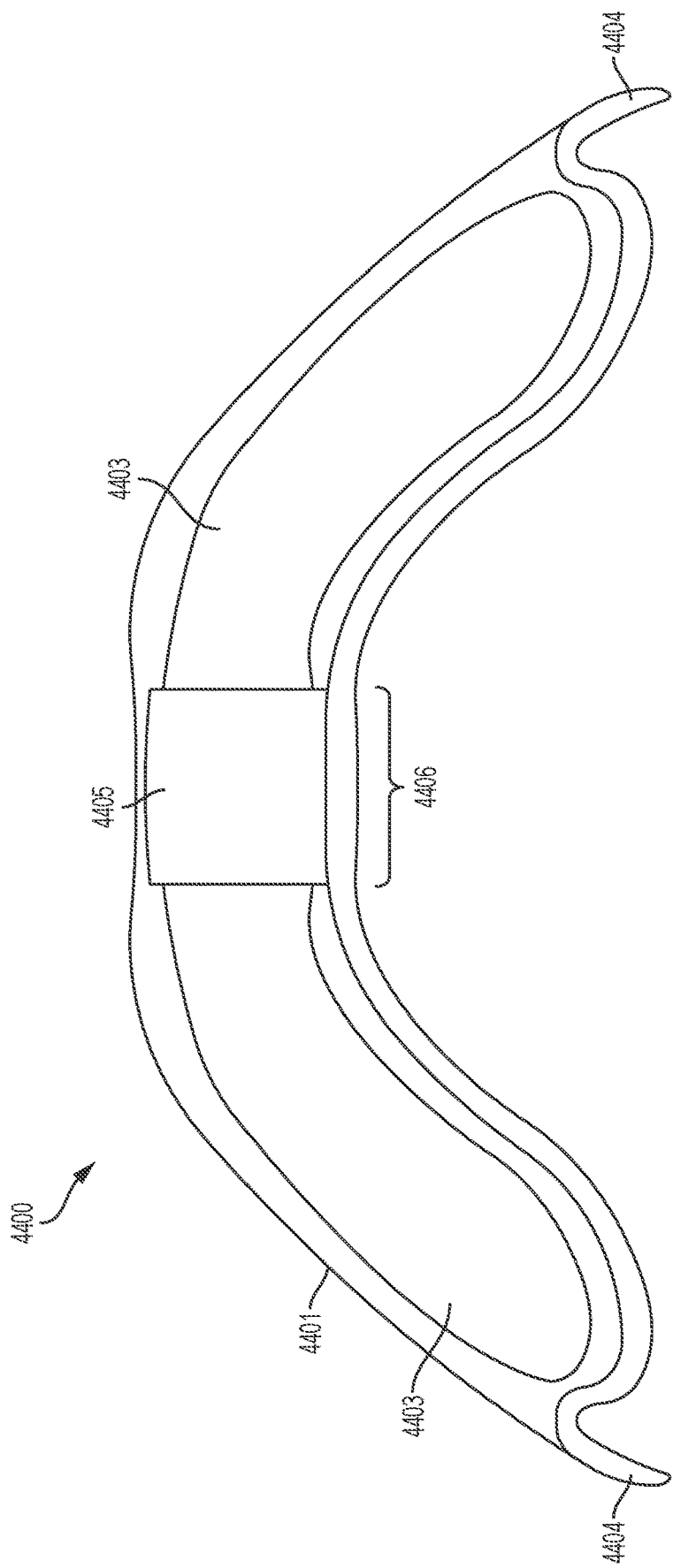
FIG. 45 illustrates another view of the valvular implant of FIG. 44.

The connecting material 4402 and/or the membranes or flaps 4403 can be made of a fabric and/or tissue, such as pericardial tissue. The membranes or flaps (as well as other valve portions described elsewhere herein) can be treated and/or coated with chemicals, drugs, etc. to prevent or inhibit calcification and/or tissue ingrowth into the membrane. The frame 4401 can be Nitinol and can have strain reducing shaped ends 4404 (which can have the shape shown or another strain reducing shape like, for example, strain reducing portions 3703). The flaps 4403 can be connected to the membrane 4402 by stitches, adhesive, etc. The frame 4401 can have an hourglass-like shape when in an expanded configuration, that also curves to conform to the circumference of a left atrium in the area of the pulmonary veins. The illustrated exemplary frame 4401 has connecting material 4402 attached to the frame, all the way around the frame. An opening 4405 remains uncovered by the flaps 4403 in a narrower "bridge" or "waist" region 4406 of the frame. Attached to the connecting material 4402 on each side of the frame 4401, is a flap 4403. The flaps can be attached to the connecting material 4402 around a large portion of the flap such that at least the remaining portion of the flap can flex open to permit bloodflow when in an open configuration. Or, the flaps can be connected to the connecting material 4402 around only a small portion of the flap 4403, such that the remaining portion can flip or flap open to permit bloodflow when in the open position. FIG. 45 illustrates another view of the embodiment of FIG. 44.

Figure 46:
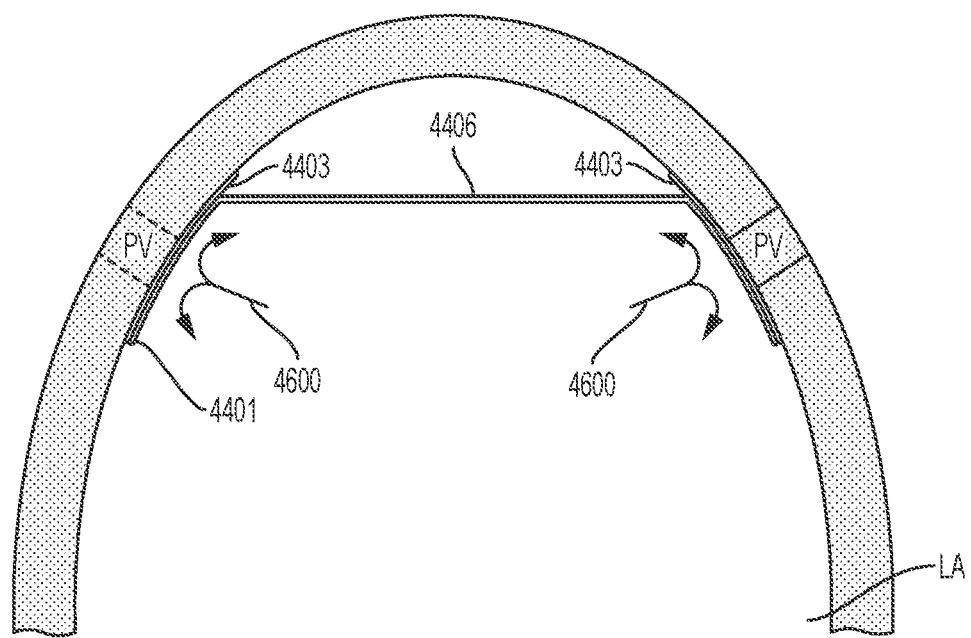
FIG. 46 illustrates a schematic of the valvular implant of FIG. 44 in a closed configuration in the left atrium.
Figure 47:
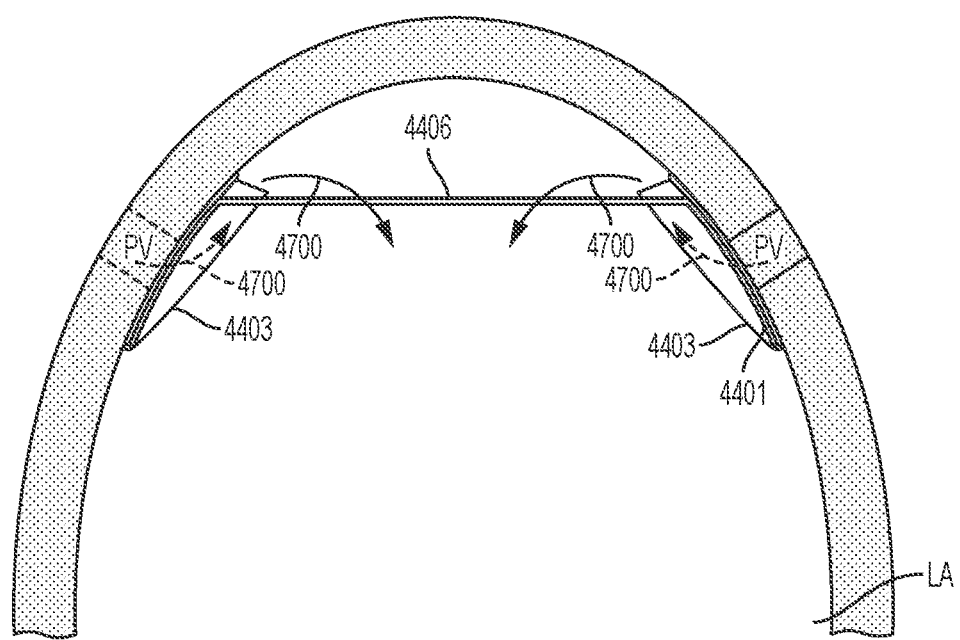
FIG. 47 illustrates a schematic of the valvular implant of FIG. 44 in an open configuration in the left atrium.

FIGS. 46 and 47 schematically illustrate the implant or device in the left atrium, for example, in an open position and a closed position, respectively, of the embodiment illustrated by FIGS. 44 and 45, when the flaps 4403 are attached to an entirety of the overlapping area between the connecting material 4402 and the flaps 4403. Regurgitant bloodflow, represented by arrows 4600 causes the flaps 4403 to be pushed back against the atrial wall and blocks blood from flowing back into the blood vessels or pulmonary veins PV. The central bridge portion 4406 spans at least a portion of the atrium when implanted in the illustrated embodiment.

FIG. 47 illustrates the implant of FIG. 46 in an open configuration. The arrows 4700 indicate the direction of the blood flow, from the blood vessels or pulmonary veins PV, applying pressure to the flaps 4403 to flex the flaps into an open or bulging position. The blood passes between the flaps and atrial wall to enter a space in the upper left atrium. From there, the blood flows through the opening 4405 in the center bridge area of the implant and toward the mitral valve. Optionally, one or both flaps could also be configured to open at the other end of the flaps so blood flows downward along the heart walls.

Figure 48:
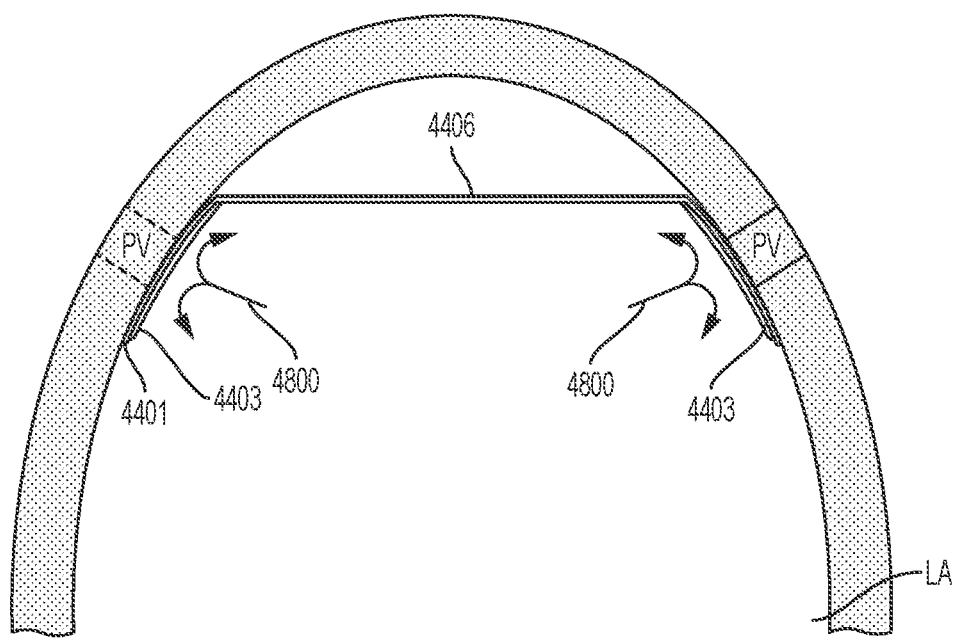
FIG. 48 illustrates a schematic of an exemplary valvular implant or device in a closed configuration in the left atrium.
Figure 49:
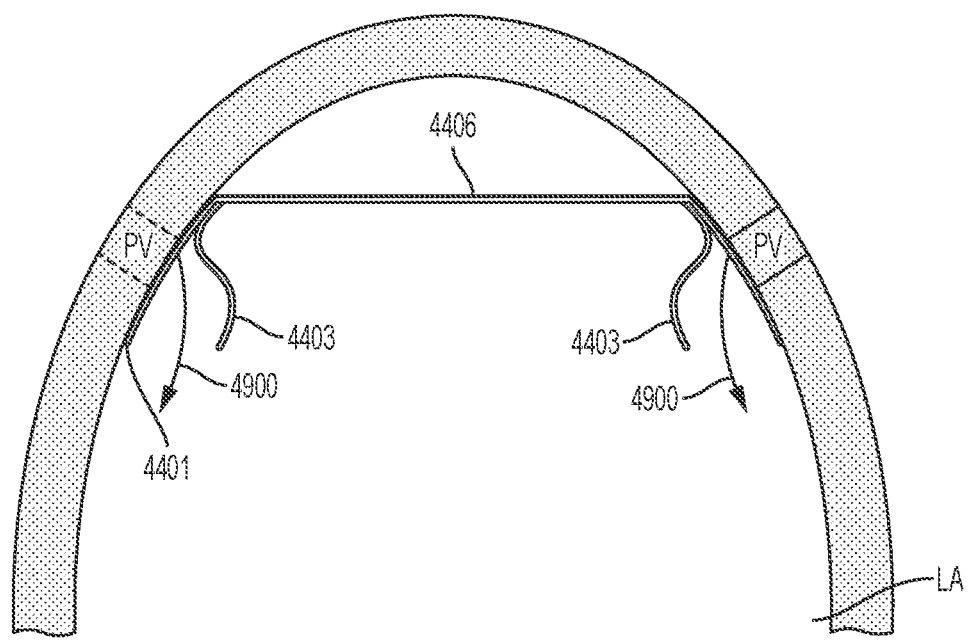
FIG. 49 illustrates a schematic of an exemplary valvular implant in an open configuration in the left atrium.

FIGS. 48 and 49 schematically illustrate the implant/device in the left atrium, for example, in an open position and a closed position, respectively, of the embodiment illustrated by FIGS. 44 and 45, when only end portion of the flaps 4403 are attached to the connecting material 4402. In FIG. 48, the implant is in a closed configuration. The arrows 4800 indicate that the regurgitant blood flow applies pressure to the flaps 4403 and pushes them up against the atrial wall and blood vessel openings or pulmonary vein openings. In FIG. 49, the implant is in an open configuration. The blood flows from the blood vessels or pulmonary veins PV and pushes the flaps outward. The blood flows past the flaps and into the atrium. The blood can flow from the pulmonary veins into the left atrium portion that is below the implant, as indicated by arrows 4900.

Figure 50:
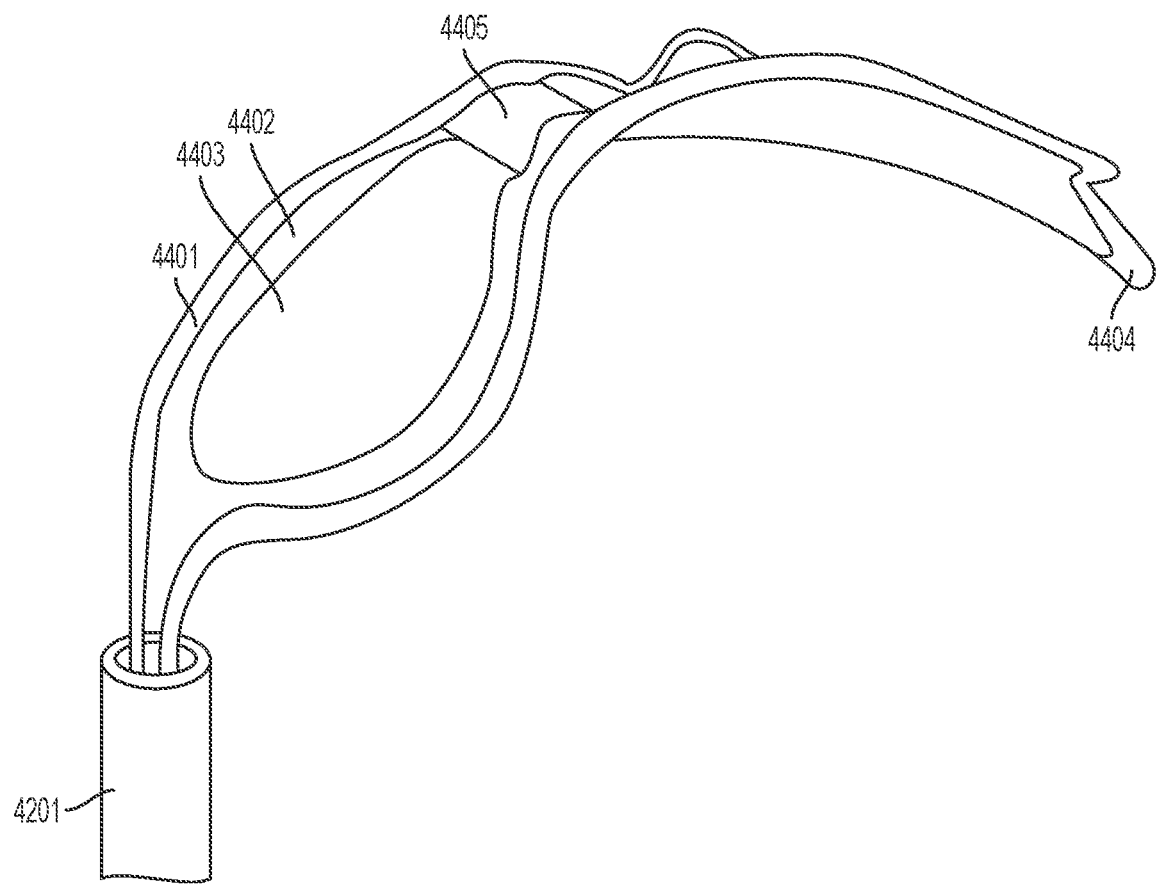
FIG. 50 illustrates a deployed valvular implant in accordance with the embodiments illustrated in FIGS. 44-49.

The deployment of the exemplary embodiments of FIGS. 44-49 can be performed in a similar manner to the deployment illustrated and described in FIGS. 42A-42I. FIG. 50 illustrates the implant frame 4401 almost fully deployed from a catheter 4201, with an end portion 4404 (not visible) still within the delivery catheter 4201. FIG. 50 is included to show that while the frame 4401 is somewhat different, the deployment is substantially the same as the embodiment illustrated by FIGS. 42A-42I, except that the bridge portion of the frame expands in the embodiments illustrated by FIGS. 44-50.

Figure 51:
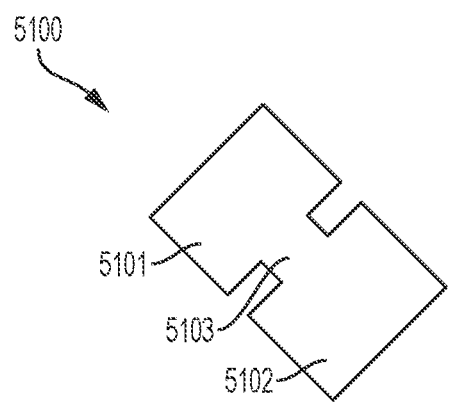
FIG. 51 illustrates a schematic of an exemplary stent cover for a valvular implant or device.
Figure 52:
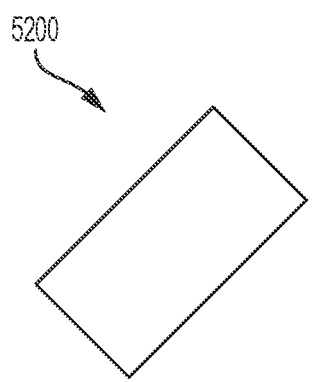
FIG. 52 illustrates a schematic of an exemplary docking ring skirt cover for a valvular implant or device.

The exemplary valve implants or systems herein (for example, implant 2800 as illustrated in FIGS. 28 and 29, implant 3000 as illustrated in FIG. 30, implant 3200 as illustrated in FIG. 32, etc.) can be covered in a soft cover that can be a soft material according to the following method(s). Two pieces of soft material can be used to cover some or all of the valve implant or system. FIG. 51 illustrates a first piece which is a stent cover 5100 (e.g., a pulmonic stent cover, etc.). The stent cover can be a single piece of material having a generally H-shaped footprint when in a flat position. The H-shaped footprint can be classified into different regions. There can be a first stent covering region 5101 and a second stent covering region 5102. The cross-piece of the "H" can be a connecting region 5103. FIG. 52 illustrates the second piece that is used to cover the implant 2800, which is a docking skirt soft cover 5200. The soft material can be a fabric, foam, and/or tissue, such as pericardial tissue.

Figure 53:
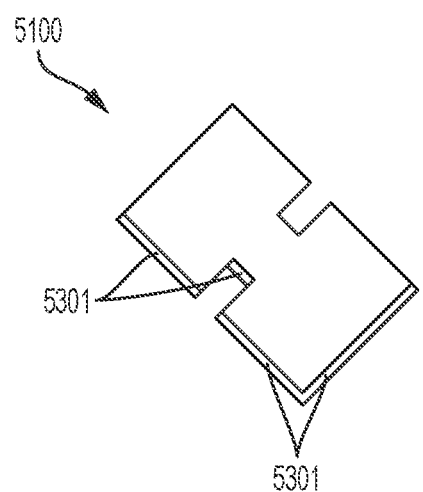
FIG. 53 illustrates a schematic of an exemplary stent cover with tapered edges for a valvular implant or device.
Figure 54:
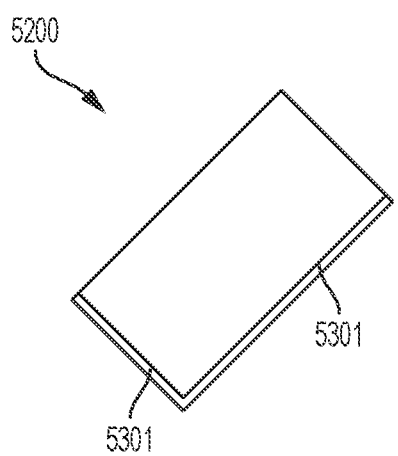
FIG. 54 illustrates a schematic of an exemplary docking ring skirt with tapered edges for a valvular implant or device.

FIG. 53 depicts that the stent cover 53 can have tapered edges 5301, and FIG. 54 depicts tapered edges 5301 on the docking skirt soft cover 5200. The tapered edges can help create a smooth surface along the edges of the material when the soft cover pieces have been assembled over a valve implant 2800.

When in a flat position, the stent cover 5100 can have dimensions sufficient to cover anchors or anchoring portions 2801 and connecting piece 2803 of a valve implant 2800. For example, the stent cover 5100 can have an overall width W0 of between 20 and 40 mm, such as between 25 and 35 mm, such as about 32.92 mm and an overall length L0 of between 30 and 70 mm, such as between 40 and 60 mm, such as about 53.50 mm in the flat position. The connecting region 5103 can have an exemplary length L3 of between 3 and 9 mm, such as between 4 and 8 mm, such as about 6.00 mm, defined by the portions cut from the entire piece to create the crossbar of the "H." The width W1 of the connecting region can be between 3 and 20 mm, such as between 6 and 17 mm, such as about 13.50 mm in the flat position, in an exemplary embodiment where the connecting region is centrally located along the width of the overall piece 5100. These exemplary dimensions give each stent covering region the dimensions of a width of between 20 and 40 mm, such as between 25 and 35 mm, such as about 32.92 mm. The first and second stent covering regions do not have to have equal areas. For example, the first stent covering region can have a length L1 of between 15 and 35 mm, such as between 20 and 30 mm, such as 23.00 mm, and the second stent covering region 5102 can have a length L2 of between 15 and 35 mm, such as between 20 and 30 mm, such as 24.50 mm. When in a flat position, the docking ring skirt soft cover 5200 can have dimensions sufficient to cover anchoring connecting piece 2803 and docking station 1401 of valve implant 2800. The docking ring skirt soft cover 5200 can have an exemplary width of 51.77 mm and an exemplary length of 27.50 mm. These measurements for both the soft cover and the docking skirt soft cover are approximate and can vary depending on the size of the implant.

Figure 55:
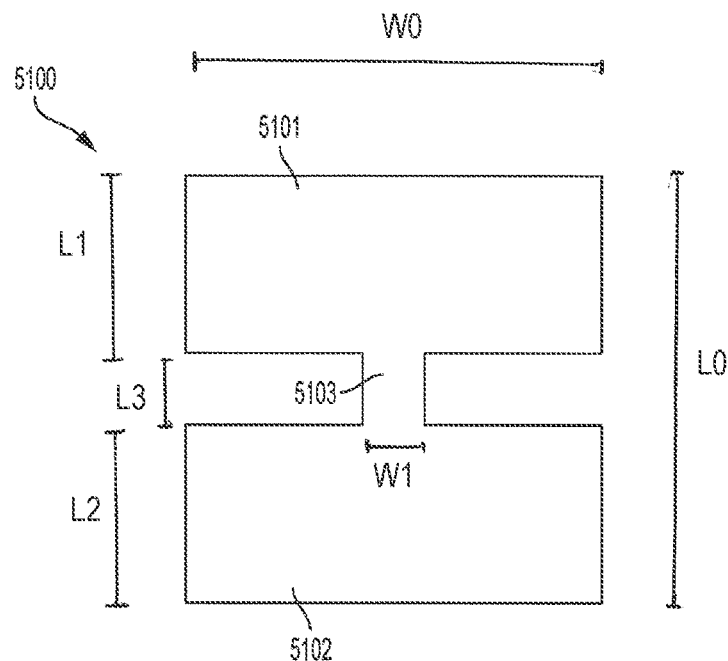
FIG. 55 illustrates another view of the schematic of an exemplary stent cover in a first position as illustrated in FIG. 54 for assembling a soft-covered valvular implant in accordance with the exemplary embodiment of FIG. 23.
Figure 56A:
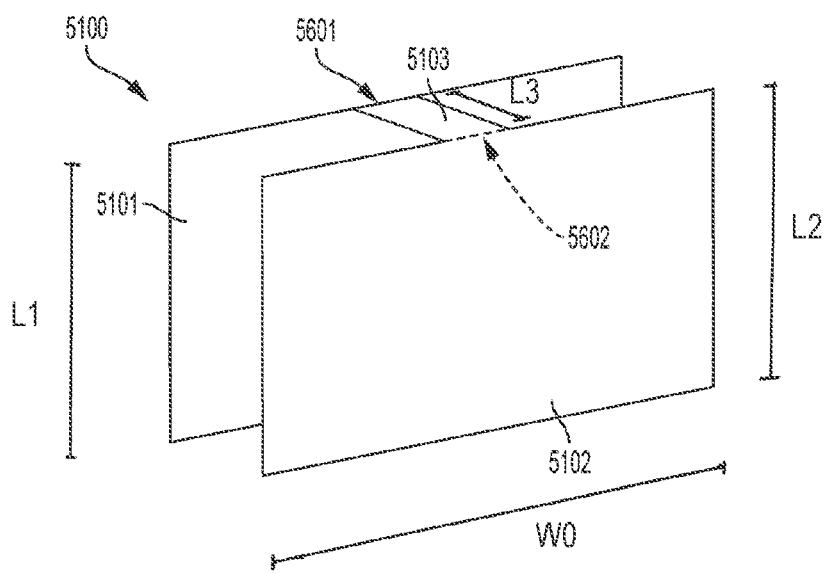
FIG. 56A illustrates a schematic of an exemplary stent cover in a second position where the sides are bent, in accordance with a method of assembling a soft-covered valvular implant in accordance with the exemplary embodiment of FIG. 23.
Figure 56B:
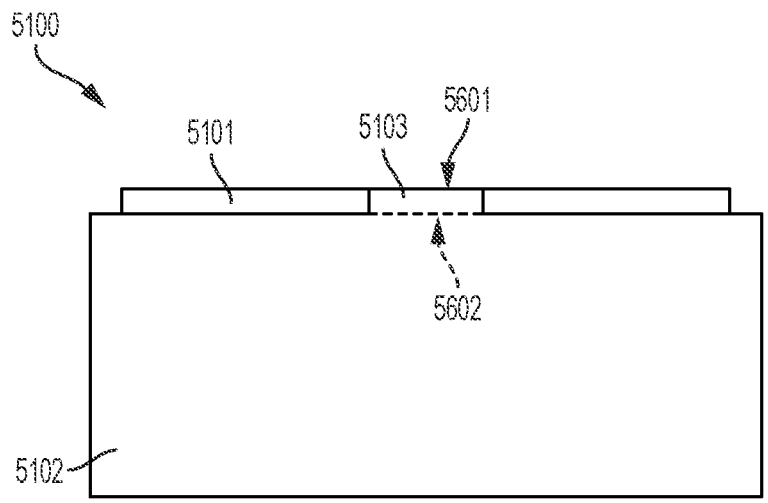
FIG. 56B illustrates a schematic side view of a stent cover in the second position as illustrated in FIG. 56A.
Figure 56C:
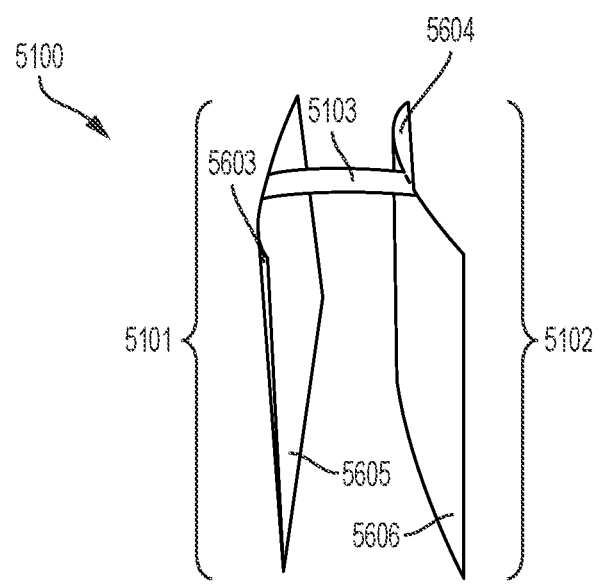
FIG. 56C illustrates a schematic front view of a stent cover in the second position as illustrated in FIG. 56A.

FIGS. 55-62 depict exemplary steps taken to cover and/or manufacture a valvular implant, such as valvular implants 2800, 3000, and/or 3200, with the soft coverings 5200 and 5300. In various embodiments, the soft coverings 5200 and 5300 are wrapped around the valve implant, with valve implant 2800 referenced and depicted here as a representative example. For simplicity, the figures which depict schematics of the steps taken, are of the soft coverings only to show how they are bent, rolled, and otherwise shaped into place. In practice the coverings can be placed over an implant, such as implant 2800. FIG. 55 depicts the stent cover 5100 in a flat position. FIG. 56A depicts the stent cover positioned with its first stent covering region 5101 and second stent covering region 5102 each bent at an angle from the soft cover connecting region 5103. The bends 5601, 5602 are flexible, and although they can be positioned at a 90-degree angle, they are flexible due to the soft material and can flex or change angles as needed to accommodate both the architecture of the implant 2800 and the anatomy of the blood vessel openings, such as the pulmonary vein openings in the left atrium wall. FIG. 56B depicts another view of a stent cover having its side regions bent. FIG. 56C depicts yet another view of the pulmonic stent cover having its side regions bent. In FIGS. 56A-C, an inner surface and outer surface for each of the stent covering regions can also be identified. The first soft cover connecting region 5101 and the second soft cover connecting region 5102 have inner surfaces 5603 and 5604, respectively. The first soft cover connecting region 5101 also has an outer surface 5605 and the second soft cover connecting region also has an outer surface 5606.

In another exemplary embodiment of covering the implant, the first stent covering region can be bent and rolled around a first stent, such as a first pulmonary vein stent, and then the second stent covering region can be bent and rolled around a second stent, such as a second pulmonary vein stent.

Figure 57:
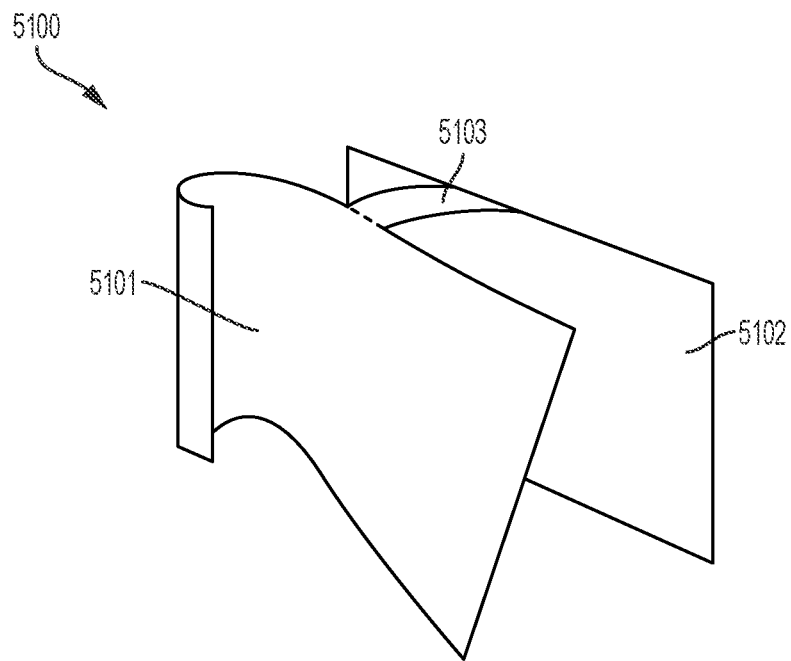
FIG. 57 illustrates a schematic perspective view of the stent cover in a third position with a first side partially curved.
Figure 58:
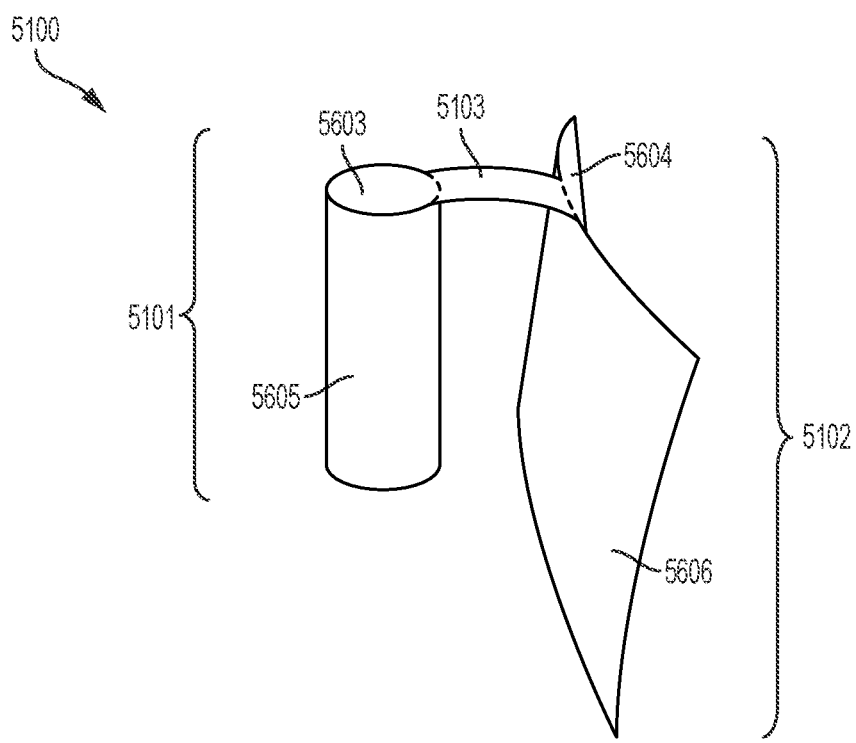
FIG. 58 illustrates a schematic perspective view of the stent cover in a fourth position as the first side forms a substantially cylindrical shape.

FIG. 57 depicts a schematic of a soft covering as the first stent covering region 5101 is starting to be wrapped around a stent (not pictured). The stent can be a first anchor or anchoring frame 2801. FIG. 58 depicts when the first stent covering region 5101 is wrapped into a substantially cylindrical shape, and can be wrapped to fully cover the outer surface of an anchor/anchoring frame 2801. The inner surface 5603 can be in snug contact with the anchor/anchoring frame 2801, and the exterior surface 5601 can make snug contact with a blood vessel or pulmonary vein upon implantation of the device.

Figure 59:
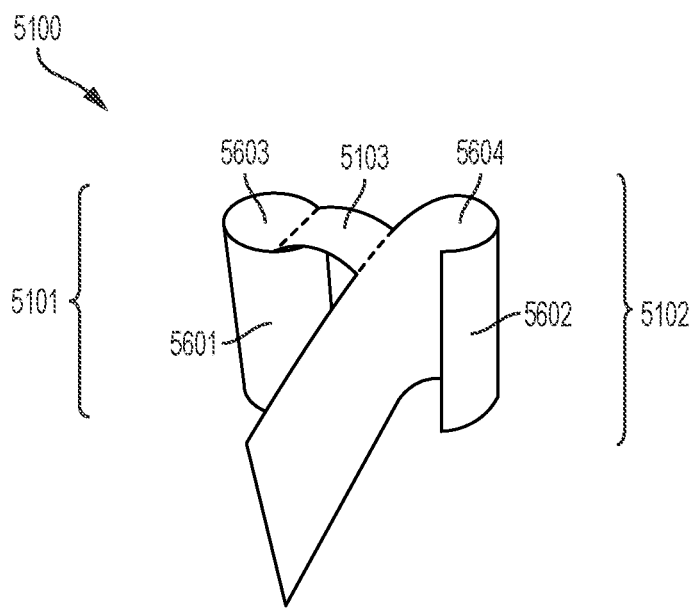
FIG. 59 illustrates a perspective view of the schematic of the stent cover in a fifth position as the second side is partially curved.
Figures 60A, 60B:
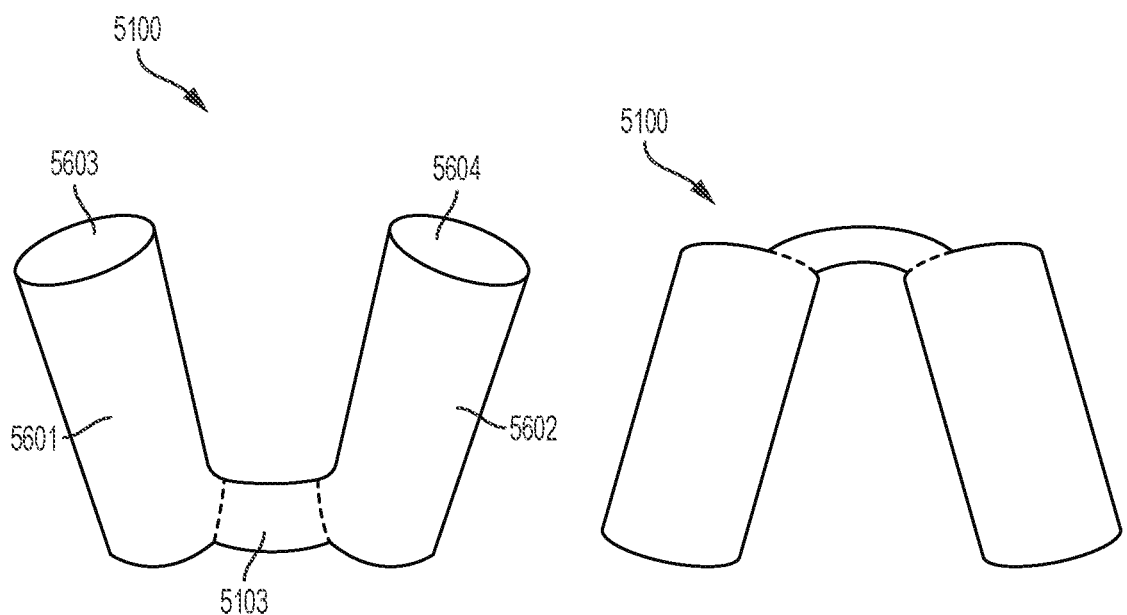
FIG. 60A illustrates a schematic of the stent cover in a sixth position with both sides now having a substantially cylindrical shape.
FIG. 60B illustrates another schematic view of the stent cover illustrated in FIG. 60A.

FIG. 59 depicts the stent cover having its second stent cover portion 5102 in a position that is beginning to be wrapped around a stent such as a second anchor/anchoring frame 2801. FIG. 60A depicts when the second stent covering region 5102 is wrapped into a substantially cylindrical shape, and can be wrapped to fully cover the outer surface of an anchoring frame 2801. The inner surface 5604 can be in snug contact with the anchor/anchoring frame 2801, and the exterior surface 5602 can make snug contact with a blood vessel or pulmonary vein upon implantation of the device. FIG. 60B depicts an alternate view of the cover 5100 from the view shown in FIG. 60A.

Figure 61:
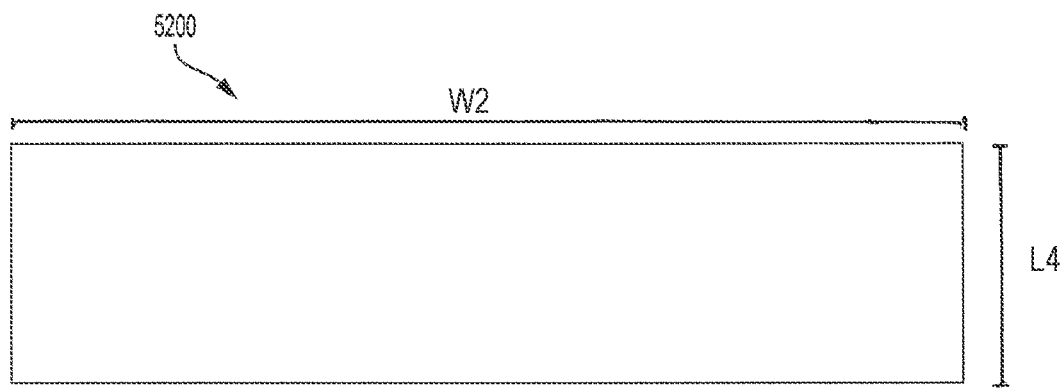
FIG. 61 illustrates a schematic of an exemplary docking ring skirt in a first flat position.

FIG. 61 depicts a second piece of soft covering, which can be a docking skirt soft covering 5200. When in a flat position, the docking skirt soft cover 5200 can have dimensions sufficient to wrap around the stent cover 5100 when it is positioned over a valve implant, such as valve implant 2800. For example, the docking skirt soft cover 5200 can have an overall width W2 of between 30 and 70 mm, such as between 40 and 60 mm, such as about 51.77 mm and an overall length L4 of between 20 and 40 mm, such as between 25 and 35 mm, such as about 27.5 mm in the flat position.

Figure 62:
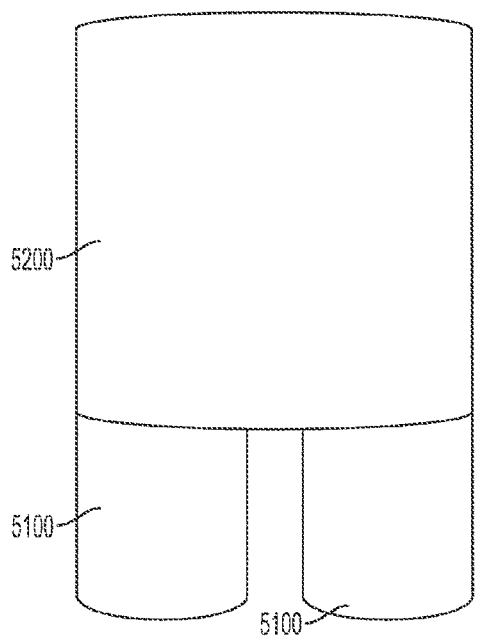
FIG. 62 illustrates a schematic of an exemplary docking ring skirt in a second position, wrapped around the stent cover.

Referring to FIG. 62, the docking skirt soft covering is wrapped around the stent cover 5100 and the docking station 1401 of implant 2800. The docking skirt soft cover 5200 is secured into place. The docking skirt soft cover 5200 can be secured to both the covering portions 5101, 5102 and the connecting portion 5103 to prevent leakage between the cover 5200 and the cover 5100. That is, the portion 5103 blocks flow from the cover 5200 between the portions 5101 and 5102 of the cover 5100.

Figure 63A:
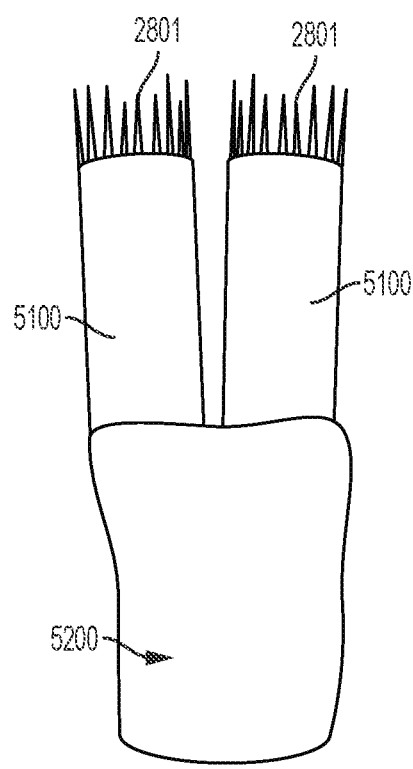
FIG. 63A illustrates a schematic of exemplary soft coverings applied to a valvular implant in accordance with an exemplary embodiment.
Figure 63B:
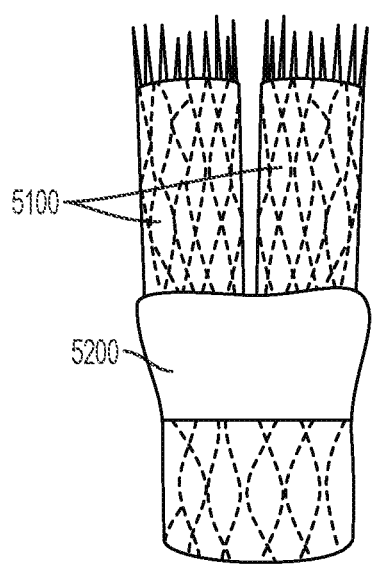
FIG. 63B illustrates a schematic of exemplary soft coverings applied to a valvular implant and underlying frame.

FIG. 63A depicts another schematic of the soft coverings wrapped around an implant 2800 as outer covers/coverings. In this figure, the anchors/anchoring frames 2801 are included for reference. FIG. 63B depicts another schematic of an exemplary embodiment, where the soft coverings 5100 and 5200 are translucent and the frame of implant 2800 can be seen through some a single layer of soft covering material.

Figure 64:
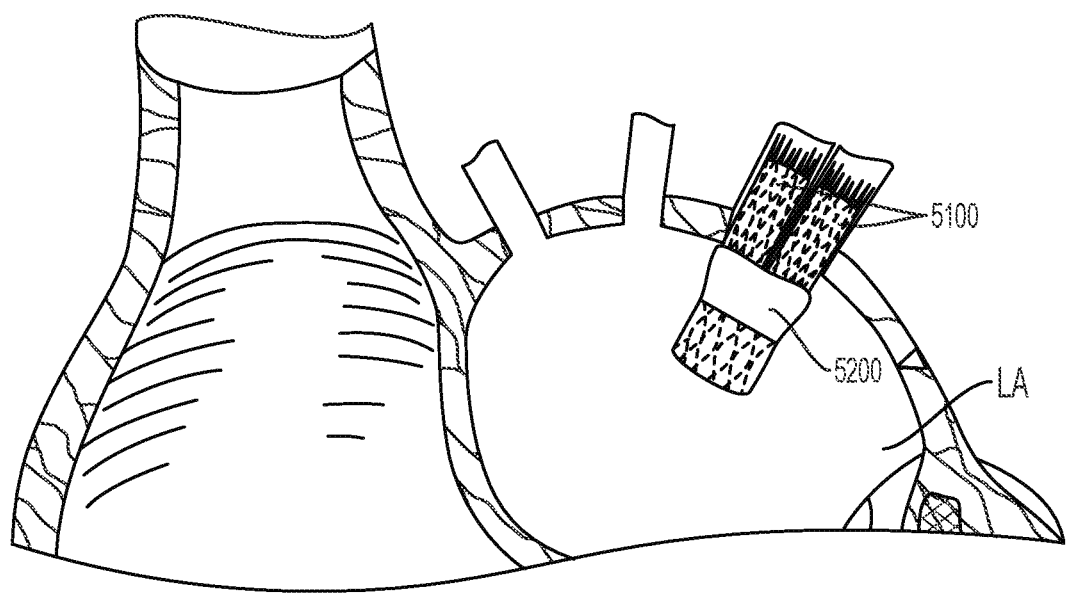
FIG. 64 illustrates a schematic of the valvular implant implanted in the left atrium in accordance with the exemplary embodiments of FIGS. 51-63B.

FIG. 64 depicts a schematic of a pulmonary vein valve implant 2800 wrapped in soft coverings 5100 and 5200 (shown as outer coverings), and where it can be implanted in the heart. The first stent covering region 5101 covering a first anchor/anchoring frame 2801 is implanted into a pulmonary vein, and a second stent covering region 5102 wrapped around a second anchor/anchoring frame 2801 is implanted into another pulmonary vein. The docking skirt soft cover 5200 wrapped around the docking station 1401 is positioned in the left atrium. A valve, as explained in the exemplary embodiments described herein, can be secured inside the dock or docking station 1401.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art. Additionally, any and all of the methods relating to use of the devices, implants, systems, etc. described herein can be performed on a living animal or on a non-living cadaver, cadaver heart, simulator, anthropomorphic ghost, etc.

In view of the many possible embodiments to which the principles of the disclosure can be applied, it should be recognized that the illustrated embodiments are only preferred examples and should not be taken as limiting the scope of the disclosure. Rather the scope of the disclosure is defined by the following claims.

What is claimed is:

1. A device for blocking regurgitant blood flow into first and second pulmonary vein openings in a left atrium of a heart, comprising:
   at least one resilient frame;
   at least one valve comprising one or more membranes;
   wherein the at least one valve has an open configuration and a closed configuration in which a first membrane of the one or more membranes is configured to abut an atrial wall of the left atrium around the first and second pulmonary vein openings to cover and seal over the first and second pulmonary vein openings;
   wherein the at least one resilient frame is configured to hold the at least one valve in the left atrium between the first and second pulmonary vein openings and a mitral valve of the heart;
   wherein the device is configured such that the open configuration of the at least one valve permits blood to flow from the first and second pulmonary vein openings into the left atrium and to the mitral valve when the device is deployed in the left atrium; and
   wherein the device is configured such that the closed configuration of the at least one valve blocks regurgitant blood flow through the mitral valve into the first and second pulmonary vein openings when the device is deployed in the left atrium.

2. The device of claim 1, wherein the first membrane has an opening and the one or more membranes further comprises a second membrane attached to the first membrane.

3. The device of claim 2 wherein the second membrane comprises one or more of pericardium, ePTFE or PET.

4. The device of claim 1, wherein the one or more membranes comprises a membrane that is configured to bunch up on itself to open the at least one valve.

5. The device of claim 1, wherein the at least one resilient frame is expandable into conforming engagement with the left atrium.

6. The device of claim 1 wherein the at least one resilient frame comprises one or more of a ring and a stent.

7. The device of claim 1, wherein the first membrane of the one or more membranes is configured to abut an atrial wall of the left atrium around third and fourth pulmonary vein openings to cover the first, second, third, and fourth pulmonary vein openings.

8. The device of claim 1, wherein the at least one resilient frame includes a dome shaped support portion configured to position the first membrane against the atrial wall of the left atrium.

9. The device of claim 1, wherein the at least one valve comprises a first valve including the first membrane and a second valve including a second membrane configured to abut an atrial wall of the left atrium around third and fourth pulmonary vein openings to cover and seal over the third and fourth pulmonary vein openings.

10. A method of implanting a device for blocking regurgitant flow into first and second pulmonary vein openings of a heart, the method comprising:
    advancing a delivery tube containing the device in an unexpanded condition into a left atrium of the heart;
    expanding the device in the left atrium to position the device in the left atrium between the pulmonary vein opening and the mitral valve;
    wherein the device is configured to move to an open configuration permitting blood to flow from the first and second pulmonary vein openings into the mitral valve during diastole; and
    wherein the device is configured to move to a closed configuration in which a first membrane of one or more membranes of the device abuts an atrial wall of the left atrium around the first and second pulmonary vein openings to cover and seal over the first and second pulmonary vein openings, thereby blocking regurgitant blood flow through the mitral valve into the first and second pulmonary vein openings during systole.

11. The method of claim 10, wherein the device comprises an integrated valve including the one or more membranes.

12. The method of claim 10 wherein the device comprises one or more of a ring and a stent.

13. The method of claim 10, wherein the first membrane of the one or more membranes abuts the atrial wall of the left atrium around third and fourth pulmonary vein openings to cover the first, second, third, and fourth pulmonary vein openings when the device is in the closed configuration.

14. The method of claim 10, wherein expanding the device in the left atrium to position the device in the left atrium between the first and second pulmonary vein openings and the mitral valve comprises expanding a dome shaped portion of the device to position the first membrane of the one or more membranes against the atrial wall of the left atrium.

15. A system comprising:
    a device for blocking regurgitant blood flow into first and second pulmonary vein openings in a left atrium of a heart, comprising:
      at least one expandable frame;
      at least one valve connected to the at least one expandable frame and comprising one or more membranes;
      wherein the at least one valve has an open configuration and a closed configuration in which a first membrane of the one or more membranes is configured to abut an atrial wall of the left atrium around the first and second pulmonary vein openings to cover and seal over the first and second pulmonary vein openings;
      wherein the at least one expandable frame is configured to hold the at least one valve in the left atrium between the first and second pulmonary vein openings and a mitral valve of the heart;

wherein the device is configured such that the open configuration of the at least one valve permits blood to flow from the first and second pulmonary vein openings into the left atrium and to the mitral valve when the device is deployed in the left atrium;

wherein the device is configured such that the closed configuration of the at least one valve blocks regurgitant blood flow through the mitral valve into the first and second pulmonary vein openings when the device is deployed in the left atrium;

a delivery tube configured to retain the expandable frame in an unexpanded condition; and wherein the delivery tube is configured to deploy the expandable frame in the left atrium of the heart.

16. The system of claim 15 wherein the one or more membranes are attached to the frame.

17. The system of claim 15 wherein the first membrane has an opening and the one or more membranes comprises a second membrane attached to the first membrane.

18. The system of claim 15, wherein the expandable frame comprises a first looped frame portion and a second looped frame portion connected by a bridge.

19. The system of claim 15 wherein the at least one expandable frame comprises one or more of a ring and a stent.

20. The system of claim 15, wherein the at least one valve comprises a first valve including the first membrane and a second valve including a second membrane configured to abut an atrial wall of the left atrium around third and fourth pulmonary vein openings to cover and seal over the third and fourth pulmonary vein openings.

* * * * *